(12) United States Patent
Payne et al.

(10) Patent No.: US 8,168,608 B2
(45) Date of Patent: May 1, 2012

(54) PROMOTER AND PLASMID SYSTEM FOR GENETIC ENGINEERING

(75) Inventors: Mark S. Payne, Wilmington, DE (US); Stephen K. Picataggio, Solana Beach, CA (US); Amy Kuang-Hsu, Redwood City, CA (US); Ramesh Velayudhan Nair, Cupertino, CA (US); Fernando Valle, Burlingame, CA (US); Philippe Soucaille, Deyme (FR); Donald Eugene Trimbur, Palo Alto, CA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/940,225

(22) Filed: Nov. 5, 2010

(65) Prior Publication Data

US 2011/0046014 A1  Feb. 24, 2011

Related U.S. Application Data

(60) Continuation of application No. 12/370,864, filed on Feb. 13, 2009, now abandoned, which is a division of application No. 11/541,810, filed on Oct. 2, 2006, now Pat. No. 7,510,869, which is a division of application No. 10/739,542, filed on Dec. 18, 2003, now Pat. No. 7,132,527, which is a continuation of application No. 10/420,587, filed on Apr. 22, 2003.

(60) Provisional application No. 60/374,931, filed on Apr. 22, 2002.

(51) Int. Cl.
*A61K 48/00* (2006.01)
*C12N 15/64* (2006.01)
*C12N 1/20* (2006.01)
*C07H 21/02* (2006.01)
*C07H 21/04* (2006.01)

(52) U.S. Cl. ...... 514/44; 435/91.4; 435/252.3; 536/23.1

(58) Field of Classification Search .................. None
See application file for complete search history.

(56) References Cited

OTHER PUBLICATIONS

Suzuki et al., 1999, PNAS, USA, 96: 2285-2290.*

* cited by examiner

*Primary Examiner* — Joanne Hama
(74) *Attorney, Agent, or Firm* — Roger W. Herrell, Jr.

(57) ABSTRACT

This invention provides a series of low-copy number plasmids comprising restriction endonuclease recognition sites useful for cloning at least three different genes or operons, each flanked by a terminator sequence, the plasmids containing variants of glucose isomerase promoters for varying levels of protein expression. The materials and methods are useful for genetic engineering in microorganisms, especially where multiple genetic insertions are sought.

3 Claims, No Drawings

PROMOTER AND PLASMID SYSTEM FOR GENETIC ENGINEERING

This application claims the benefit of U.S. Provisional Application No. 60/374,931, filed Apr. 22, 2002.

FIELD OF THE INVENTION

This invention is in the field of molecular biology. More specifically, this invention pertains to a series of low-copy-number plasmids comprising restriction endonuclease recognition sites useful for cloning at least three different genes or operons, each site flanked by a terminator sequence and a set of promoters for varying levels of protein expression. The invention is useful for genetic engineering in microorganisms, especially where multiple genetic insertions are sought.

BACKGROUND OF THE INVENTION

Molecular biotechnology is a discipline that is based on the ability of researchers to transfer specific units of genetic information from one organism to another. This process, known as cloning, relies on the techniques of recombinant DNA technology to produce a useful product or a commercial process (Glick, B. R.; Pasternak, J. J., *Molecular Biotechnology Principles and Applications of Recombinant DNA*, $2^{nd}$ ed. American Society for Microbiology, Washington, D.C. (1998)).

Commercial processes often require that proteins encoded by the cloned gene are produced at high rates of expression. There is no single strategy for achieving maximal expression of every cloned gene. Most cloned genes have distinctive molecular properties that require the investment of considerable time and effort before a specific set of conditions that result in an acceptable level of expression is found.

Merely inserting a gene into a cloning vector does not ensure that it will be successfully expressed at the level needed. In response to the need for a high expression rate, many specialized expression vectors have been created by manipulating a number of different genetic elements that control aspects of transcription, translation, protein stability, oxygen limitation, and secretion from the host cell. More specifically, the molecular features that have been manipulated to control gene expression include: (1) the nature of the relevant transcriptional promoter and terminator sequences, (2) the strength of the ribosome binding site, (3) the number of copies of the cloned gene and whether the gene is plasmid-borne or integrated into the genome of the host cell, (4) the final cellular location of the synthesized foreign protein, (5) the efficiency of translation in the host organism, and (6) the intrinsic stability of the cloned gene protein within the host cell.

Additionally, the introduction and expression of foreign DNA in a host organism often changes the metabolism of the organism in ways that may impair normal cellular functioning. This phenomenon is due to a metabolic load or burden imposed upon the host by the foreign DNA. The metabolic load may result from a variety of conditions including 1) increasing plasmid copy number, 2) overproduction of proteins, 3) saturation of export sites, and/or 4) interference of cellular function by the foreign protein itself.

Techniques to address some of the obstacles presented above are known. Several groups have used multiple promoters in tandem to express genes at different phases of cell growth (CN 1186856), from different RNA polymerases or in different phage species (U.S. Pat. No. 5,547,862; *J. Biotechnol.* 2(5):303-316 (1985); *Biotechniques*, 18(1):152-154, 156-157(1995)). Another group has used tandem repeated multiple cloning sites (MCS) (*Gene,* 139 (1):83-86 (1994)) to facilitate moving DNA in and out of the plasmid vector. One group has reported the use of a high-copy-number vector with three multiple cloning sites each behind a different promoter for expression of different genes in mammalian cells (*Biotech. Bioeng.,* 57(1):1-10 (1998)).

Despite these techniques, the problem to be solved remains how to easily and quickly clone multiple genes or operons while minimizing the impact of metabolic load, controlling the yield of the recombinant protein to meet production needs, and enhancing the stability of the transformed host cell.

SUMMARY OF THE INVENTION

Applicants have created novel glucose isomerase promoter sequences that allow varying levels of gene expression in production organisms. Applicants incorporated expression cassettes containing the variant GI promoters into a low-copy-number plasmid derived from pCL1920 to construct a series of plasmids for genetic engineering. Transcription terminators isolate the associated promoter from transcription from other promoters located outside this construct.

Applicants also have constructed a unique nucleotide sequence containing cloning sites for multiple rare restriction enzymes, further facilitating cloning in this construct or transfer of this construct to alternate plasmid or vector backbones. The unique cloning sites allow introduction of genes or operons to be expressed under the control of suitable promoters of varying strengths.

The invention encompasses:

1. an isolated or recombinant nucleic acid molecule encoding a *Streptomyces lividins* glucose isomerase variant, the nucleic acid molecule selected from the group consisting of SEQ ID NOS:9-28;

2. an isolated or recombinant nucleic acid molecule encoding a *Streptomyces lividins* glucose isomerase variant, the nucleic acid molecule comprising a nucleotide sequence of any of SEQ ID NOs:9-28;

3. a library of isolated or recombinant nucleic acid molecules encoding a *Streptomyces lividins* glucose isomerase variant, the library comprising the nucleotide sequences of SEQ ID NOS:9-28;

4. an expression cassette comprising the nucleic acid molecule of the various GI variants set out above, and;

5. a kit comprising the nucleic acid molecules encoding the various *Streptomyes lividins* glucose isomerase variants set out above.

A further embodiment of the invention is a DNA construct comprising at least three transcriptional terminators and at least one cloning site situated between any two transcriptional terminators. A preferred embodiment of this DNA construct comprises the transcriptional terminators tonB, thrA, or aspA, and the cloning sites are selected from the group consisting of AvrII, NheI, BfaI, Cac8I, BsaJI, and StyI. Preferred cloning sites are NheI or AvrII. A library of these constructs is also encompassed in the invention.

The invention includes the following DNA constructs:
the pSYCO109mcs plasmid consisting of SEQ ID NO:30,
the short 1.5 GI promoter consisting of SEQ ID NO:31,
the short 1.20 GI promoter consisting of SEQ ID NO:32,
the pAH105 plasmid consisting of SEQ ID NO:70,
the pSYCO101 plasmid consisting of SEQ ID NO:71,
the pSYCO103 plasmid consisting of SEQ ID NO:72,
the pSYCO106 plasmid consisting of SEQ ID NO:73,
the pSYCO109 plasmid consisting of SEQ ID NO:74, the pSCYO106mcs plasmid consisting of SEQ ID NO:78, and the pRJ50 plasmid consisting of SEQ ID NO:79.

A further embodiment of the invention is a vector having a multiple cloning site containing restriction recognition site sequences specific for the restriction endonucleases AscI, NheI, PacI, RsrII, NsiI, SacII, MluI, AgeI, SapI, and SnaBI. A particular embodiment of this vector is the nucleotide sequence of SEQ ID NO:77.

The genetic materials of this invention include transformed host cells containing the nucleic acid molecules described above and the polypeptides encoded by the polynucleotides.

BRIEF DESCRIPTION OF THE SEQUENCE LISTING AND BIOLOGICAL DEPOSIT

Applicants have provided 83 sequences in conformity with Rules for the Standard Representation of Nucleotide and Amino Acid Sequences in Patent Applications (Annexes I and II to the Decision of the President of the EPO, published in Supplement No. 2 to OJ EPO, December/1992), with 37 C.F.R. 1.821-1.825 and Appendices A and B (Requirements for Application Disclosures Containing Nucleotides and/or Amino Acid Sequences) with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021-3030 (1985) and in the *Biochemical Journal* 219 (No. 2):345-373 (1984) which are herein incorporated by reference.

SEQ ID NO:1 is the nucleotide sequence for the wildtype *Streptomyces lividans* glucose isomerase (GI) promoter.

SEQ ID NOs:2-8 are oligonucleotide primers used for saturation mutagenesis of the GI promoter. In SEQ ID NOs: 3-8, "N" represents either A, T, C, or G.

SEQ ID NOs:9-28 are nucleotide sequences for the GI promoter variants.

SEQ ID NO:29 is the nucleotide sequence for the yqhD gene from *E. coli*.

SEQ ID NO:30 is the nucleotide sequence for the pSYCO109mcs plasmid.

SEQ ID NO:31 is the nucleotide sequence for the short 1.5 GI promoter.

SEQ ID NO:32 is the nucleotide sequence for the short 1.20 GI promoter.

SEQ ID NO:33 is the nucleotide sequence for the short wild-type GI promoter.

SEQ ID NOs:34-37 are the oligonucleotide primers used for amplification of yqhD with incorporation of the short GI promoters.

SEQ ID NOs:38-39 are oligonucleotide primers used to construct the yqhD disruption.

SEQ ID NOs:40-43 are oligonucleotide primers used to confirm disruption of yqhD.

SEQ ID NOs:44-46 are oligonucleotide primers used for replacement of the chromosomal ppc promoter with the short wild-type GI promoter.

SEQ ID NO:47 is the nucleotide sequence for a multiple cloning site and terminator.

SEQ ID NO:48 is the nucleotide sequence for the pHK28-26 plasmid.

SEQ ID NOs:49-50 are oligonucleotide primers used to amplify dhaB3.

SEQ ID NOs:51-52 are oligonucleotide primers used to amplify dhaB1.

SEQ ID NOs:53-54 are oligonucleotide primers used to create the dhaT deletion.

SEQ ID NOs:55-56 are oligonucleotides used to create a linker.

SEQ ID NO:57 is a nucleotide sequence encoding three transcriptional terminators separated by restriction sites.

SEQ ID NOs:58-59 are oligonucleotides used to create SEQ ID NO:60.

SEQ ID NO:60 is the nucleotide sequence encoding three transcriptional terminators flanked by EcoRI and KpnI sites.

SEQ ID NOs:61-62 are oligonucleotide primers used to amplify SEQ ID NO:60.

SEQ ID NOs:63-66 are oligonucleotide primers used to amplify an expression cassette.

SEQ ID NO:67 is the nucleotide sequence of a double-stranded linker used to generate pCR-pCL1920.

SEQ ID NOs:68-69 are oligonucleotide primers used to amplify the rrnBT1T2 terminator from pTrc99A.

SEQ ID NO:70 is the nucleotide sequence for the pAH105 plasmid.

SEQ ID NO:71 is the nucleotide sequence for the pSYCO101 plasmid

SEQ ID NO:72 is the nucleotide sequence for the pSYCO103 plasmid

SEQ ID NO:73 is the nucleotide sequence for the pSYCO106 plasmid

SEQ ID NO:74 is the nucleotide sequence for the pSYCO109 plasmid

SEQ ID NOs:75-76 are oligonucleotide primers used to form SEQ ID NO:77.

SEQ ID NO:77 is the nucleotide sequence of a multiple cloning fragment containing restriction recognition sites for the following enzymes: NheI, RsrII, SacI, AgeI, SnaBI, AscI, PacI, NsiI, MluI, and SapI.

SEQ ID NO:78 is the nucleotide sequence for the pSCYO106mcs plasmid.

SEQ ID NO:79 is the nucleotide sequence for the pRJ50 plasmid.

SEQ ID NOs:80-81 are oligonucleotide primers used to amplify the orf operon.

SEQ ID NOs:82-83 are oligonucleotide primers to check transformants in Example 4.

Applicants have made the following biological deposit under the terms of the Budapest Treaty on the International Recognition of the Deposit of Microorganisms for the Purposes of Patent Procedure:

| Depositor Identification Reference | Int'l. Depository Designation | Date of Deposit |
|---|---|---|
| *Escherichia coli* RJ8n | ATCC PTA-4216 | 9 Apr. 2002 |

As used herein, "ATCC" refers to the American Type Culture Collection International Depository located 10801 University Blvd., Manassas, Va. 20110-1109, U.S.A. The "ATCC No." is the accession number to cultures on deposit with the ATCC.

The listed deposits will be maintained in the indicated international depository for at least thirty (30) years and will be made available to the public upon grant of a patent disclosing it. The availability of a deposit does not constitute a license to practice the subject invention in derogation of patent rights granted by government action.

DETAILED DESCRIPTION OF THE INVENTION

The Applicants have solved the stated problem by creating a series of constructs containing at least three unique cloning sites, each cloning site operably separated from each other by transcription terminators and promoters of different strengths. The promoters of different strengths are variants of the *Streptomyces lividans* glucose isomerase (GI) promoter (SEQ ID NO:1). Combining the variant GI promoters in expression cassettes with a SYCO plasmid as the production platform provides a system useful for biocatalyst development in a wide variety of bioprocess projects.

The invention allows the facile and stable incorporation of endogenous or exogenous genes or operons in a vector controlling the levels of gene expression. The use of the single plasmid to express multiple genes or operons reduces the number of antibiotic markers needed to maintain the multiple plasmids in the *E. coli* host that previous methods required to produce a gene product. Use of the invention can minimize the impact of metabolic load, optimize the yield of the recombinant protein, and enhance the stability of the transformed host cell. The invention is especially useful for genetic engineering in bioprocesses where expressing two or more genes or operons may be required for product formation.

Applicants have created novel GI promoter sequences that allow varying levels of gene expression. Applicants incorporated expression cassettes containing the variant GI promoters into a low-copy-number plasmid derived from pCL1920 to construct a series of plasmids for genetic engineering. The transcription terminators isolate the associated promoter from transcription from other promoters located outside this construct.

Applicants also have constructed a unique nucleotide sequence containing cloning sites for at least ten rare restriction enzymes, further facilitating cloning in this construct or transfer of this construct to alternate plasmid or vector backbones. The unique cloning sites allow introduction of genes or operons to be expressed under the control of suitable promoters of varying strengths. Further, a given construct may be flanked by unique cloning sites for facile integration into any number of plasmid backbones including pUC, pBR322, pACYC, pSC101, or others known and contemplated by those skilled in the art.

Applicants have demonstrated a specific utility of the invention in the biosynthesis of 1,3-propanediol (3G) from glucose in *E. coli* transformed with the claimed materials. Expression cassettes were constructed in a low-copy-number plasmid as described herein and genes for production of 1,3-propanediol were cloned into this vector. The invention may be used to vary gene expression in other expression systems.

Definitions

The following definitions and abbreviations are to be used to interpret the claims and specification.

"Open reading frame" is abbreviated ORF.

"Polymerase chain reaction" is abbreviated PCR.

The terms "host cell" or "host organism" refer to a microorganism capable of receiving foreign or heterologous genes or multiple copies of endogenous genes and of expressing those genes to produce an active gene product.

The terms "DNA construct" or "construct" refer to an artificially constructed fragment of DNA.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign", "exogenous", or "heterologous" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure. A "gene construct" refers to a nucleic acid fragment that encodes for expression of one or more specific proteins. In the gene construct the gene may be native, chimeric, or foreign in nature.

The term "isolated nucleic acid" refers to a nucleic acid (e.g., an RNA, DNA, or a mixed polymer) which is substantially separated from other components that naturally accompany a native sequence (e.g., ribosomes, polymerases, and/or flanking genomic sequences from the originating species). The term includes recombinant or cloned DNA isolates and chemically synthesized analogs or analogs biologically synthesized by heterologous systems.

The terms "encoding" and "coding" refer to the process by which a gene, through the mechanisms of transcription and translation, produces an amino acid sequence. The process of encoding a specific amino acid sequence includes DNA sequences that may involve base changes that do not cause a change in the encoded amino acid, or which involve base changes which may alter one or more amino acids, but do not affect the functional properties of the protein encoded by the DNA sequence. It is therefore understood that the invention encompasses more than the specific exemplary sequences. Modifications to the sequence, such as deletions, insertions, or substitutions in the sequence which produce silent changes that do not substantially affect the functional properties of the resulting protein molecule are also contemplated. For example, alterations in the gene sequence which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue (such as glycine), or a more hydrophobic residue (such as valine, leucine, or isoleucine). Similarly, changes that result in substitution of one negatively charged residue for another (such as aspartic acid for glutamic acid), or one positively charged residue for another (such as lysine for arginine) can also be expected to produce a biologically equivalent product. Nucleotide changes which result in alteration of the N-terminal and C-terminal portions of the protein molecule would also not be expected to alter the activity of the protein. In some cases, it may in fact be desirable to make mutants of the sequence in order to study the effect of alteration on the biological activity of the protein. Each of the proposed modifications is well within the routine skill in the art, as is determination of retention of biological activity in the encoded products. Moreover, the skilled artisan recognizes that sequences encompassed by this invention are also defined by their ability to hybridize, under stringent conditions (0.1×SSC, 0.1% SDS, 65° C.), with the sequences exemplified herein.

The term "expression" refers to the transcription and translation to gene product from a gene coding for the sequence of the gene product.

The term "promoter" refers to a region of DNA to which RNA polymerase binds and initiates the transcription of a gene.

The terms "transcription terminator" or "terminator" refer to the genetic element that ends protein synthesis.

The term "operon" refers to a cluster of genes that are coordinately regulated.

The terms "polypeptide" and "protein" are used interchangeably to refer to the gene product.

The terms "plasmid", "vector", and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences (linear or circular) of a single- or double-stranded DNA or RNA, derived from any source. Such elements contain a number of nucleotide sequences that have been joined or recombined into a unique construction capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in its host.

The term "restriction endonucleases" refers to a class of enzymes that cut a given length of DNA at a specific and unique internal location. By creating the cut in the DNA, restriction endonucleases enable the subsequent splicing or insertion of segments of DNA into the internal location. The terms "restriction site" or "restriction recognition site" refer to a nucleotide sequence (of base pairs) in a DNA molecule that is "recognized" and cut by a given restriction enzyme.

The term "rare", as applied to restriction enzyme sites, refers to the low frequency of occurrence of a given sequence in a gene. A preferred group of rare restriction enzymes sites for purposes of this specification are AscI, NheI, PacI, RsrII, NsiI, SacII, MluI, AgeI, SapI, and SnaBI.

The term "cloning site" refers to a location on a vector into which DNA can be inserted. The term "multiple cloning site" or "mcs" refers to a synthetic DNA sequence that contains any one or a number of different restriction enzyme sites to permit insertion at a defined locus (the restriction site) on a vector. The term "unique cloning site" refers to a cloning site that appears one time with a given DNA sequence.

In describing the relative locations of the elements of a vector, a given site or locus of interest is "between" two others if it is situated in the intermediate length of DNA that separates the two others. In the case of a circular vector, the given site or locus of interest is "between" two others if it is situated within the shortest length of DNA that separates the two other sites on the vector. The given site or locus is said to be "flanked" by another situated either preceding or following the site or locus of interest.

The term "genetically altered" refers to the process of changing hereditary material by transformation or mutation. The terms "transformation" and "transfection" refer to the acquisition of new genes in a cell after the incorporation of nucleic acid. The acquired genes may be integrated into chromosomal DNA or introduced as extrachromosomal replicating sequences. The term "transformant" refers to the product of a transformation.

The terms "glycerol dehydratase" or "dehydratase enzyme" refer to the polypeptide(s) responsible for a coenzyme $B_{12}$-dependent enzyme activity that is capable of isomerizing or converting a glycerol molecule to the product 3-hydroxypropionaldehyde. For the purposes of the present invention, the dehydratase enzymes include a glycerol dehydratase (GenBank U09771, U30903) and a diol dehydratase (GenBank D45071) having preferred substrates of glycerol and 1,2-propanediol, respectively. Glycerol dehydratase of $K.$ $pneumoniae$ ATCC 25955 is encoded by the genes dhaB1, dhaB2, and dhaB3 (GenBank U30903). The dhaB1, dhaB2 and dhaB3 genes code for the $\alpha$, $\beta$, and $\gamma$ subunits of the glycerol dehydratase enzyme, respectively. Glycerol dehydratase and diol dehydratase are complexes (with an $\alpha_2\beta_2\gamma_2$ subunit composition) that utilize coenzyme $B_{12}$.

Glycerol and diol hydratases are subject to mechanism-based suicide inactivation by glycerol and some other substrates (Daniel et al., *FEMS Microbiol. Rev.* 22:553 (1999)). The term "dehydratase reactivation factor" refers to those proteins responsible for reactivating the dehydratase activity. The terms "dehydratase reactivating activity", "reactivating the dehydratase activity", or "regenerating the dehydratase activity" refer to the phenomenon of converting a dehydratase not capable of catalysis of a substrate to one capable of catalysis of a substrate or to the phenomenon of inhibiting the inactivation of a dehydratase or the phenomenon of extending the useful half-life of the dehydratase enzyme in vivo. Two proteins have been identified as being involved as the dehydratase reactiviation factor (see WO 9821341 (U.S. Pat. No. 6,013,494 herein incorporated by reference) and references therein; Daniel et al., supra; Toraya and Mori, *J. Biol. Chem.* 274:3372 (1999); and Tobimatsu et al., *J. Bacteriol.* 181:4110 (1999)).

The terms "oxidoreductase" or "1,3-propanediol oxidoreductase" refer to the polypeptide(s) responsible for an enzyme activity that is capable of catalysing the reduction of 3-hydroxypropionaldehyde to 1,3-propanediol. 1,3-Propanediol oxidoreductase includes, for example, the polypeptide encoded by the dhaT gene (GeneBank U09771, U30903). Alternatively, yqhD, an *E. coli* open reading frame with 40% identity to the gene adhB in *Clostridium* (a probable NADH-dependent butanol dehydratase 2), encodes a polypeptide that functions as a 1,3-propanediol oxidoreductase (WO 0112833).

The enzymes expressed by the pSYCO plasmids (pSYCO101, pSYCO103, pSYCO106, pSYCO109, pSYCO106mcs, and pSYCO109mcs) can all be said to comprise genes required to express glycerol dehydratase, dehydratase reactiviation factor, glycerol-3-phosphate dehydrogenase, and glycerol-3-phosphatase.

The terms "fermentable carbon substrate" and "fermentable carbon source" refer to a carbon source capable of being metabolized by host organisms of the present invention and particularly carbon sources selected from the group consisting of monosaccharides, oligosaccharides, polysaccharides, glycerol, dihydroxyacetone and one-carbon substrates or mixtures thereof.

Gene Expression System with GI Promoter Variants of Differing Strengths

The minimal requirement for an effective gene expression system is the presence of a promoter (a site on DNA where the RNA polymerase binds and begins transcription) upstream from a cloned gene. Often a strong promoter, one that has a high affinity for RNA polymerase, is used with the result that the adjacent downstream region is highly or frequently transcribed.

In the promoter, the main sequence determinant of promoter strength (the level at which the downstream gene is transcribed) is the most highly conserved base pairs. Promoters that have deviations from the conserved sequences have decreased transcription initiation frequency (Hawley, D. K.; McClure, W. R., *Nucleic Acids Res.*, 11:2237-2255 (1983)).

Promoters for *E. coli* RNA polymerase have been shown to contain two regions of conserved DNA sequences, located about 10 and 35 base pairs upstream of the transcription start site. Twelve base pairs were determined to be the most highly conserved among promoters. These bases are TTGACA around 35 base pairs upstream, the so called −35 region, and TATAAT around 10 base pairs upstream, the so called −10 region. Optimum spacing between the −10 and −35 regions is 17 base pairs. The promoter is stronger if the spacing is closer to 17 base pairs; however, promoters with interspacings of 15 and 20 base pairs retain partial function.

Applicants have created a series of constructs incorporating variants of the *Streptomyces lividans* glucose isomerase (GI) promoter. The constructs form a library or kit of promoter variants with a range of different strengths conferring the ability to tailor varying levels of gene expression as needed. The *Streptomyces* glucose isomerase (EC 5.3.1.9) catalyzes the conversion of glucose-6-phosphate to fructose-6-phosphate. Transcription of the gene encoding phosphoglucose isomerase (pgi) is controlled by a promoter that contains a characteristic −10 signature sequence (AATAAT) and a characteristic −35 signature sequence (TTGACA). Although saturation mutagenesis was carried out in the −35 region of the promoter, changes to a SpeI restriction site approximately 122 by upstream from the −35 region also had effects on expressed gene activity. Further, a 25 by deletion between the −10 and the end of this promoter allowed retention of 86% of the enzyme's activity even with the changes to the SpeI restriction site. These particular results had not been previously reported.

Transcription termination of RNA synthesis occurs at specific base sequences on the DNA and regulates termination of transcription. A common termination sequence on the DNA is one containing an inverted repeat with a central non-repeating segment. When such a DNA sequence is transcribed, the RNA can form a stem-loop structure by intrastrand base pairing. When such stem-loop structures in the RNA are followed by runs of uridines, they are effective transcription terminators. Other termination sites are regions where a GC-rich sequence is followed by an AT-rich sequence. Such kinds of structures lead to termination of transcription without adding any extra factors and are sometimes termed intrinsic terminators or rho-independent terminators.

Other types of terminator sequences have been discovered that require protein factors like Rho from *E. coli* in addition to RNA polymerase to function. Rho does not bind to RNA polymerase or to DNA but binds tightly to RNA and moves down the chain towards the RNA polymerase-DNA complex. Once RNA polymerase has paused at a Rho-dependent termination site, Rho can then cause the RNA and polymerase to leave the DNA, thus terminating transcription. Other proteins involved in transcription termination are, like Rho, RNA-binding proteins. In all cases the sequences involved in termination operate at the level of RNA. However, RNA is transcribed from DNA, and so transcription termination is ultimately determined by specific nucleotide sequences on the DNA. (Madigan, M. T.; Martinko, J. M.; Parker, J.; *Brock Biology of Microorganisms*, $8^{th}$ ed., Prentice Hall; Upper Saddle River, N.J. (1997)).

Applicants have constructed a termination region in which three different terminator sequences have been placed in tandem. These three terminators are flanked by unique restriction enzyme sites useful for the cloning of genes or operons. The tonB terminator is a bidirectional rho-independent transcriptional terminator found between the *E. coli* tonB gene and an opposing gene (Postle, K.; Good, R. F., *Cell*, 41, 577-585 (1985)). The thr attenuator, similar in structure to other rho-independent terminators facilitates transcriptional termination of the *E. coli* threonine operon (Yanget et al., *J. Biol. Chem.*, 270:23330-23336 (1995)). The aspA terminator with a structure characteristic of rho-independent terminators, facilitates transcriptional termination of the *E. coli* aspartase operon (Takagi et al., *Nucleic Acid Res.*, 13:2063-2074 (1985)).

As autonomous, self-replicating genetic elements, plasmids have the basic attributes to make them potential vectors for carrying cloned DNA. Naturally-occurring plasmids often lack several important features required in a high-quality cloning vector. These features include (1) a small size (necessary for efficient transfer of exogenous DNA into a host), (2) unique restriction endonuclease recognition sites into which the insert DNA can be cloned, and (3) one or more selectable genetic markers for identifying recipient cells that carry the cloning vector-insert DNA construct. Consequently, plasmid cloning vectors have to be genetically engineered (Glick, B. R., Pasternak, J. J., *Molecular Biotechnology Principles and Applications of Recombinant DNA*, $2^{nd}$ ed., American Society for Microbiology, Washington, D.C. (1998)).

pCL1920/21 vectors are a pair of low-copy-number plasmids that contain a 580 by BstUI fragment carrying the lac promoter/operator, a multiple cloning site and lacZ fragment of pUC19 cloned in place of the polylinker region in pGB2, a pSC101-derived plasmid which confers spectinomycin and streptomycin resistance in *E. coli*. pCL1920/21 vectors (five copies per cell) have a 40-fold difference in plasmid copy number between pCL1920/21 vectors and pUC vectors (200 copies per cell). Thus, the pCL1920/21 vectors allow regulated low-level expression of genes inserted downstream of the promoter-operator when transformed into strains. They should also be useful for cloning genes that may be deleterious at high copy number. Since the pCL1920/21 vectors are compatible with CoIE1-derived plasmids they can be used to form stable co-transformants together with pBR322 or pUC derived plasmids (Lerner et al., *Nucleic Acids Res.*, 18:4631 (1990)).

The plamids of the inventions may be used in a variety of hosts for the controlled bioproduction of materials.
Replacing Chromosomally-Located Native Promoters of any Endogenous Gene or Operon to Alter Transcriptional Level.

Claimed promoter variants (constructs comprising SEQ ID NOs:31 and 32) may be used in a method to replace chromosomally-located native promoters associated with any endogenous gene or operon in order to alter the transcription level of the gene or operon. The result is changed protein production levels. The promoter to be replaced can be any gene in any microorganism where the Llambda red method of Datsenko and Wanner [(2000) PNAS 97:6640-6645] or an equivalent method is operable.

In the method, a chimeric DNA molecule comprising a selectable marker operably linked to a divergently-arranged non-native promoter operably linked to the 5' coding region of a target gene is synthesized by polymerase chain reaction (PCR). The synthesis is accomplished using: (1) a pair of chemically synthesized primers, (a) the first primer comprising: (i) a DNA region distal to the target natural promoter to be replaced, (ii) a non-native promoter, and (iii) a DNA region from either the 3' or 5' end of the selectable marker; and (b) the second primer comprising: (i) a DNA region proximal to the targeted insertion site, and (ii) a DNA region from the opposite end of the selectable marker than was used in the first primer; and (2) a DNA template encoding a selectable marker. This product is integrated in the DNA product synthesized above at the chromosomal target site of any host cell using the method of Datsenko and Wanner (supra). The result of this protocol is that the target native promoter(s) are replaced with the PCR-synthesized chimeric molecule that carries the non-native promoter.

An extension of the method may be used to assess the effect of the varying gene expression level on biocatalyst performance.

Biosynthesis of 1,3-Propanediol (3G) from Glucose in E. Coli

The plasmids of the invention may be used in E. coli for the biosynthesis of 1,3-propanediol (3G) from glucose. The examples herein include the construction of a production organism that incorporates the claimed invention and the genetic machinery necessary to convert a fermentable carbon substrate to 1,3-propanediol.

The genes involved in 1,3-propanediol production include a dehydratase gene (typically a glycerol or diol dehydratase) and an oxidoreductase as well as other proteins expected to aid in the assembly or in maintaining the stability of the dehydratase enzyme. These genes may be transgenes introduced into the host cell, or may be endogenous. At least one of these genes will be a transgene and introduced into the production cell. Recombinant organisms containing the necessary genes that encode the enzymatic pathway to convert a carbon substrate to 1,3-propanediol may be constructed using techniques well known in the art. The transformed production cell is then grown under appropriate conditions for the production of 1,3-propanediol.

Production of 1,3-propanediol in E. coli has been previously described (U.S. Pat. No. 5,633,362; U.S. Pat. No. 5,821,092; U.S. Pat. No. 5,686,276; U.S. Pat. No. 6,025,184; U.S. Pat. No. 6,013,494; U.S. Pat. No. 5,599,689; U.S. Pat. No. 6,136,576). Expression of many different genes are involved in the production from glucose of 1,3-propanediol by a recombinant E. coli. Genes encoding glycerol dehydratase (dhaB) and 1,3-propanediol oxidoreductase (dhaT) were isolated from a native host such as Klebsiella and used to transform host strains such as E. coli strain DH5α or FM5; K. pneumoniae strain ATCC 25955; K. oxytoca strain ATCC 8724 or M5a1, S. cerevisiae strain YPH499, P. pastoris strain GTS115, and A. niger strain FS1.

In Klebsiella pneumonia, Citrobacter freundii, and Clostridium pasteurianum, the genes encoding the three structural subunits of glycerol dehydratase (dhaB1-3 or dhaB, C, and E) are located adjacent to a gene encoding a specific 1,3-propanediol oxidoreductase (dhaT). Although the genetic organization differs somewhat among these microorganisms, these genes are clustered in a group that also includes orfX and orfZ (genes encoding a dehydratase reactivation factor for glycerol dehydratase), as well as orfY and orfW (genes of unknown function). The specific 1,3-propanediol oxidoreductases (dhaT's) of these microorganisms are known to belong to the family of type III alcohol dehydrogenases; each exhibits a conserved iron-binding motif and has a preference for the $NAD^+/NADH$ linked interconversion of 1,3-propanediol and 3-HPA. However, the $NAD^+/NADH$ linked interconversion of 1,3-propanediol and 3-HPA is also catalyzed by alcohol dehydrogenases which are not specifically linked to dehydratase enzymes (for example, horse liver and baker's yeast alcohol dehydrogenases (E.C. 1.1.1.1)), albeit with less efficient kinetic parameters. Glycerol dehydratase (E.C. 4.2.1.30) and diol [1,2-propanediol] dehydratase (E.C. 4.2.1.28) are related but distinct enzymes that are encoded by distinct genes. Diol dehydratase genes from Klebsiella oxytoca and Salmonella typhimurium are similar to glycerol dehydratase genes and are clustered in a group which comprises genes analogous to orfX and orfZ (Daniel et al., FEMS Microbiol. Rev. 22:553 (1999); Toraya and Mori, J. Biol. Chem. 274:3372 (1999); GenBank AF026270).

The gene encoding glycerol-3-phosphate dehydrogenase (DAR1, GPD1) has been cloned and sequenced from S. diastaticus (Wang et al., J. Bact. 176:7091-7095 (1994)). The DAR1 gene was cloned into a shuttle vector and used to transform E. coli where expression produced active enzyme. Wang et al. (supra) recognize that DAR1 is regulated by the cellular osmotic environment but do not suggest how the gene might be used to enhance 1,3-propanediol production in a recombinant microorganism.

Other glycerol-3-phosphate dehydrogenase enzymes have been isolated. For example, sn-glycerol-3-phosphate dehydrogenase has been cloned and sequenced from Saccharomyces cerevisiae (Larason et al., Mol. Microbiol. 10: 1101 (1993)). Albertyn et al. (Mol. Cell. Biol. 14:4135 (1994)) teach the cloning of GPD1 encoding a glycerol-3-phosphate dehydrogenase from Saccharomyces cerevisiae. Like Wang et al. (supra), both Albertyn et al. and Larason et al. recognize the osmo-sensitivity of the regulation of this gene but do not suggest how the gene might be used in the production of 1,3-propanediol in a recombinant microorganism.

As with G3PDH, glycerol-3-phosphatase has been isolated from Saccharomyces cerevisiae and the protein identified as being encoded by the GPP1 and GPP2 genes (Norbeck et al., J. Biol. Chem. 271:13875 (1996)). Like the genes encoding G3PDH, it appears that GPP2 is osmosensitive.

EXAMPLES

The present invention is further defined in the following Examples that indicate preferred embodiments of the invention. From the above discussion and these Examples, one skilled in the art can ascertain the essential characteristics of this invention, and without departing from the spirit and scope thereof, can make various changes and modifications of the invention to adapt it to various uses and conditions.

General Methods

Standard recombinant DNA and molecular cloning techniques used in the Examples are well known in the art and are described by Sambrook, J., Fritsch, E. F. and Maniatis, T. Molecular Cloning: A Laboratory Manual; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg, and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), New England Biolabs (Beverly, Mass.) or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters, "mm" means millimeters, "nm" means nanometers, "mM" means millimolar, "M" means molar, "mmol" means millimole(s), "μmole" mean micromole", "g" means gram, "μg" means microgram.

Example 1

Construction of Glucose Isomerase Promoter Variants

The *Streptomyces lividans* glucose isomerase (GI) promoter (SEQ ID NO:1) contains a characteristic −10 signature sequence (AATAAT) and a characteristic −35 signature sequence (−35 T, −34 T, −33 G, −32 A, −31 C, −30 A). Using mixed base oligonucleotides, saturation mutagenesis of the −35 region of the GI promoter in pMP38 (as described in Example 6 following) was performed by standard PCR. In six individual PCR reactions, an upstream primer (SEQ ID NO:2) was paired with one of six downstream primers (SEQ ID NOs:3-8), each of which contains an equal mixture of all four possible bases at a single position in the −35 region, designated as N. The upstream primer also incorporates two single base pair changes that change a SpeI restriction site (ACTAGT) immediately following the EcoRI site to an AvrII restriction site (CCTAGG). The six PCR products were digested with EcoRI and Hind III, and individually ligated to EcoRI/HindIII digested pMP38. Ligations were transformed into *E. coli*, and recombinant plasmids were identified through restriction analysis by the SpeI to AvrII conversion, and subjected to nucleotide sequencing. Only recombinant plasmids would be expected to harbor possible −35 region changes. Of the twenty-four possible recombinant outcomes (4 bases in 6 positions), 18 were obtained, of which 13 represent changes in the −35 region (Table 1).

TABLE 1

GI promoter variants obtained by saturation mutagenesis PCR

| Position | Base | Name | Comments | SEQ ID NO. |
|---|---|---|---|---|
| −30A | A | P1.6 | No change in −35 region | 9 |
|  | T | P1.5 |  | 10 |
|  | G | P1.20 |  | 11 |
|  | C | P1.10 |  | 12 |
| −31C | C | P2.8 | No change in −35 region | 9 |
|  | A | P2.39 |  | 13 |
| −32A | A | P3.4 | No change in −35 region; 25 bp deletion between −10 and -HindIII site | 14 |
|  | C | P3.5 |  | 15 |
| −33G | G | P4.49 | No change in −35 region | 9 |
|  | A | P4.15 |  | 16 |
|  | C | P4.1 |  | 17 |
| −34T | T | P5.10 | No change in −35 region | 9 |
|  | C | P5.12 |  | 18 |

TABLE 1-continued

GI promoter variants obtained by saturation mutagenesis PCR

| Position | Base | Name | Comments | SEQ ID NO. |
|---|---|---|---|---|
|  | A | P5.17 |  | 19 |
|  | G | P5.19 |  | 20 |
| −35T | T | NA | No change in −35 region | 9 |
|  | G | P6.5 |  | 21 |
|  | A | P6.14 |  | 22 |
|  | C | P6.20 |  | 23 |

*NA = Not Applicable

Although five of the possible 18 changes in the −35 region were not isolated, these may also be useful for varying expression levels of cloned or chromosomally-encoded native and non-native genes or operons. These five additional GI promoter variants are described in Table 2.

TABLE 2

Other Potential GI Promoter Variants

| Position | Base | SEQ ID NO. |
|---|---|---|
| −31C | G | 24 |
|  | T | 25 |
| −32A | G | 26 |
|  | T | 27 |
| −33G | T | 28 |

Example 2

Analysis of Glucose Isomerase Promoter Variants by Measuring Glycerol Dehydratase Activity Glycerol dehydratase (GDH; encoded by dhaB1-3) activity was used as a reporter to measure the effect of the GI promoter mutations (Table 3). It was observed that even in the absence of a change in the −35 region, GDH activity dropped significantly due to the two base pair changes which converted SpeI to AvrII (for example, P1.6). It was also determined that P3.4 did not have a −35 mutation, but did have a 25 base pair deletion immediately following the −10 region, and had nearly wild-type (86%) promoter strength.

Dehydratase activity in cell-free extracts was determined using either glycerol or 1,2-propanediol as substrate. Cell-free extracts were prepared by cell disruption using a French press followed by centrifugation of the cellular debris. The assay, based on the reaction of aldehydes with methylbenzo-2-thiazolone hydrazone, has been described by Forage and Foster (*Biochim. Biophys. Acta* 569:249 (1979)).

TABLE 3

Measure of Relative GDH Activity In GI Promoter Variants

| Plasmid | relative GDH activity |
|---|---|
| pMP38 | 100 |
| pMP38/1.6 | 13 |
| pMP38/1.5 | 3 |
| pMP38/1.20 | 1 |
| pMP38/1.10 | 1 |
| pMP38/2.39 | 0 |
| pMP38/3.4 | 86 |
| pMP38/3.5 | 1 |
| pMP38/4.1 | 0 |
| pMP38/4.15 | 0 |

TABLE 3-continued

Measure of Relative GDH Activity In GI Promoter Variants

| Plasmid | relative GDH activity |
|---|---|
| pMP38/5.12 | 0 |
| pMP38/5.17 | 0 |
| pMP38/5.19 | 0 |
| pMP38/6.5 | 0 |
| pMP38/6.14 | 1 |
| pMP38/6.20 | 2 |

Example 3

Analysis of GI Promoter Variants Using Lux Assays

A second type of reporter was used to measure levels of expression driven from the GI promoter variants. Bacterial bioluminescence is a phenomenon in which the products of 5 structural genes (luxA, luxB, luxC, luxD, and luxE) work in concert to produce light. The luxD product generates a C14 fatty acid from a precursor. The C14 fatty acid is activated in an ATP dependent reaction to an acyl-enzyme conjugate through the action of the luxE product, which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the C14 aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

The *Photorabdus luminenscens* luxAB genes were used as reporters for GI promoter variant strength (Van Dyk et al., *Appl. Environ. Microbiol.*, 180:785-792 (1995)). A PCR fragment carrying the *P. luminenscens* luxAB genes and containing SpeI sites at the 3' and 5' ends and an NcoI site engineered at the initiation codon of luxA was subcloned into the SpeI site in pMCS5 (MobiTec, Gottingen, Germany) yielding pJT13. Then a gene SOEing PCR-based kanamycin cassette with SwaI/NcoI ends was cloned into SwaI/NcoI-digested pJT13 to make pJT14.HIGHCOPY, the high copy luxAB promoter probe. pJT14.HIGHCOPY was then digested with SpeI producing the luxAB::kanamycin cassette, which was subcloned into the unique NheI site (compatible with SpeI), in pRJ50 (SEQ ID NO:79) to make pJT14.LOWCOPY.1, the low copy luxAB promoter probe. The GI promoters 1.6, 1.5, 1.20, and native were cloned into pJT14.HIGHCOPY and pJT14.LOWCOPY as NotI/NcoI fragments to make the high-copy constructs pJT18, pJT19, pJT20, and pJT25, respectively, and low-copy constructs pJT21.1, pJT22.1, pJT23.1, and pJT26.1, respectively. The plasmids were then transformed into select *E. coli* strains for in vivo bioluminescence measurements.

Promoter strengths were measured by luminometry using broth cultures of *E. coli* reporter strains, n-decanal as the aldehyde substrate, and a luminometer, as described by Van Dyk and Rosson (*Methods in Molecular Biology*, Vol. 102: *Bioluminescence Methods and Protocols*, 85 (1998)). *E. coli* clones were inoculated from a fresh agar plate into test tubes containing standard Luria-Bertani liquid growth medium with the appropriate antibiotic and grown aerobically (with shaking) at 37° C. for approximately 16 h. Cells were then subcultured into 100-mL flasks containing 25 mL of fresh medium and grown under the same conditions for approximately 8-10 h. Aliquots (200 µL) were then taken from each culture and placed into 96-well clear and white plates for optical density measurements at 600 nm (SpectraMax 190 Plater Reader, Molecular Devices Corporation, Sunnyvale, Calif.) and luminometer measurements (Luminoscan Ascent TAype 392, LabSystems, Helsinki, Finland), respectively. For the luminometry readings, 2 µL of exogenous aldehyde (n-decanal) was added to each well and measurements made. Results from these assays are listed in Table 4. These luminometry measurements indicated a level of promoter strength similar to that indicated by glycerol dehydratase assays.

TABLE 4

Bioluminescence Measurements

| GI Promoter | Plasmid construct | Relative Bioluminescence |
|---|---|---|
| GI wildtype | pJT26.1 | 100% |
| GI 1.6 | pJT21.1 | 12.9% |
| GI 1.5 | pJT22.1 | 3.0% |
| GI 1.20 | pJT23.1 | 1.3% |

Example 4

Use of Shortened GI Promoter Sequences to Achieve Different Levels of Gene Expression A subset of the GI promoter sequences described and used in Examples 1-3 were used to vary levels of expression of *E. coli* yqhD (SEQ ID NO:29) from the pSYCO109mcs plasmid (as described in Example 8 and SEQ ID NO:30) in strain RJ8n in which the yqhD gene was disrupted on the chromosome to create strain RJ8n (yqhD-).

Three expression cassettes for yqhD were constructed. These cassettes contain (i) one of the shortened GI promoters designated short 1.5 GI (SEQ ID NO:31), short 1.20 GI (SEQ ID NO:32), or short wild-type GI (SEQ ID NO:33); (ii) yqhD from *E. coli* KLP23 (WO9928480); and (iii) the threonine terminator (Lynn et al., *J. Mol. Biol.*, 183:529-541 (1985)). The yqhD gene was isolated by PCR amplification from genomic KLP23 DNA using forward synthetic primers for short 1.5 GI (SEQ ID NO:34), short 1.20 GI (SEQ ID NO:35), or short wild-type GI (SEQ ID NO:36) which contain one of the shortened GI promoters and also incorporate a RsrII restriction site, and the reverse primer for yqhD (SEQ ID NO:37) that contained the threonine terminator and included a SacI site. Plasmid pSYCO109mcs was digested with RsrII/SacI and the RsrII/SacI digested PCR products were ligated into the plasmid. The ligation mixture was transformed into the RJ8n (yqhD-) strain by electroporation and the enzyme activity levels in each of the strains were compared (Table 5.)

The enzyme activity expressed by yqhD will reduce the aldehydes 3-hydroxypropionaldehyde (3-HPA) and butanal with similar rates using NADPH as the source of reducing equivalents. Since 3-HPA is not commercially available, butanal is generally used. The assay mixture contained in 1 mL total volume: 200 mM potassium phosphate buffer (pH 7.5), 10 mM butanal, 0.2 mM NADPH, and approximately 0.01 mg protein from cell-free extracts to be assayed. The initial rate of oxidation of NADPH after addition of protein sample was followed by measuring the change in absorbance at 340 nm ($\Delta\epsilon=6.22$ mM$^{-1}$). A unit of activity is defined as that required to oxidize 1 micromole of NADPH in 1 minute in the presence of 10 mM butanal at 35° C. The activities of various strains are given in Table 5 below and were consistent with levels of expression allowed by the longer GI promoter variants.

TABLE 5

YqhD Activity

| Strain and construct | Activity (U/mg) | % Activity |
|---|---|---|
| RJ8n(yqhD-) | 0.015 | 0.8 |
| RJ8n(yqhD-)/pSYCO109mcs | 0.010 | 0.5 |
| RJ8n(yqhD-)/pSYCO109mcs-short 1.20 GI yqhD | 0.14 | 7.3 |
| RJ8n(yqhD-)/pSYCO109mcs-short 1.5 GI yqhD | 0.29 | 15 |
| RJ8n(yqhD-)/pSYCO109mcs-short wild-type GI yqhD | 1.92 | 100 |

To create RJ8n (yqhD-) the yqhD gene was disrupted in *E. coli* MG1655 using the procedure as described by Wanner and Datsenko (*PNAS*, 97(12):6640-6645 (2000)) for Red-mediated homologous recombination. The forward PCR primer H1::6574 (SEQ ID NO:38) (containing 42 by of sequence homologous to yqhD and the primer binding site P1 to pKD13) and the reverse PCR primer H2::6706 (SEQ ID NO:39) (containing 47 by of homologous yqhD sequence and the primer binding site P4 to pKD13) were prepared. PCR amplification with pKD13 as the template produced a PCR product that had yqhD sequence on each end followed by FRT (FLP recognition target) sites that flank a kanamycin resistance (kanR) marker. The PCR product was electrotransformed into *E. coli* MG1655 cells and kanamycin-resistant transformants were selected. Correct insertion in the transformants was confirmed by PCR using primers yqhDUP (SEQ ID NO:82) and yqhDDN (SEQ ID NO:83) flanking the yqhD gene. The temperature-sensitive plasmid containing the Lambda Red system was cured by growth of the strains at 42° C.

The yqhD::kan disruption was moved into RJ8n by P1 transduction and confirmed by PCR using the yqhDUP2 (SEQ ID NO:40) and yqhDDN2 (SEQ ID NO:41) primers paired with primers internal to the kanR gene (Vec 61; SEQ ID NO:42 and Vec 60; SEQ ID NO:43). To remove the kanamycin marker, integrants were transformed with the temperature-sensitive replicon, pCP20, which contains the gene for the FLP recombinase. FLP recombinase excises the kanamycin marker at the flanking FRT (FLP recognition target) sites. Kanamycin-sensitive cells were then grown at 42° C. to cure pCP20. The resultant strain was RJ8n (yqhD-).

Example 5

Replacement of the *E. coli* Phosphoenolpyruvate Carboxylase Chromosomal Promoter with a GI Promoter Example 5 describes the replacement in the *Escherichia coli* genome of the natural ppc (encoding the phosphoenolpyruvate carboxylase or PEP carboxylase) promoter by the short wild-type GI promoter (SEQ ID NO:33).

Design of the Oligonucleotides for the ppc Promoter Replacement

Two oligonucleotides (ppcF, SEQ ID NO:44 and ppcR, SEQ ID NO:45) were designed to amplify by PCR a cassette containing an 80-bp sequence homologous to the upstream region of the natural ppc promoter, a chloramphenicol-resistance encoding gene (cat) flanked by baker yeast FRT sites, the short wild-type GI promoter sequence (SEQ ID NO:33), and a 40-bp sequence homologous to the downstream region of the +1 transcription start site of the natural ppc promoter.

The ppcR primer (SEQ ID NO:45) is 100 nucleotides long and includes: the entire sequence from the +1 of P1 (natural ppc promoter) transcription start to 41 by upstream the ATG of ppc, the short wild-type GI promoter sequence (SEQ ID NO. 33) from 4 by upstream of the −35 to 9 by downstream of the −10, and the priming site for pKD3 (Wanner and Datsenko, supra), an R6K plasmid containing the cat gene flanked by two FRT sites. The ppcF primer (SEQ ID NO:44) is 100 nucleotides long and includes 80 by of sequence upstream of the natural ppc promoter and the priming site for pKD3.

Primers ppcF and ppcR (SEQ ID NOs:44 and 45) were used to amplify the promoter replacement cassette using plasmid pKD3 as a template. The 1.15-kb PCR product was purified by agarose gel electrophoresis followed by QIAquick gel extraction Kit (Qiagen, Inc., Valencia, Calif.).

Replacement of the Natural ppc Promoter into *Escherichia coli* Genome by Homologous Recombination Using Linear DNA Competent *Escherichia coli* MG1655 cells containing pKD46 (Datsenko and Wanner, supra), a Red-recombinase plasmid expressing γ, β, and exo under the control of the arabinose promoter, were electrotransformed with 0.5 μg of the above 1.15-kb linear DNA and the resulting transformants were screened for chloramphenicol resistance (15 μg/mL). The recombinant strains were checked by PCR using primers ppcF and seqppcR (SEQ ID NO:46). Non-specific integration of the cassette gives no PCR products while true recombinants give a 1.25-kb PCR product. The sequence of the short wild-type GI promoter was confirmed by sequencing the 1.25-kb PCR product with the seqppcR primer (SEQ ID NO:46).

Measurement of Enzymatic Activity

The PEP carboxylase activities in MG1655 and in MG1655 (short wild-type GI-ppc) were measured on ultracentrifuged cell-free extract using the following assay and are indicated in Table 6. The activity of PPC under control of the short wild-type GI promoter was over three times higher than under control of the natural promoter.

The decrease at 340 nm (due to consumption of NADH) was measured in a mixture containing: 0.11 M Tris buffer (pH 8.5), NADH (0.22 mM), Magnesium sulfate (11.1 mM), Sodium bicarbonate (11.1 mM), Acetyl-CoA (0.25 mM), MalateDH (Sigma), 50 μL of 6 U cell extracts and 0.03 Phosphoenolpyruvate (1.11 mM). The following formula was used to determine activity:

$$\text{Units/mg protein} = \frac{\Delta A340/\text{min (test)} - \Delta A340/\text{min (blank)}}{6.22 \times \text{mg protein/mL reaction mixture}}$$

TABLE 6

Activity of PPC from natural and GI1.6 promoters

| Strain | Activity (U/mg) |
|---|---|
| MG1655 | 0.05 |
| MG1655 (1.6GI ppc) | 0.164 |

Example 6

Construction of an Expression Plasmid for use in Transformation of *Escherichia coli* with Genes from the *Kliebsiella pneumoniae* dha Regulon Construction of the Expression Vector pTacIQ:

The *E. coli* expression vector pTacIQ was prepared by inserting the lacI$^Q$ gene (Farabaugh, *Nature*, 274(5673):765-769 (1978)) and tac promoter (Amann et al., *Gene* 25:167-178 (1983)) into the EcoRI site of pBR322 (Sutcliffe, *Cold Spring Harb. Symp. Quant. Biol.* 43:77-90 (1979)). A multiple cloning site and terminator sequence (SEQ ID NO:47) replaced the pBR322 sequence from EcoRI to SphI.

Subcloning the Glycerol Dehydratase Genes (dhaB1, 2, 3, X):

The open reading frame for the dhaB3 gene was amplified from pHK28-26 (SEQ ID NO:48) by PCR using primers (SEQ ID NOs:49-50) incorporating an EcoRI site at the 5' end and a XbaI site at the 3' end. The product was subcloned into pLitmus29 (New England Biolabs) to generate the plasmid pDHAB3 containing dhaB3.

The region (containing the entire coding region for dhaB1, dhaB2, dhaB3, and dhaBX of the dhaB operon from pHK28-26) was cloned into pBluescriptIIKS+ (Stratagene, La Jolla, Calif.) using the restriction enzymes KpnI and EcoRI to create the plasmid pM7.

The dhaBX gene was removed by digesting plasmid pM7 with ApaI and XbaI, purifying the 5.9-kb fragment and ligating it with the 325-bp ApaI-XbaI fragment from plasmid pDHAB3 to create pM11 (containing dhaB1, dhaB2, and dhaB3).

The open reading frame for the dhaB1 gene was amplified from pHK28-26 by PCR using primers (SEQ ID NOs:51-52) incorporating a HindIII site and a consensus ribosome-binding site (RBS) at the 5' end and a XbaI site at the 3' end. The product was subcloned into pLitmus28 (New England Biolabs) to generate the plasmid pDT1 containing dhaB1.

A NotI-XbaI fragment from pM11 (containing part of the dhaB1 gene, the dhaB2 gene, and the dhaB3 gene) was inserted into pDT1 to create the dhaB expression plasmid, pDT2. The HindIII-XbaI fragment (containing the dhaB(1,2,3) genes from pDT2) was inserted into pTacIQ to create pDT3.

Subcloning the 1,3-propanediol Dehydrogenase Gene (dhaT):

The KpnI-SacI fragment of pHK28-26 (containing the 1,3-propanediol dehydrogenase (dhaT) gene) was subcloned into pBluescriptII KS+ creating plasmid pAH1. The dhaT gene was amplified by PCR using pAH1 as template DNA and the synthetic primers (SEQ ID NOs:53-54) which incorporated an XbaI site at the 5' end and a BamHI site at the 3' end. The product was subcloned into pCR-Script (Stratagene) at the SrfI site to generate the plasmids pAH4 and pAH5 containing dhaT. The plasmid pAH4 contains the dhaT gene in the correct orientation for expression from the lac promoter in pCR-Script and pAH5 contains dhaT gene in the opposite orientation. The XbaI-BamHI fragment from pAH4 (containing the dhaT gene) was inserted into pTacIQ to generate plasmid pAH8. The HindII-BamHI fragment from pAH8 (containing the RBS and dhaT gene) was inserted into pBluescriptIIKS+ to create pAH11.

Construction of an Expression Cassette for dhaT and dhaB (1,2,3):

An expression cassette for dhaT and dhaB(1,2,3) was assembled from the individual dhaB(1,2,3) and dhaT subclones described previously using standard molecular biology methods. A SpeI-SacI fragment (containing the dhaB(1, 2,3) genes from pDT3) was inserted into pAH11 at the SpeI-SacI sites to create pAH24. A SalI-XbaI linker created from SEQ ID NOs:55-56 was inserted into pAH5 that was digested with the restriction enzymes SalI-XbaI to create pDT16. The linker destroys the XbaI site. The 1-kb SalI-MluI fragment from pDT16 was then inserted into pAH24 replacing the existing SalI-MluI fragment to create pDT18. pDT21 was constructed by inserting the SalI-NotI fragment from pDT18 and the NotI-XbaI fragment from pM7 into pCL1920 (GenBank AX085428). The glucose isomerase promoter sequence from *Streptomyces lividans* (SEQ ID NO:1) was cloned by PCR and inserted into EcoRI-HindIII sites of pLitmus28 to construct pDT5. pCL1925 was constructed by inserting the EcoRI-PvuII fragment of pDT5 (containing the GI promoter) into the EcoRI-PvuII site of pCL1920 (GenBank AX085428).

Construction of Expression Vector for Glycerol Dehydratase Under the Control of the *Streptomyces glucose* Isomerase Promoter:

The HindIII restriction fragment (containing dhaT) was deleted from pDT24 to generate pRN105. The pDT24 plasmid was constructed by cloning the HindIII-MluI fragment of pDT21 and the MluI-XbaI fragment of pDT21 into the HindIII-XbaI sites of pCL1925. A PCR product (comprising the 3' region of dhaX, from a unique HpaI restriction site to the end of dhaX, and incorporating the HpaI restriction site at the 5' end and an XbaI restriction site at the 3' end) was generated from pRN105 template and used to replace the existing HpaI/XbaI restriction fragment in pRN105, generating pMP37. A PCR product (comprising the 5' region of dhaB1, from a unique HindIII restriction site just upstream of the start codon to a unique NotI restriction site within dhaB1, and incorporating the HindIII restriction site at the 5' end and the NotI restriction site at the 3' end) was generated from pDT29 template and used to replace the small HindIII/NotI restriction fragment in pRN105, generating pRJ25. The pDT29 had been constructed by inserting the SacI-EcoRI fragment of pHK28-26 into SacI-EcoRI sites of pCL1925. The small HpaI/XbaI restriction fragment (containing the 5' region of dhaX from pMP37) was ligated to the large XbaI/HpaI restriction fragment from pRJ25 to generate pMP38, in which the *Streptomyces lividans* glucose isomerase promoter (SEQ ID NO:1) drives expression of the *K. pneumoniae* dhaB1-3,X operon using the native ribosome-binding site.

Example 7

Construction of Syco Plasmids for Production of 1,3-Propanediol

To produce 1,3-propanediol from glucose in an *E. coli* host, several operons from different sources can be expressed. These include genes coding for a glycerol-3-phosphate dehydrogenase, glycerol-3-phosphate phosphatase, and glycerol dehydratase activity. These genes may come from sources such as the dha operon from *Klebsiella pnuemoniae* (containing dhaR, dhaT, dhaX, and dhaB1-3), and the orf operon also from *Klebsiella pnuemoniae* (containing orfYXW), and an operon containing DAR1 and GPP2 from *Saccharomyces*. In order to maintain strain stability in fermentation it is preferable to maintain as few plasmids as possible in the *E. coli* host. To this end a series of plasmids were constructed to enable cloning of at least three different operons on a single plasmid. Three transcriptional terminators were used to flank unique cloning sites in order to prevent read-through of the RNA polymerase. These transcriptional terminators included the tonB terminator, thr attenuator and aspA terminator. The tonB terminator is a bi-directional rho-independent terminator located between the *E. coli* tonB gene and an opposing gene (Postle, K. and Good, R. F., *Cell,* 41:577-585 (1985)). The thr attenuator facilitates transcriptional termination of the *E. coli* threonine operon (Lynn et al., *J. Mol. Biol.,* 183:529-541 (1985)). The aspA terminator facilitates transcriptional termination of the *E. coli* aspartase operon (Takagi et al., *Nucleic Acid Research.* 13(6):2063-2072 (1985)).

Construction of pRJ50 Comprising Three Transcriptional Terminators Flanked by Unique Cloning Sites:

A synthetic DNA fragment (comprising the tonB, thr, and aspA transcriptional terminators (SEQ ID NO:57) and several restriction sites) was assembled using PCR-mediated overlap extension (Horton et al., *BioTechniques,* 8:528-535, (1990)). Two 100 base oligonucleotides (SEQ ID NOs:58-59) that complement each other for a span of 25 base pairs at the 3' ends were annealed to generate a 175-base DNA fragment (SEQ ID NO:60). Two additional oligonucleotide primers (SEQ ID NOs:61-62) were used to further amplify the 175-base fragment, which is flanked by EcoRI and KpnI restriction sites. The 175-base pair PCR product was digested with EcoRI and KpnI and subcloned into EcoRI/KpnI digested plasmid pCL1925 to generate pRJ50 (SEQ ID NO:79).

Construction of an Expression Cassette for dhaR, orfY, orfX, orfW and dhaB(1,2,3,X):

A derivative of plasmid pDT29 was constructed in which all except the first five and the last five codons (plus stop codon) of the gene dhaT were deleted by a technique known as PCR-mediated overlap extension. Using pDT29 as the template, two primary PCR products were generated using the following primers:

```
SEQ ID NO: 63 =
5'GAC GCA ACA GTA TTC CGT CGC3';

SEQ ID NO: 64 =
5'ATG AGC TAT CGT ATG TTC CGC CAG GCA TTC

TGA GTG TTA ACG3';

SEQ ID NO: 65 =
5'GCC TGG CGG AAC ATA CGA TAG CTC ATA ATA

TAC3';

SEQ ID NO: 66 =
5'CGG GGC GCT GGG CCA GTA CTG3'.
```

SEQ ID NO:65 was paired with SEQ ID NO:66 to generate a product of 931 bps and encompassing nucleic acid including 5' dhaB1 (to unique ScaI site), all of orfY, and the first five codons of dhaT. SEQ ID NO:63 was paired with SEQ ID NO:64 to generate a product of 1348 bps and encompassing nucleic acid including the last five codons (plus stop codon) of dhaT, all of orfX, all of orfW, and 5' dhaR (to unique SapI site). The 15 bases at the 5' end of SEQ ID NO:64 constitute a tail that is the inverse complement of a 15-base portion of SEQ ID NO:65. Similarly, the 11 bases at the 5' end of SEQ ID NO:65 constitute a tail that is the inverse complement of an 11-base portion of SEQ ID NO:64. Thus, the two primary PCR products were joined together after annealing (via 26-bp tail overlap) and extending by PCR, to generate a third nucleic acid product of 2253 bps. This third PCR product was digested with SapI and ScaI and ligated into pDT29 which was also digested with SapI and ScaI, to generate the plasmid pKP32, which is identical to pDT29, except for the large, in-frame deletion within dhaT.

Construction of Plasmids for Expression of orfWXY and dhaB1-3 Containing Different GI Promoter Variants:

The orf operon from pKP32 was PCR-amplified (SEQ ID NOs:80-81) with HindIII at the 5' end and AvrII at the 3' end, and subcloned between HindIII and AvrII in pLitmus28 (New England Biolabs) to generate pKP38. The EcoRI/HindIII restriction fragment (containing the GI mutant promoter P1.6 (SEQ ID NO:9) from pMP38/1.6) was subcloned between EcoRI and HindIII in pKP38 to generate pKP39. The AvrII/XbaI restriction fragment (containing the dhaB expression cassette from pMP38/1.6) was subcloned between AvrII and XbaI in pLitmus28 (New England Biolabs) to generate pMP39. The AvrII/XbaI restriction fragment (containing the dhaB expression cassette from pMP39) was subcloned into the AvrII site of pRJ50 to generate pSYCO11. The AvrII restriction fragment (containing the orf expression cassette from pKP39) was subcloned into the NheI site of pSYCO11 to generate pSYCO12. The plasmids pSYCO11 and pSYCO12 are identical except that pSYCO11 does not contain the orf operon.

The EcoRI/HindIII restriction fragment (containing the GI mutant promoter P1.5 (SEQ ID NO:10) from pMP38/1.5) was subcloned between EcoRI and HindIII in pKP38 to generate pKP40. The AvrII restriction fragment (containing the orf operon driven by P1.5 from pKP40) was subcloned into the NheI site of pSYCO11 to generate pSYCO13. The AvrII/NotI restriction fragment (containing the P1.6 and 5' end of dhaB1 in pSYCO13) was replaced with the corresponding AvrII/NotI restriction fragment from pMP38/1.5 to generate pSYCO19.

Construction of pSYCO101, pSYCO103, pSYCO106 and pSYCO109 Vectors with Three Operons Each Isolated by Transcriptional Terminators:

A double-stranded nucleic acid linker (SEQ ID NO:67) was subcloned between the XbaI and SmaI restriction sites in pCL1920 (GenBank AX085428) to generate pCR-pCL1920. The glycerol pathway expression cassette in pAH48 comprising the trc promoter which was derived from pTrc99A (Amersham Pharmacia Biotech, Piscataway, N.J.), the coding sequences for DAR1 and GPP2, of *S. cerevisiae*, and the terminator rrnBT1T2 (from pTrc99A) was PCR-amplified (SEQ ID NOs:68-69) and subcloned into the SrfI restriction site of pCR-pCL1920 to generate pAH105 (SEQ ID NO:70).

The PvuII(2)/PvuII(4) restriction fragment (containing the DAR1/GPP2 expression cassette from pAH105) was subcloned into the Bst1107I site of pSYCO12 to generate pSYCO101 (SEQ ID NO:71). The DAR1/GPP2 operon is in the opposite orientation relative to the orf operon and the dhaB operon. The NheI restriction fragment (containing the DAR1/GPP2 expression cassette from pAH105) was subcloned into the XbaI site of pSYCO19 to generate pSYCO103 (SEQ ID NO:72).

The plasmid pSYCO103 comprises (a) a set of two exogenous genes obtained from *Saccharomyces cerevisiae* (DAR1 (a gene encoding glycerol-3-phosphate dehydrogenase) and GPP2 (a gene encoding glycerol-3-phosphatase)); (b) a set of three exogenous genes obtained from *Klebsiella pneumoniae* (dhaB1 (a gene encoding the "α" subunit of glycerol dehydratase), dhaB2 (a gene encoding the "β" subunit of glycerol dehydratase), and dhaB3 (a gene encoding the "γ" subunit of glycerol dehydratase)); and (c) a set of two exogenous genes obtained from *Klebsiella pneumoniae* (dhaBX (a gene encoding the "α" subunit of dehydratase reactivation factor) and orfX (a gene encoding the "β" subunit of dehydratase reactivation factor)). In pSYCO103 the DAR1/GPP2 operon is in the same orientation relative to the orf operon and the dhaB operon.

The NheI restriction fragment (containing the DAR1/GPP2 expression cassette from pAH105) was subcloned into the XbaI site of pSYCO12 to generate pSYCO106 (SEQ ID NO:73). The DAR1/GPP2 operon is in the same orientation relative to the orf operon and the dhaB operon. The PmlI/NotI restriction fragment in pSYCO106 was removed and replaced with the overlapping StuI/NotI restriction fragment from pSYCO106, resulting in a 141 base pairs deletion near the 3' end of orfW to generate pSYCO109 (SEQ ID NO:74).

Example 8

A Novel Nucleotide Sequence with Ten Rare Restriction Enzyme Sites Useful for Cloning A novel nucleotide sequence was designed to encode ten rare restriction endonuclease sites useful for cloning of additional genes, operons, or cassettes and as sites for transferring cassettes from this plasmid to another. The plasmid pSCYCO106deltaS was constructed by restricting pSYCO106 with SpeI, filling in the ends with Klenow and religating. The pSYCO106deltaS was digested with EcoRI to isolate the vector backbone and then recircularized by ligation to form pSpREPds. Oligonucleotides (SEQ ID NOs:75-76) were annealed at 60° C. and digested with KpnI/StuI. The multiple cloning fragment (SEQ ID NO:77) contains recognition sites for the following enzymes: NheI, RsrII, SacI, AgeI, SnaBI, AscI, PacI, NsiI, MluI, and SapI. The fragments were gel-purified and cloned to pSpREPds to form pSpREPmcs. The pSpREPmcs was linearized with EcoRI and the EcoRI fragments (containing the pathway genes from pSYCO106deltaS and pSYCO109) were ligated to pSpREPmcs to form pSYCO106mcs (SEQ ID NO:78) and pSYCO109mcs (SEQ ID NO: 30), respectively.

Example 9

Production of 1,3-Propanediol Using E. coli Strain RJ8N/PSYCO101

The plasmid pSYCO101 (SEQ ID NO:71) was used to transform electrocompetent E. coli RJ8n cells, resulting in the E. coli strain, RJ8n/pSYCO101.

RJ8n/pSYCO101 was pre-cultured for seeding a fermenter in 2YT medium (10 g/L yeast extract, 16 g/L tryptone, and 10 g/L NaCl) containing 50 mg/L spectinomycin. Cultures were started from frozen stocks (10% glycerol as cryoprotectant) in 500 mL of medium in a 2-L Erlenmeyer flask, grown at 35° C. in a shaker at 250 rpm until an $OD_{550}$ of approximately 1.0 was reached and used to seed the fermenter.

The following components were sterilized together in the fermenter vessel: 45 g $KH_2PO_4$, 12 g citric acid monohydrate, 12 g $MgSO_4.7H_2O$, 30 g yeast extract, 1.8 g ferric ammonium citrate, 5 mL Mazu DF204 as antifoam, 1.2 g $CaCl_2.2H_2O$, 7.2 mL sulfuric acid and 60 mL of a trace element solution. After sterilization, the pH was raised to 6.8 with 20-28% $NH_4OH$ and the following components were added: 0.30 g spectinomycin, and glucose (from a 67 weight % feed). The solution of trace elements contained (g/L): citric acid. $H_2O$ (4.0), $MnSO_4.H_2O$ (3.0), NaCl (1.0), $FeSO_4.7H_2O$ (0.10), $CoCl_2.6H_2O$ (0.10), $ZnSO_4.7H_2O$ (0.10), $CuSO_4.5H_2O$ (0.010), $H_3BO_3$ (0.010), and $Na_2MoO_4.2H_2O$ (0.010). After inoculation, the volume was 6.0 L and the glucose concentration was 10 g/L.

A 15-L stirred tank fermenter was prepared with the medium described above. The temperature was controlled at 34° C. and aqueous ammonia (20-28 weight %) was used to control pH at 6.8. Dissolved oxygen (DO) control was set at 10% and back pressure was controlled at 0.5 bar. Except for minor excursions, glucose was maintained at between 10 g/L and 25 g/L with a 67% (wt) feed. An addition of 10 mg vitamin $B_{12}$ was made at 10 h elapsed fermentation time and a co-feed (2.64 mg/h of a 0.0167 mg/mL solution) begun one hour later. A titer of 99 g/L 1,3-propanediol was obtained after 64 h.

What is claimed is:

1. A DNA construct comprising the short 1.5 GI promoter consisting of SEQ ID NO. 31 operably linked to a nucleic acid sequence encoding a protein or peptide.

2. A transformed host cell comprising the DNA construct of claim 1.

3. The transformed host cell of claim 2 wherein the host cell is RJ8n.

* * * * *

SEQUENCE LISTING

<160> NUMBER OF SEQ ID NOS: 83

<210> SEQ ID NO 1
<211> LENGTH: 199
<212> TYPE: DNA
<213> ORGANISM: artificial sequence
<220> FEATURE:
<223> OTHER INFORMATION: promoter

<400> SEQUENCE: 1
gaattcacta gtcgatctgt gctgtttgcc acggtatgca gcaccagcgc gagattatgg       60
gctcgcacgc tcgactgtcg gacgggggca ctggaacgag aagtcaggcg agccgtcacg      120
cccttgacaa tgccacatcc tgagcaaata attcaaccac taaacaaatc aaccgcgttt      180
cccggaggta accaagctt                                                   199

<210> SEQ ID NO 2
<211> LENGTH: 36
<212> TYPE: DNA
<213> ORGANISM: artificial sequence
<220> FEATURE:
<223> OTHER INFORMATION: primer

<400> SEQUENCE: 2
cgggaattcc ctaggcgatc tgtgctgttt gccacg                                    36

<210> SEQ ID NO 3
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (74)..(74)
<223> OTHER INFORMATION: N = A, T, C, or G

<400> SEQUENCE: 3
cttaagcttg gttacctccg ggaaacgcgg ttgatttgtt tagtggttga attatttgct        60
caggatgtgg catngtcaag ggcg                                                84

<210> SEQ ID NO 4
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (75)..(75)
<223> OTHER INFORMATION: N = A, T, C, or G

<400> SEQUENCE: 4
cttaagcttg gttacctccg ggaaacgcgg ttgatttgtt tagtggttga attatttgct        60
caggatgtgg cattntcaag ggcg                                                84

<210> SEQ ID NO 5
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (76)..(76)
<223> OTHER INFORMATION: N = A, T, C, or G

<400> SEQUENCE: 5
cttaagcttg gttacctccg ggaaacgcgg ttgatttgtt tagtggttga attatttgct        60
caggatgtgg cattgncaag ggcg                                                84

<210> SEQ ID NO 6
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (77)..(77)
<223> OTHER INFORMATION: N = A, T, C, or G

<400> SEQUENCE: 6
cttaagcttg gttacctccg ggaaacgcgg ttgatttgtt tagtggttga attatttgct        60
caggatgtgg cattgtnaag ggcg                                                84

<210> SEQ ID NO 7
<211> LENGTH: 84
<212> TYPE: DNA
<213> ORGANISM: artificial sequence

```
<220> FEATURE:
<223> OTHER INFORMATION: primer
<220> FEATURE:
<221> NAME/KEY: misc_feature
<222> LOCATION: (78)..(78)
<223> OTHER INFORMATION: N = A, T, C, or G

<400> SEQUENCE: 7
cttaagcttg gttacctccg ggaaacgcgg ttgatttgtt tagtggttga attatttgct    60
caggatgtgg cattgtcnag ggcg                                           84

<210> SEQ ID NO 8
<211> LENGTH: 84
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (79)..(79)
<223> OTHER INFORMATION: N = A, T, C, or G

<400> SEQUENCE: 8
cttaagcttg gttacctccg ggaaacgcgg ttgatttgtt tagtggttga attatttgct    60
caggatgtgg cattgtcang ggcg                                           84

<210> SEQ ID NO 9
<211> LENGTH: 187
<212> TYPE: DNA
<213> ORGANISM: artificial sequence
<220> FEATURE:
<223> OTHER INFORMATION: promoter

<400> SEQUENCE: 9
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
acaatgccac atcctgagca ataattcaa ccactaaaca aatcaaccgc gtttcccgga    180
ggtaacc                                                             187

<210> SEQ ID NO 10
<211> LENGTH: 187
<212> TYPE: DNA
<213> ORGANISM: artificial sequence
<220> FEATURE:
<223> OTHER INFORMATION: promoter

<400> SEQUENCE: 10
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
actatgccac atcctgagca ataattcaa ccactaaaca aatcaaccgc gtttcccgga    180
ggtaacc                                                             187

<210> SEQ ID NO 11
<211> LENGTH: 187
<212> TYPE: DNA
<213> ORGANISM: artificial sequence
<220> FEATURE:
<223> OTHER INFORMATION: promoter

<400> SEQUENCE: 11
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
```

```
acgatgccac atcctgagca ataattcaa ccactaaaca atcaaccgc gtttcccgga      180 ggtaacc                                                              187
```

<210> SEQ ID NO 12
<211> LENGTH: 187
<212> TYPE: DNA
<213> ORGANISM: artificial sequence
<220> FEATURE:
<223> OTHER INFORMATION: promoter

<400> SEQUENCE: 12

```
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
accatgccac atcctgagca aataattcaa ccactaaaca aatcaaccgc gtttcccgga   180
ggtaacc                                                             187
```

<210> SEQ ID NO 13
<211> LENGTH: 186
<212> TYPE: DNA
<213> ORGANISM: artificial sequence
<220> FEATURE:
<223> OTHER INFORMATION: promoter

<400> SEQUENCE: 13

```
ctaggcgatc tgtgctgttt gccacggtat gcagcaccag cgcgagatta tgggctcgca    60
cgctcgactg tcggacgggg gcactggaac gagaagtcag gcgagccgtc acgcccttga   120
aaatgccaca tcctgagcaa ataattcaac cactaaacaa atcaaccgcg tttcccggag   180
gtaacc                                                              186
```

<210> SEQ ID NO 14
<211> LENGTH: 162
<212> TYPE: DNA
<213> ORGANISM: artificial sequence
<220> FEATURE:
<223> OTHER INFORMATION: promoter

<400> SEQUENCE: 14

```
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
acaatgccac atcctgagca aataatttc ccggaggtaa cc                       162
```

<210> SEQ ID NO 15
<211> LENGTH: 187
<212> TYPE: DNA
<213> ORGANISM: artificial sequence
<220> FEATURE:
<223> OTHER INFORMATION: promoter

<400> SEQUENCE: 15

```
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg   120
ccaatgccac atcctgagca aataattcaa ccactaaaca aatcaaccgc gtttcccgga   180
ggtaacc                                                             187
```

<210> SEQ ID NO 16
<211> LENGTH: 187
<212> TYPE: DNA
<213> ORGANISM: artificial sequence

```
<220> FEATURE:
<223> OTHER INFORMATION: promoter

<400> SEQUENCE: 16
cctaggcgat ctgtgctgtt tgccacggta tgcagcacca gcgcgagatt atgggctcgc      60
acgctcgact gtcggacggg ggcactggaa cgagaagtca ggcgagccgt cacgccctta     120
acaatgccac atcctgagca aataattcaa ccactaaaca aatcaaccgc gtttcccgga     180
ggtaacc                                                               187

<210> SEQ ID NO 17
<211> LENGTH: 187
<212> TYPE: DNA
<213> ORGANISM: artificial sequence
<220> FEATURE:
<223> OTHER INFORMATION: promoter

<400> SEQUENCE: 17
cctaggcgat ctgtgctgtt tgccacggta tgcagcacca gcgcgagatt atgggctcgc      60
acgctcgact gtcggacggg ggcactggaa cgagaagtca ggcgagccgt cacgcccttc     120
acaatgccac atcctgagca aataattcaa ccactaaaca aatcaaccgc gtttcccgga     180
ggtaacc                                                               187

<210> SEQ ID NO 18
<211> LENGTH: 187
<212> TYPE: DNA
<213> ORGANISM: artificial sequence
<220> FEATURE:
<223> OTHER INFORMATION: promoter

<400> SEQUENCE: 18
cctaggcgat ctgtgctgtt tgccacggta tgcagcacca gcgcgagatt atgggctcgc      60
acgctcgact gtcggacggg ggcactggaa cgagaagtca ggcgagccgt cacgccctcg     120
acaatgccac atcctgagca aataattcaa ccactaaaca aatcaaccgc gtttcccgga     180
ggtaacc                                                               187

<210> SEQ ID NO 19
<211> LENGTH: 187
<212> TYPE: DNA
<213> ORGANISM: artificial sequence
<220> FEATURE:
<223> OTHER INFORMATION: promoter

<400> SEQUENCE: 19
cctaggcgat ctgtgctgtt tgccacggta tgcagcacca gcgcgagatt atgggctcgc      60
acgctcgact gtcggacggg ggcactggaa cgagaagtca ggcgagccgt cacgccctag     120
acaatgccac atcctgagca aataattcaa ccactaaaca aatcaaccgc gtttcccgga     180
ggtaacc                                                               187

<210> SEQ ID NO 20
<211> LENGTH: 187
<212> TYPE: DNA
<213> ORGANISM: artificial sequence
<220> FEATURE:
<223> OTHER INFORMATION: promoter

<400> SEQUENCE: 20
cctaggcgat ctgtgctgtt tgccacggta tgcagcacca gcgcgagatt atgggctcgc      60
acgctcgact gtcggacggg ggcactggaa cgagaagtca ggcgagccgt cacgccctgg     120
```

```
acaatgccac atcctgagca aataattcaa ccactaaaca aatcaaccgc gtttcccgga    180
ggtaacc                                                             187

<210> SEQ ID NO 21
<211> LENGTH: 187
<212> TYPE: DNA
<213> ORGANISM: artificial sequence
<220> FEATURE:
<223> OTHER INFORMATION: promoter

<400> SEQUENCE: 21
cctaggcgat ctgtgctgtt tgccacggta tgcagcacca gcgcgagatt atgggctcgc    60
acgctcgact gtcggacggg ggcactgaa cgagaagtca ggcgagccgt cacgcccgtg     120
acaatgccac atcctgagca aataattcaa ccactaaaca aatcaaccgc gtttcccgga    180
ggtaacc                                                             187

<210> SEQ ID NO 22
<211> LENGTH: 187
<212> TYPE: DNA
<213> ORGANISM: artificial sequence
<220> FEATURE:
<223> OTHER INFORMATION: promoter

<400> SEQUENCE: 22
cctaggcgat ctgtgctgtt tgccacggta tgcagcacca gcgcgagatt atgggctcgc    60
acgctcgact gtcggacggg ggcactgaa cgagaagtca ggcgagccgt cacgcccatg     120
acaatgccac atcctgagca aataattcaa ccactaaaca aatcaaccgc gtttcccgga    180
ggtaacc                                                             187

<210> SEQ ID NO 23
<211> LENGTH: 187
<212> TYPE: DNA
<213> ORGANISM: artificial sequence
<220> FEATURE:
<223> OTHER INFORMATION: promoter

<400> SEQUENCE: 23
cctaggcgat ctgtgctgtt tgccacggta tgcagcacca gcgcgagatt atgggctcgc    60
acgctcgact gtcggacggg ggcactggaa cgagaagtca ggcgagccgt cacgcccctg    120
acaatgccac atcctgagca aataattcaa ccactaaaca aatcaaccgc gtttcccgga    180
ggtaacc                                                             187

<210> SEQ ID NO 24
<211> LENGTH: 187
<212> TYPE: DNA
<213> ORGANISM: artificial sequence
<220> FEATURE:
<223> OTHER INFORMATION: promoter

<400> SEQUENCE: 24
cctaggcgat ctgtgctgtt tgccacggta tgcagcacca gcgcgagatt atgggctcgc    60
acgctcgact gtcggacggg ggcactggaa cgagaagtca ggcgagccgt cacgcccttg    120
agaatgccac atcctgagca aataattcaa ccactaaaca aatcaaccgc gtttcccgga    180
ggtaacc                                                             187

<210> SEQ ID NO 25
<211> LENGTH: 187
```

```
<212> TYPE: DNA
<213> ORGANISM: artificial sequence
<220> FEATURE:
<223> OTHER INFORMATION: promoter

<400> SEQUENCE: 25
cctaggcgat ctgtgctgtt tgccacggta tgcagcacca gcgcgagatt atgggctcgc      60
acgctcgact gtcggacggg ggcactggaa cgagaagtca ggcgagccgt cacgcccttg     120
ataatgccac atcctgagca aataattcaa ccactaaaca aatcaaccgc gtttcccgga     180
ggtaacc                                                              187

<210> SEQ ID NO 26
<211> LENGTH: 187
<212> TYPE: DNA
<213> ORGANISM: artificial sequence
<220> FEATURE:
<223> OTHER INFORMATION: promoter

<400> SEQUENCE: 26
cctaggcgat ctgtgctgtt tgccacggta tgcagcacca gcgcgagatt atgggctcgc      60
acgctcgact gtcggacggg ggcactggaa cgagaagtca ggcgagccgt cacgcccttg     120
gcaatgccac atcctgagca aataattcaa ccactaaaca aatcaaccgc gtttcccgga     180
ggtaacc                                                              187

<210> SEQ ID NO 27
<211> LENGTH: 187
<212> TYPE: DNA
<213> ORGANISM: artificial sequence
<220> FEATURE:
<223> OTHER INFORMATION: promoter

<400> SEQUENCE: 27
cctaggcgat ctgtgctgtt tgccacggta tgcagcacca gcgcgagatt atgggctcgc      60
acgctcgact gtcggacggg ggcactggaa cgagaagtca ggcgagccgt cacgcccttg     120
tcaatgccac atcctgagca aataattcaa ccactaaaca aatcaaccgc gtttcccgga     180
ggtaacc                                                              187

<210> SEQ ID NO 28
<211> LENGTH: 187
<212> TYPE: DNA
<213> ORGANISM: artificial sequence
<220> FEATURE:
<223> OTHER INFORMATION: promoter

<400> SEQUENCE: 28
cctaggcgat ctgtgctgtt tgccacggta tgcagcacca gcgcgagatt atgggctcgc      60
acgctcgact gtcggacggg ggcactggaa cgagaagtca ggcgagccgt cacgcccttt     120
acaatgccac atcctgagca aataattcaa ccactaaaca aatcaaccgc gtttcccgga     180
ggtaacc                                                              187

<210> SEQ ID NO 29
<211> LENGTH: 1164
<212> TYPE: DNA
<213> ORGANISM: Escherichia coli K-12

<400> SEQUENCE: 29
atgaacaact ttaatctgca caccccaacc cgcattctgt ttggtaaagg cgcaatcgct      60
ggtttacgcg aacaaattcc tcacgatgct cgcgtattga ttacctacgg cggcggcagc     120
```

-continued

| | |
|---|---|
| gtgaaaaaaa ccggcgttct cgatcaagtt ctggatgccc tgaaaggcat ggacgtgctg | 180 |
| gaatttggcg gtattgagcc aaacccggct tatgaaacgc tgatgaacgc cgtgaaactg | 240 |
| gttcgcgaac agaaagtgac tttcctgctg gcggttggcg gcggttctgt actggacggc | 300 |
| accaaattta tcgccgcagc ggctaactat ccggaaaata tcgatccgtg gcacattctg | 360 |
| caaacgggcg gtaaagagat taaaagcgcc atcccgatgg gctgtgtgct gacgctgcca | 420 |
| gcaaccggtt cagaatccaa cgcaggcgcg gtgatctccc gtaaaccac aggcgacaag | 480 |
| caggcgttcc attctgccca tgttcagccg gtatttgccg tgctcgatcc ggtttatacc | 540 |
| tacaccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| cgcgccaacg tcatgtgggc ggcgactcag gcgctgaacg gtttgattgg cgctggcgta | 780 |
| ccgcaggact gggcaacgca tatgctgggc cacgaactga ctgcgatgca cggtctggat | 840 |
| cacgcgcaaa cactggctat cgtcctgcct gcactgtgga tgaaaaacg cgataccaag | 900 |
| cgcgctaagc tgctgcaata tgctgaacgc gtctggaaca tcactgaagg ttccgatgat | 960 |
| gagcgtattg acgccgcgat tgccgcaacc cgcaatttct ttgagcaatt aggcgtgccg | 1020 |
| acccacctct ccgactacgg tctggacggc agctccatcc cggctttgct gaaaaaactg | 1080 |
| gaagagcacg gcatgaccca actgggcgaa atcatgaca ttacgttgga tgtcagccgc | 1140 |
| cgtatatacg aagccgcccg ctaa | 1164 |

<210> SEQ ID NO 30
<211> LENGTH: 13470
<212> TYPE: DNA
<213> ORGANISM: artificial sequence
<220> FEATURE:
<223> OTHER INFORMATION: plasmid

<400> SEQUENCE: 30

| | |
|---|---|
| ccttaagtga gtcgtattac ggactggccg tcgttttaca acgtcgtgac tgggaaaacc | 60 |
| ctggcgttac ccaacttaat cgccttgcag cacatccccc tttcgccagc tggcgtaata | 120 |
| gcgaagaggc ccgcaccgat cgcccttccc aacagttgcg cagcctgaat ggcgaatggc | 180 |
| gcctgatgcg gtattttctc cttacgcatc tgtgcggtat ttcacaccgc atatggtgca | 240 |
| ctctcagtac aatctgctct gatgccgcat agttaagcca gccccgacac ccgccaacac | 300 |
| ccgctgacga gcttagtaaa gccctcgcta gattttaatg cggatgttgc gattacttcg | 360 |
| ccaactattg cgataacaag aaaaagccag ccttttcatga tatctcccc aatttgtgta | 420 |
| gggcttatta tgcacgctta aaaataataa aagcagactt gacctgatag tttggctgtg | 480 |
| agcaattatg tgcttagtgc atctaacgct tgagttaagc cgcgccgcga agcggcgtcg | 540 |
| gcttgaacga attgttagac attatttgcc gactaccttg gtgatctcgc ctttcacgta | 600 |
| gtggacaaat tcttccaact gatctgcgcg cgaggccaag cgatcttctt cttgtccaag | 660 |
| ataagcctgt ctagcttcaa gtatgacggg ctgatactgg gccggcaggc gctccattgc | 720 |
| ccagtcggca gcgacatcct tcggcgcgat tttgccggtt actgcgctgt accaaatgcg | 780 |
| ggacaacgta agcactacat ttcgctcatc gccagcccag tcgggcggcg agttccatag | 840 |
| cgttaaggtt tcatttagcg cctcaaatag atcctgttca ggaaccggat caaagagttc | 900 |
| ctccgccgct ggacctacca aggcaacgct atgttctctt gcttttgtca gcaagatagc | 960 |
| cagatcaatg tcgatcgtgg ctggctcgaa gatacctgca agaatgtcat tgcgctgcca | 1020 |

```
ttctccaaat tgcagttcgc gcttagctgg ataacgccac ggaatgatgt cgtcgtgcac    1080
aacaatggtg acttctacag cgcggagaat ctcgctctct ccaggggaag ccgaagtttc    1140
caaaaggtcg ttgatcaaag ctcgccgcgt tgtttcatca agccttacgg tcaccgtaac    1200
cagcaaatca atatcactgt gtggcttcag gccgccatcc actgcggagc cgtacaaatg    1260
tacggccagc aacgtcggtt cgagatggcg ctcgatgacg ccaactacct ctgatagttg    1320
agtcgatact tcggcgatca ccgcttccct catgatgttt aactttgttt tagggcgact    1380
gccctgctgc gtaacatcgt tgctgctcca taacatcaaa catcgaccca cggcgtaacg    1440
cgcttgctgc ttggatgccc gaggcataga ctgtacccca aaaaacagt cataacaagc    1500 catgaaaacc gccactgcgc cgttaccacc gctgcgttcg gtcaaggttc tggaccagtt    1560
gcgtgagcgc atacgctact tgcattacag cttacgaacc gaacaggctt atgtccactg    1620
ggttcgtgcc ttcatccgtt ccacggtgt gcgtcacccg gcaaccttgg gcagcagcga    1680
agtcgaggca tttctgtcct ggctggcgaa cgagcgcaag gtttcggtct ccacgcatcg    1740
tcaggcattg gcggccttgc tgttcttcta cggcaaggtg ctgtgcacgg atctgccctg    1800
gcttcaggag atcggaagac ctcggccgtc gcggcgcttg ccgtggtgc tgaccccgga    1860 tgaagtggtt cgcatcctcg gttttctgga aggcgagcat cgtttgttcg cccagcttct    1920
gtatggaacg ggcatgcgga tcagtgaggg tttgcaactg cgggtcaagg atctggattt    1980
cgatcacggc acgatcatcg tgcgggaggg caagggctcc aaggatcggg ccttgatgtt    2040
acccgagagc ttggcaccca gcctgcgcga gcagggaat taattcccac gggttttgct    2100
gcccgcaaac gggctgttct ggtgttgcta gtttgttatc agaatcgcag atccggcttc    2160
agccggtttg ccggctgaaa gcgctatttc ttccagaatt gccatgattt ttccccacg    2220 ggaggcgtca ctggctcccg tgttgtcggc agctttgatt cgataagcag catcgcctgt    2280
ttcaggctgt ctatgtgtga ctgttgagct gtaacaagtt gtctcaggtg ttcaatttca    2340
tgttctagtt gctttgtttt actggtttca cctgttctat taggtgttac atgctgttca    2400
tctgttacat tgtcgatctg ttcatggtga acagctttga atgcaccaaa aactcgtaaa    2460
agctctgatg tatctatctt ttttacaccg ttttcatctg tgcatatgga cagttttccc    2520
tttgatatgt aacggtgaac agttgttcta cttttgtttg ttagtcttga tgcttcactg    2580
atagatacaa gagccataag aacctcagat ccttccgtat ttagccagta tgttctctag    2640
tgtggttcgt tgtttttgcg tgagccatga gaacgaacca ttgagatcat acttactttg    2700
catgtcactc aaaaattttg cctcaaaact ggtgagctga attttgcag ttaaagcatc    2760 gtgtagtgtt tttcttagtc cgttatgtag gtaggaatct gatgtaatgg ttgttggtat    2820
tttgtcacca ttcattttta tctggttgtt ctcaagttcg gttacgagat ccatttgtct    2880
atctagttca acttggaaaa tcaacgtatc agtcgggcgg cctcgcttat caaccaccaa    2940
tttcatattg ctgtaagtgt ttaaatcttt acttattggt ttcaaaaccc attggttaag    3000
ccttttaaac tcatggtagt tattttcaag cattaacatg aacttaaatt catcaaggct    3060
aatctctata tttgccttgt gagttttctt ttgtgttagt tcttttaata accactcata    3120
aatcctcata gagtatttgt tttcaaaaga cttaacatgt tccagattat attttatgaa    3180 ttttttttaac tggaaaagat aaggcaatat ctcttcacta aaaactaatt ctaatttttc    3240
gcttgagaac ttggcatagt ttgtccactg gaaaatctca agcctttaa ccaaaggatt    3300 cctgatttcc acagttctcg tcatcagctc tctggttgct ttagctaata caccataagc    3360
attttcccta ctgatgttca tcatctgagc gtattggtta taagtgaacg ataccgtccg    3420
```

```
ttctttcctt gtagggtttt caatcgtggg gttgagtagt gccacacagc ataaaattag    3480
cttggtttca tgctccgtta agtcatagcg actaatcgct agttcatttg ctttgaaaac    3540
aactaattca gacatacatc tcaattggtc taggtgattt taatcactat accaattgag    3600
atgggctagt caatgataat tactagctag tccttttcct ttgagttgtg ggtatctgta    3660
aattctgcta gacctttgct ggaaaacttg taaattctgc tagaccctct gtaaattccg    3720 ctagacctttt gtgtgttttt tttgtttata ttcaagtggt tataatttat agaataaaga    3780
aagaataaaa aaagataaaa agaatagatc cagccctgt gtataactca ctactttagt    3840
cagttccgca gtattacaaa aggatgtcgc aaacgctgtt tgctcctcta caaaacagac    3900
cttaaaaccc taaaggctta agtagcaccc tcgcaagctc gggcaaatcg ctgaatattc    3960
cttttgtctc cgaccatcag gcacctgagt cgctgtcttt ttcgtgacat tcagttcgct    4020
gcgctcacgg ctctggcagt gaatgggggt aaatggcact acaggcgcct tttatggatt    4080
catgcaagga aactacccat aatacaagaa agcccgtca cgggcttctc agggcgtttt    4140
atggcgggtc tgctatgtgg tgctatctga ctttttgctg ttcagcagtt cctgccctct    4200
gattttccag tctgaccact tcggattatc ccgtgacagg tcattcagac tggctaatgc    4260
acccagtaag gcagcggtat catcaacagg cttacccgtc ttactgtcgg gaattcattt    4320
aaatagtcaa aagcctccga ccggaggctt ttgactgcta ggcgatctgt gctgtttgcc    4380
acggtatgca gcaccagcgc gagattatgg gctcgcacgc tcgactgtcg gacgggggca    4440
ctggaacgag aagtcaggcg agccgtcacg cccttgacaa tgccacatcc tgagcaaata    4500
attcaaccac taaacaaatc aaccgcgttt cccggaggta accaagcttg cgggagagaa    4560
tgatgaacaa gagccaacaa gttcagacaa tcaccctggc cgccgcccag caaatggcgg    4620
cggcggtgga aaaaaagcc actgagatca acgtggcggt ggtgttttcc gtagttgacc    4680
gcggaggcaa cacgctgctt atccagcgga tggacgagcc cttcgtctcc agctgcgata    4740
tttccctgaa taaagcctgg agcgcctgca gcctgaagca aggtacccat gaaattacgt    4800
cagcggtcca gccaggacaa tctctgtacg gtctgcagct aaccaaccaa cagcgaatta    4860 ttattttttgg cggcggcctg ccagttattt ttaatgagca ggtaattggc gccgtcggcg    4920
ttagcggcgg tacggtcgag caggatcaat tattagccca gtgcgccctg gattgttttt    4980
ccgcattata acctgaagcg agaaggtata ttatgagcta tcgtatgttc cgccaggcat    5040
tctgagtgtt aacagggga ccgtcatgtc gctttcaccg ccaggcgtac gcctgtttta    5100
cgatccgcgc gggcaccatg ccggcgccat caatgagctg tgctggggc tggaggagca    5160 gggggtcccc tgccagacca taacctatga cggaggcgt gacgccgctg cgctgggcgc    5220
cctggcggcc agaagctcgc ccctgcgggt gggtatcggg ctcagcgcgt ccggcgagat    5280
agccctcact catgcccagc tgccggcgga cgcgccgctg gctaccggac acgtcaccga    5340
tagcgacgat caactgcgta cgctcggcgc caacgccggg cagctggtta aagtcctgcc    5400
gttaagtgag agaaactgaa tgtatcgtat ctataccgc accggggata aaggcaccac    5460
cgccctgtac ggcggcagcc gcatcgagaa agaccatatt cgcgtcgagg cctacggcac    5520
cgtcgatgaa ctgatatccc agctgggcgt ctgctacgcc acgacccgcg acgccgggct    5580
gcgggaaagc ctgcaccata ttcagcagac gctgttcgtg ctggggctg aactggccag    5640 cgatgcgcgg ggcctgaccc gcctgagcca gacgatcggc gaagaggaga tcaccgccct    5700
ggagcggctt atcgaccgca atatggccga gagcggcccg ttaaaacagt tcgtgatccc    5760
ggggaggaat ctcgcctctg cccagctgca ccctgatgct tgcgcttgaa ctggcctagc    5820
```

```
aaacacagaa aaaagcccgc acctgacagt gcgggctttt ttttcctag gcgatctgtg   5880 ctgtttgcca cggtatgcag caccagcgcg agattatggg ctcgcacgct cgactgtcgg   5940 acggggcac tggaacgaga agtcaggcga gccgtcacgc ccttgacaat gccacatcct   6000
gagcaaataa ttcaaccact aaacaaatca accgcgtttc ccggaggtaa ccaagcttca   6060
ccttttgagc cgatgaacaa tgaaaagatc aaaacgattt gcagtactgg cccagcgccc   6120
cgtcaatcag gacgggctga ttggcgagtg gcctgaagag gggctgatcg ccatggacag   6180
cccctttgac ccggtctctt cagtaaaagt ggacaacggt ctgatcgtcg aactggacgg   6240
caaacgccgg gaccagtttg acatgatcga ccgatttatc gccgattacg cgatcaacgt   6300
tgagcgcaca gagcaggcaa tgcgcctgga ggcggtggaa atagcccgta tgctggtgga   6360
tattcacgtc agccgggagg agatcattgc catcactacc gccatcacgc cggccaaagc   6420
ggtcgaggtg atggcgcaga tgaacgtggt ggagatgatg atggcgctgc agaagatgcg   6480
tgcccgccgg accccctcca accagtgcca cgtcaccaat ctcaaagata atccggtgca   6540
gattgccgct gacgccgccg aggccgggat ccgcggcttc tcagaacagg agaccacggt   6600
cggtatcgcg cgctacgcgc cgtttaacgc cctggcgctg ttggtcggtt cgcagtgcgg   6660
ccgccccggc gtgttgacgc agtgctcggt ggaagaggcc accgagctgg agctgggcat   6720
gcgtggctta accagctacg ccgagacggt gtcggtctac ggcaccgaag cggtatttac   6780
cgacggcgat gatacgccgt ggtcaaaggc gttcctcgcc tcggcctacg cctcccgcgg   6840
gttgaaaatg cgctacacct ccggcaccgg atccgaagcg ctgatgggct attcggagag   6900
caagtcgatg ctctacctcg aatcgcgctg catcttcatt actaaaggcg ccggggttca   6960
gggactgcaa aacggcgcgg tgagctgtat cggcatgacc ggcgctgtgc cgtcgggcat   7020
tcgggcggtg ctggcggaaa acctgatcgc ctctatgctc gacctcgaag tggcgtccgc   7080
caacgaccag actttctccc actcggatat tcgccgcacc gcgcgcaccc tgatgcagat   7140
gctgccgggc accgacttta ttttctccgg ctacagcgcg gtgccgaact acgacaacat   7200
gttcgccggc tcgaacttcg atgcggaaga ttttgatgat tacaacatcc tgcagcgtga   7260
cctgatggtt gacggcggcc tgcgtccggt gaccgaggcg gaaaccattg ccattcgcca   7320
gaaagcggcg cgggcgatcc aggcggtttt ccgcgagctg gggctgccgc caatcgccga   7380
cgaggaggtg gaggccgcca cctacgcgca cggcagcaac gagatgccgc cgcgtaacgt   7440
ggtggaggat ctgagtgcgg tggaagagat gatgaagcgc aacatcaccg gcctcgatat   7500
tgtcggcgcg ctgagccgca gcggctttga ggatatcgcc agcaatattc tcaatatgct   7560
gcgccagcgg gtcaccggcg attacctgca gacctcggcc attctcgatc ggcagttcga   7620
ggtggtgagt gcggtcaacg acatcaatga ctatcagggg ccgggcaccg gctatcgcat   7680
ctctgccgaa cgctgggcgg agatcaaaaa tattccgggc gtggttcagc ccgacaccat   7740
tgaataaggc ggtattcctg tgcaacagac aacccaaatt cagccctctt ttaccctgaa   7800
aacccgcgag ggcggggtag cttctgccga tgaacgcgcc gatgaagtgg tgatcggcgt   7860
cggccctgcc ttcgataaac accagcatca cactctgatc gatatgcccc atggcgcgat   7920
cctcaaagag ctgattgccg gggtggaaga agagggggctt cacgcccggg tggtgcgcat   7980
tctgcgcacg tccgacgtct cctttatggc ctggatgcg gccaacctga gcggctcggg   8040
gatcggcatc ggtatccagt cgaaggggac cacggtcatc catcagcgcg atctgctgcc   8100
gctcagcaac ctggagctgt tctcccaggc gccgctgctg acgctggaga cctaccggca   8160
gattggcaaa aacgctgcgc gctatgcgcg caaagagtca ccttcgccgg tgccggtggt   8220
```

```
gaacgatcag atggtgcggc cgaaatttat ggccaaagcc gcgctatttc atatcaaaga    8280
gaccaaacat gtggtgcagg acgccgagcc cgtcaccctg cacatcgact tagtaaggga    8340
gtgaccatga gcgagaaaac catgcgcgtg caggattatc cgttagccac ccgctgcccg    8400
gagcatatcc tgacgcctac cggcaaacca ttgaccgata ttaccctcga gaaggtgctc    8460
tctggcgagg tgggcccgca ggatgtgcgg atctcccgcc agacccttga gtaccaggcg    8520
cagattgccg agcagatgca cgccatgcg gtggcgcgca atttccgccg cgcggcggag    8580
cttatcgcca ttcctgacga gcgcattctg gctatctata cgcgctgcg cccgttccgc    8640
tcctcgcagg cggagctgct ggcgatcgcc gacgagctgg agcacacctg gcatgcgaca    8700
gtgaatgccg cctttgtccg ggagtcggcg gaagtgtatc agcagcggca taagctgcgt    8760
aaaggaagct aagcggaggt cagcatgccg ttaatagccg ggattgatat cggcaacgcc    8820
accaccgagg tggcgctggc gtccgactac ccgcaggcga gggcgtttgt tgccagcggg    8880
atcgtcgcga cgacgggcat gaaagggacg cgggacaata tcgccgggac cctcgccgcg    8940
ctggagcagg ccctggcgaa acaccgtgg tcgatgagcg atgtctctcg catctatctt    9000
aacgaagccg cgccggtgat tggcgatgtg gcgatggaga ccatcaccga gaccattatc    9060
accgaatcga ccatgatcgg tcataacccg cagacgccgg gcggggtggg cgttggcgtg    9120
gggacgacta tcgccctcgg gcggctggcg acgctgccgg cggcgcagta tgccgagggg    9180
tggatcgtac tgattgacga cgccgtcgat ttccttgacg ccgtgtggtg gctcaatgag    9240
gcgctcgacc gggggatcaa cgtggtggcg gcgatcctca aaaaggacga cggcgtgctg    9300
gtgaacaacc gcctgcgtaa aaccctgccg gtggtggatg aagtgacgct gctggagcag    9360
gtccccgagg gggtaatggc ggcggtggaa gtggccgcgc cgggccaggt ggtgcggatc    9420
ctgtcgaatc cctacgggat cgccaccttc ttcgggctaa gcccggaaga gacccaggcc    9480
atcgtccca tcgcccgcgc cctgattggc aaccgttccg cggtggtgct caagaccccg    9540
caggggatg tgcagtcgcg ggtgatcccg gcgggcaacc tctacattag cggcgaaaag    9600
cgccgcggag aggccgatgt cgccgagggc gcggaagcca tcatgcaggc gatgagcgcc    9660
tgcgctccgg tacgcgacat ccgcggcgaa ccgggcaccc acgccggcgg catgcttgag    9720
cgggtgcgca aggtaatggc gtccctgacc ggccatgaga tgagcgcgat atacatccag    9780
gatctgctgg cggtggatac gtttattccg cgcaaggtgc agggcgggat ggccggcgag    9840
tgcgccatgg agaatgccgt cgggatggcg gcgatggtga agcggatcg tctgcaaatg    9900
caggttatcg cccgcgaact gagcgcccga ctgcagaccg aggtggtggt gggcggcgtg    9960
gaggccaaca tggccatcgc cggggcgtta accactcccg gctgtgcggc gccgctggcc   10020
atcctcgacc tcgcgccgg ctcgacggat gcggcgatcg tcaacgcgga ggggcagata   10080
acggcggtcc atctcgccgg ggcggggaat atggtcagcc tgttgattaa aaccgagctg   10140
ggcctcgagg atctttcgct ggcggaagcg ataaaaaaat accccgctggc caaagtggaa   10200
agcctgttca gtattcgtca cgagaatggc gcggtggagt tctttcggga agccctcagc   10260
ccggcggtgt tcgccaaagt ggtgtacatc aaggagggca aactggtgcc gatcgataac   10320
gccagcccgc tggaaaaaat tcgtctcgtg cgccggcagg cgaaagagaa agtgtttgtc   10380
accaactgcc tgcgcgcgct cgccaggtc tcacccggg gttccattcg cgatatcgcc   10440
tttgtggtgc tggtgggcgg ctcatcgctg gactttgaga tcccgcagct tatcacggaa   10500
gccttgtcgc actatggcgt ggtcgccggg cagggcaata ttcggggaac agaagggccg   10560
cgcaatgcgg tcgccaccgg gctgctactg gccggtcagg cgaattaaac gggcgctcgc   10620
```

```
gccagcctct aggtacaaat aaaaaaggca cgtcagatga cgtgcctttt ttcttgtcta   10680
gcgtgcacca atgcttctgg cgtcaggcag ccatcggaag ctgtggtatg gctgtgcagg   10740
tcgtaaatca ctgcataatt cgtgtcgctc aaggcgcact cccgttctgg ataatgtttt   10800
ttgcgccgac atcataacgg ttctggcaaa tattctgaaa tgagctgttg acaattaatc   10860
atccggctcg tataatgtgt ggaattgtga gcggataaca atttcacaca ggaaacagac   10920
catgactagt aaggaggaca attccatggc tgctgctgct gatagattaa acttaacttc   10980
cggccacttg aatgctggta gaaagagaag ttcctcttct gtttctttga aggctgccga   11040
aaagcctttc aaggttactg tgattggatc tggtaactgg ggtactacta ttgccaaggt   11100
ggttgccgaa aattgtaagg gatacccaga agttttcgct ccaatagtac aaatgtgggt   11160
gttcgaagaa gagatcaatg gtgaaaaatt gactgaaatc ataaatacta gacatcaaaa   11220
cgtgaaatac ttgcctggca tcactctacc cgacaatttg gttgctaatc cagacttgat   11280
tgattcagtc aaggatgtcg acatcatcgt tttcaacatt ccacatcaat ttttgccccg   11340
tatctgtagc caattgaaag gtcatgttga ttcacacgtc agagctatct cctgtctaaa   11400
gggttttgaa gttggtgcta aaggtgtcca attgctatcc tcttacatca ctgaggaact   11460
aggtattcaa tgtggtgctc tatctggtgc taacattgcc accgaagtcg ctcaagaaca   11520
ctggtctgaa acaacagttg cttaccacat tccaaaggat ttcagaggcg agggcaagga   11580
cgtcgaccat aaggttctaa aggccttgtt ccacagacct tacttccacg ttagtgtcat   11640
cgaagatgtt gctggtatct ccatctgtgg tgctttgaag aacgttgttg ccttaggttg   11700
tggtttcgtc gaaggtctag gctggggtaa caacgcttct gctgccatcc aaagagtcgg   11760
tttgggtgag atcatcagat tcggtcaaat gttttttccca gaatctagag aagaaacata   11820
ctaccaagag tctgctggtg ttgctgattt gatcaccacc tgcgctggtg gtagaaacgt   11880
caaggttgct aggctaatgg ctacttctgg taaggacgcc tgggaatgtg aaaaggagtt   11940
gttgaatggc caatccgctc aaggtttaat tacctgcaaa gaagttcacg aatggttgga   12000
aacatgtggc tctgtcgaag acttcccatt atttgaagcc gtataccaaa tcgtttacaa   12060
caactaccca atgaagaacc tgccggacat gattgaagaa ttagatctac atgaagatta   12120
gatttattgg atccaggaaa cagactagaa ttatgggatt gactactaaa cctctatctt   12180
tgaaagttaa cgccgctttg ttcgacgtcg acggtaccat tatcatctct caaccagcca   12240
ttgctgcatt ctggagggat ttcggtaagg acaaacctta tttcgatgct gaacacgtta   12300
tccaagtctc gcatggttgg agaacgtttg atgccattgc taagttcgct ccagactttg   12360
ccaatgaaga gtatgttaac aaattagaag ctgaaattcc ggtcaagtac ggtgaaaaat   12420
ccattgaagt cccaggtgca gttaagctgt gcaacgcttt gaacgctcta ccaaaagaga   12480
aatgggctgt ggcaacttcc ggtacccgtg atatggcaca aaaatggttc gagcatctgg   12540
gaatcaggag accaaagtac ttcattaccg ctaatgatgt caaacagggt aagcctcatc   12600
cagaaccata tctgaagggc aggaatggct taggatatcc gatcaatgag caagaccctt   12660
ccaaatctaa ggtagtagta tttgaagacg ctccagcagg tattgccgcc ggaaaagccg   12720
ccggttgtaa gatcattggt attgccacta ctttcgactt ggacttccta aaggaaaaag   12780
gctgtgacat cattgtcaaa aaccacgaat ccatcagagt tggcggctac aatgccgaaa   12840
cagacgaagt tgaattcatt tttgacgact acttatatgc taaggacgat ctgttgaaat   12900
ggtaacccgg gctgcaggca tgcaagcttg gctgttttgg cggatgagag aagattttca   12960
gcctgataca gattaaatca gaacgcagaa gcggtctgat aaaacagaat ttgcctggcg   13020
```

-continued

```
gcagtagcgc ggtggtccca cctgacccca tgccgaactc agaagtgaaa cgccgtagcg    13080
ccgatggtag tgtggggtct ccccatgcga gagtagggaa ctgccaggca tcaaataaaa    13140
cgaaaggctc agtcgaaaga ctgggccttt cgttttatct gttgtttgtc ggtgaacgct    13200
ctcctgagta ggacaaatcc gccggagcg gatttgaacg ttgcgaagca acggcccgga     13260
gggtggcggg caggacgccc gccataaact gccaggcatc aaattaagca gaaggccatc    13320
ctgacggatg ccttttgc gtttctacaa actccagctg gatcgggcgc tagagtatac      13380
atttaaatgg taccggcgcg ccgctagctt aattaacgga ccgatgcatg agctcacgcg    13440
taccggtgct cttcgatcta cgtaagaagg                                     13470
```

<210> SEQ ID NO 31
<211> LENGTH: 42
<212> TYPE: DNA
<213> ORGANISM: artificial sequence
<220> FEATURE:
<223> OTHER INFORMATION: promoter

<400> SEQUENCE: 31

```
gcccttgact atgccacatc ctgagcaaat aattcaacca ct                       42
```

<210> SEQ ID NO 32
<211> LENGTH: 42
<212> TYPE: DNA
<213> ORGANISM: artificial sequence
<220> FEATURE:
<223> OTHER INFORMATION: promoter

<400> SEQUENCE: 32

```
gcccttgacg atgccacatc ctgagcaaat aattcaacca ct                       42
```

<210> SEQ ID NO 33
<211> LENGTH: 42
<212> TYPE: DNA
<213> ORGANISM: artificial sequence
<220> FEATURE:
<223> OTHER INFORMATION: promoter

<400> SEQUENCE: 33

```
gcccttgaca atgccacatc ctgagcaaat aattcaacca ct                       42
```

<210> SEQ ID NO 34
<211> LENGTH: 81
<212> TYPE: DNA
<213> ORGANISM: artificial sequence
<220> FEATURE:
<223> OTHER INFORMATION: primer

<400> SEQUENCE: 34

```
cattcggacc ggcccttgac tatgccacat cctgagcaaa taattcaacc actacagcaa    60
agggagcaag taatgaacaa c                                              81
```

<210> SEQ ID NO 35
<211> LENGTH: 81
<212> TYPE: DNA
<213> ORGANISM: artificial sequence
<220> FEATURE:
<223> OTHER INFORMATION: primer

<400> SEQUENCE: 35

```
cattcggacc ggcccttgac gatgccacat cctgagcaaa taattcaacc actacagcaa    60
agggagcaag taatgaacaa c                                              81
```

<210> SEQ ID NO 36
<211> LENGTH: 81
<212> TYPE: DNA
<213> ORGANISM: artificial sequence
<220> FEATURE:
<223> OTHER INFORMATION: primer

<400> SEQUENCE: 36
cattcggacc ggcccttgac aatgccacat cctgagcaaa taattcaacc actacagcaa    60
agggagcaag taatgaacaa c                                              81

<210> SEQ ID NO 37
<211> LENGTH: 82
<212> TYPE: DNA
<213> ORGANISM: artificial sequence
<220> FEATURE:
<223> OTHER INFORMATION: primer

<400> SEQUENCE: 37
cattgagctc aaaaaaaaag cccgcactgt caggtgcggg cttttttctg tgtttaagct    60
tagcgggcgg cttcgtatat ac                                             82

<210> SEQ ID NO 38
<211> LENGTH: 62
<212> TYPE: DNA
<213> ORGANISM: artificial sequence
<220> FEATURE:
<223> OTHER INFORMATION: primer

<400> SEQUENCE: 38
atgtgcgcgc caacgtcatg tgggcggcga ctcaggcgct gagtgtaggc tggagctgct    60
tc                                                                   62

<210> SEQ ID NO 39
<211> LENGTH: 67
<212> TYPE: DNA
<213> ORGANISM: artificial sequence
<220> FEATURE:
<223> OTHER INFORMATION: primer

<400> SEQUENCE: 39
cagacgcgtt cagcatattg cagcagctta gcgcgcttgg tatcgcgatt ccggggatcc    60
gtcgacc                                                              67

<210> SEQ ID NO 40
<211> LENGTH: 25
<212> TYPE: DNA
<213> ORGANISM: artificial sequence
<220> FEATURE:
<223> OTHER INFORMATION: primer

<400> SEQUENCE: 40
gccagcaagc ggcaaatctc ttcac                                          25

<210> SEQ ID NO 41
<211> LENGTH: 25
<212> TYPE: DNA
<213> ORGANISM: artificial sequence
<220> FEATURE:
<223> OTHER INFORMATION: primer

<400> SEQUENCE: 41
gaggcgtaaa aagcttagcg ggcgg                                          25

```
<210> SEQ ID NO 42
<211> LENGTH: 24
<212> TYPE: DNA
<213> ORGANISM: artificial sequence
<220> FEATURE:
<223> OTHER INFORMATION: primer

<400> SEQUENCE: 42
gcttcctcgt gctttacggt atcg                                           24

<210> SEQ ID NO 43
<211> LENGTH: 23
<212> TYPE: DNA
<213> ORGANISM: artificial sequence
<220> FEATURE:
<223> OTHER INFORMATION: primer

<400> SEQUENCE: 43
cctgcgtgca atccatcttg ttc                                            23

<210> SEQ ID NO 44
<211> LENGTH: 100
<212> TYPE: DNA
<213> ORGANISM: artificial sequence
<220> FEATURE:
<223> OTHER INFORMATION: primer

<400> SEQUENCE: 44
cgatttttta acatttccat aagttacgct tatttaaagc gtcgtgaatt taatgacgta    60
aattcctgct atttattcgt gtgtaggctg gagctgcttc                         100

<210> SEQ ID NO 45
<211> LENGTH: 100
<212> TYPE: DNA
<213> ORGANISM: artificial sequence
<220> FEATURE:
<223> OTHER INFORMATION: primer

<400> SEQUENCE: 45
tcgcattggc gcgaatatgc tcgggctttg cttttcgtca gtggttgaat tatttgctca    60
ggatgtggca ttgtcaaggg catatgaata tcctccttag                         100

<210> SEQ ID NO 46
<211> LENGTH: 30
<212> TYPE: DNA
<213> ORGANISM: artificial sequence
<220> FEATURE:
<223> OTHER INFORMATION: primer

<400> SEQUENCE: 46
gcggaatatt gttcgttcat attaccccag                                     30

<210> SEQ ID NO 47
<211> LENGTH: 94
<212> TYPE: DNA
<213> ORGANISM: artificial sequence
<220> FEATURE:
<223> OTHER INFORMATION: terminator

<400> SEQUENCE: 47
agcttaggag tctagaatat tgagctcgaa ttcccgggca tgcggtaccg gatccagaaa    60
aaagcccgca cctgacagtg cgggcttttt tttt                                94
```

```
<210> SEQ ID NO 48
<211> LENGTH: 12145
<212> TYPE: DNA
<213> ORGANISM: artificial sequence
<220> FEATURE:
<223> OTHER INFORMATION: plasmid

<400> SEQUENCE: 48
gtcgaccacc acggtggtga ctttaatgcc gctctcatgc agcagctcgg tggcggtctc      60
aaaattcagg atgtcgccgg tatagttttt gataatcagc aagacgcctt cgccgccgtc     120
aatttgcatc gcgcattcaa acattttgtc cggcgtcggc gaggtgaata tttcccccgg     180
acaggcgccg gagagcatgc cctggccgat atagccgcag tgcatcggtt catgtccgct     240
gccgccgccg gagagcaggg ccaccttgcc agccaccggc gcgtcggtgc gggtcacata     300
cagcgggtcc tgatgcaggg tcagctgcgg atgggcttta gccagcccct gtaattgttc     360
attcagtaca tcttcaacac ggttaatcag ctttttcatt attcagtgct ccgttggaga     420
aggttcgatg ccgcctctct gctggcgagg cggtcatcg cgtaggggta tcgtctgacg      480
gtggagcgtg cctggcgata tgatgattct ggctgagcgg acgaaaaaaa gaatgccccg     540
acgatcgggt ttcattacga acattgctt cctgattttg tttctttatg gaacgttttt      600
gctgaggata tggtgaaaat gcgagctggc gcgcttttt tcttctgcca taagcggcgg      660
tcaggatagc cggcgaagcg ggtgggaaaa aattttttgc tgattttctg ccgactgcgg     720
gagaaaaggc ggtcaaacac ggaggattgt aagggcatta tgcggcaaag gagcggatcg     780
ggatcgcaat cctgacagag actagggttt tttgttccaa tatggaacgt aaaaaattaa     840
cctgtgtttc atatcagaac aaaaaggcga agatttttt tgttccctgc cggccctaca      900
gtgatcgcac tgctccggta cgctccgttc aggccgcgct tcactggccg gcgcggataa     960
cgccagggct catcatgtct acatgcgcac ttatttgagg gtgaaaggaa tgctaaaagt    1020
tattcaatct ccagccaaat atcttcaggg tcctgatgct gctgttctgt tcggtcaata    1080
tgccaaaaac ctggcggaga gcttcttcgt catcgctgac gatttcgtaa tgaagctggc    1140
gggagagaaa gtggtgaatg gcctgcagag ccacgatatt cgctgccatg cggaacggtt    1200
taacggcgaa tgcagccatg cggaaatcaa ccgtctgatg gcgattttgc aaaaacaggg    1260
ctgccgcggc gtggtcggga tcggcggtgg taaaaccctc gataccgcga aggcgatcgg    1320
ttactaccag aagctgccgg tggtggtgat cccgaccatc gcctcgaccg atgcgccaac    1380
cagcgcgctg tcggtgatct acaccgaagc gggcgagttt gaagagtatc tgatctatcc    1440
gaaaaacccg gatatggtgg tgatggacac ggcgattatc gccaaagcgc cggtacgcct    1500
gctggtctcc ggcatgggcg atgcgctctc cacctggttc gaggccaaag cttgctacga    1560
tgcgcgcgcc accagcatgg ccggaggaca gtccaccgag gcggcgctga gcctcgcccg    1620
cctgtgctat gatacgctgc tggcggaggg cgaaaaggcc cgtctggcgg cgcaggccgg    1680
ggtagtgacc gaagcgctgg agcgcatcat cgaggcgaac acttacctca gcggcattgg    1740
ctttgaaagc agtggcctgg ccgctgccca tgcaatccac aacggtttca ccattcttga    1800
agagtgccat cacctgtatc acggtgagaa agtggccttc ggtaccctgg cgcagctggt    1860
gctgcagaac agcccgatgg acgagattga acggtgcag gcttctgcc agcgcgtcgg      1920 cctgccggtg acgtcgcgc agatgggcgt caaagagggg atcgacgaga aaatcgccgc    1980
ggtggcgaaa gctacctgcg cggaagggga aaccatccat aatatgccgt ttgcggtgac    2040
cccggagagc gtccatgccg ctatcctcac cgccgatctg ttaggccagc agtggctggc    2100
gcgttaattc gcggtggcta aaccgctggc ccaggtcagc ggttttctt tctcccctcc     2160
```

```
ggcagtcgct gccggagggg ttctctatgg tacaacgcgg aaaaggatat gactgttcag   2220
actcaggata ccgggaaggc ggtctcttcc gtcattgccc agtcatggca ccgctgcagc   2280
aagtttatgc agcgcgaaac ctggcaaacg ccgcaccagg cccagggcct gaccttcgac   2340
tccatctgtc ggcgtaaaac cgcgctgctc accatcggcc aggcggcgct ggaagacgcc   2400
tgggagttta tggacggccg cccctgcgcg ctgtttattc ttgatgagtc cgcctgcatc   2460
ctgagccgtt gcggcgagcc gcaaaccctg gcccagctgg ctgccctggg atttcgcgac   2520
ggcagctatt gtgcggagag cattatcggc acctgcgcgc tgtcgctggc cgcgatgcag   2580
ggccagccga tcaacaccgc cggcgatcgg cattttaagc aggcgctaca gccatggagt   2640
ttttgctcga cgccggtgtt tgataaccac gggcggctgt tcggctctat ctcgctttgc   2700
tgtctggtcg agcaccagtc cagcgccgac ctctccctga cgctggccat cgcccgcgag   2760
gtgggtaact ccctgcttac cgacagcctg ctggcggaat ccaaccgtca cctcaatcag   2820
atgtacggcc tgctggagag catggacgat ggggtgatgg cgtggaacga acagggcgtg   2880
ctgcagtttc tcaatgttca ggcggcgaga ctgctgcatc ttgatgctca ggccagccag   2940
gggaaaaata tcgccgatct ggtgaccctc ccggcgctgc tgcgccgcgc catcaaacac   3000
gccccgcggcc tgaatcacgt cgaagtcacc tttgaaagtc agcatcagtt tgtcgatgcg   3060
gtgatcacct taaaaccgat tgtcgaggcg caaggcaaca gttttattct gctgctgcat   3120
ccggtggagc agatgcggca gctgatgacc agccagctcg gtaaagtcag ccacaccttt   3180
gagcagatgt ctgccgacga tccggaaacc cgacgcctga tccactttgg ccgccaggcg   3240
gcgcgcggcg gcttcccggt gctactgtgc ggcgaagagg gggtcgggaa agagctgctg   3300
agccaggcta ttcacaatga aagcgaacgg cgggcggcc cctacatctc cgtcaactgc   3360
cagctatatg ccgacagcgt gctgggccag gactttatgg gcagcgcccc taccgacgat   3420
gaaaatggtc gcctgagccg ccttgagctg gccaacggcg gcaccctgtt tctggaaaag   3480
atcgagtatc tggcgccgga gctgcagtcg gctctgctgc aggtgattaa gcagggcgtg   3540
ctcacccgcc tcgacgcccg gcgcctgatc ccggtggatg tgaaggtgat tgccaccacc   3600
accgtcgatc tggccaatct ggtggaacag aaccgcttta gccgccagct gtactatgcg   3660
ctgcactcct ttgagatcgt catcccgccg ctgcgcgccc gacgcaacag tattccgtcg   3720
ctggtgcata accggttgaa gagcctggag aagcgtttct cttcgcgact gaaagtggac   3780
gatgacgcgc tggcacagct ggtggcctac tcgtggccgg ggaatgattt tgagctcaac   3840
agcgtcattg agaatatcgc catcagcagc gacaacggcc acattcgcct gagtaatctg   3900
ccggaatatc tcttttccga gcggccgggc ggggatagcg cgtcatcgct gctgccggcc   3960
agcctgactt ttagcgccat cgaaaaggaa gctattattc acgccgcccg ggtgaccagc   4020
gggcgggtgc aggagatgtc gcagctgctc aatatcggcc gcaccaccct gtggcgcaaa   4080
atgaagcagt acgatattga cgccagccag ttcaagcgca agcatcaggc ctagtctctt   4140
cgattcgcgc catggagaac agggcatccg acaggcgatt gctgtagcgt ttgagcgcgt   4200
cgcgcagcgg atgcgcgcgg tccatggccg tcagcaggcg ttcgagccga cgggactggg   4260
tgcgcgccac gtgcagctgg gcagaggcga gattcctccc cgggatcacg aactgtttta   4320
acgggccgct ctcggccata ttgcggtcga taagccgctc cagggcggtg atctcctctt   4380
cgccgatcgt ctggctcagg cgggtcaggc cccgcgcatc gctggccagt tcagccccca   4440
gcacgaacag cgtctgctga atatggtgca ggctttcccg cagcccggcg tcgcgggtcg   4500
tggcgtagca gacgcccagc tgggatatca gttcatcgac ggtgccgtag gcctcgacgc   4560
```

```
gaatatggtc tttctcgatg cggctgccgc cgtacagggc ggtggtgcct ttatccccgg    4620
tgcgggtata gatacgatac attcagtttc tctcacttaa cggcaggact ttaaccagct    4680
gcccggcgtt ggcgccgagc gtacgcagtt gatcgtcgct atcggtgacg tgtccggtag    4740
ccagcggcgc gtccgccggc agctgggcat gagtgagggc tatctcgccg gacgcgctga    4800
gcccgatacc caccgcaggg gcgagcttc tggccgccag ggcgcccagc gcagcggcgt     4860
caccgcctcc gtcataggtt atggtctggc aggggacccc ctgctcctcc agcccccagc    4920
acagctcatt gatggcgccg gcatggtgcc cgcgcggatc gtaaaacagg cgtacgcctg    4980
gcggtgaaag cgacatgacg gtcccctcgt taacactcag aatgcctggc ggaaaatcgc    5040
ggcaatctcc tgctcgttgc ctttacgcgg gttcgagaac gcattgccgt cttttagagc    5100
catctccgcc atgtagggga agtcggcctc ttttaccccc agatcgcgca gatgctgcgg    5160
aataccgata tccatcgaca gacgcgtgat agcggcgatg cttttttccg ccgcgtcgag    5220
agtggacagt ccggtgatat tttcgcccat cagttcagcg atatcggcga atttctccgg    5280
gttggcgatc aggttgtagc gcgccacatg cggcagcagg acagcgttgg ccacgccgtg    5340
cggcatgtcg tacaggccgc ccagctggtg cgccatggcc tgcacgtagc cgaggttggc    5400
gttattgaaa gccatcccgg ccagcagaga agcataggcc atgttttccc gcgcctgcag    5460
attgctgccg agggccacgg cctggcgcag gttgcgggcg atgaggcgga tcgcctgcat    5520
ggcggcggcg tccgtcaccg ggttagcgtc tttggagata taggcctcta cggcgtgggt    5580
cagggcatcc atcccggtcg ccgcggtcag ggcggccggt ttaccgatca tcagcagtgg    5640
atcgttgata gagaccgacg gcagtttgcg ccagctgacg atcacaaact tcactttggt    5700
ttcggtgttg gtcaggacgc agtggcgggt gacctcgctg gcggtgccgg cggtggtatt    5760
gaccgcgacg ataggcggca gcgggttggt cagggtctcg attccggcat actggtacag    5820
atcgccctca tgggtggcgg cgatgccgat gcctttgccg caatcgtgcg ggctgccgcc    5880
gcccacggtg acgatgatgt cgcactgttc gcggcgaaac acggcgaggc cgtcgcgcac    5940
gttggtgtct ttcgggttcg gctcgacgcc gtcaaagatc gccacctcga tcccggcctc    6000
ccgcagataa tgcagggttt tgtccaccgc gccatcttta attgcccgca ggcctttgtc    6060
ggtgaccagc agggcttttt tccccccag cagctggcag cgttcgccga ctacggaaat     6120
ggcgttgggg ccaaaaaagt taacgtttgg caccagataa tcaaacatac gatagctcat    6180
aatataccTT ctcgcttcag gttataatgc ggaaaaacaa tccagggcgc actgggctaa    6240
taattgatcc tgctcgaccg taccgccgct aacgccgacg gcgccaatta cctgctcatt    6300
aaaaataact ggcaggccgc cgccaaaaat aataattcgc tgttggttgg ttagctgcag    6360
accgtacaga gattgtcctg gctggaccgc tgacgtaatt tcatgggtac cttgcttcag    6420
gctgcaggcg ctccaggctt tattcaggga aatatcgcag ctggagacga aggcctcgtc    6480
catccgctgg ataagcagcg tgttgcctcc gcggtcaact acgaaaaaca ccaccgccac    6540
gttgatctca gtggcttttt tttccaccgc cgccgccatt tgctgggcgg cggccagggt    6600
gattgtctga acttgttggc tcttgttcat cattctctcc cgcaccagga taacgctggc    6660
gcgaatagtc agtaggggc gatagtaaaa aactattacc attcggttgg cttgctttat     6720
ttttgtcagc gttattttgt cgcccgccat gatttagtca ataggttaa aatagcgtcg      6780 gaaaaacgta attaagggcg ttttttatta attgatttat atcattgcgg gcgatcacat    6840
ttttTATTTT tgccgccgga gtaaagtttc atagtgaaac tgtcggtaga tttcgtgtgc    6900
caaattgaaa cgaaattaaa tttattttTT tcaccactgg ctcatttaaa gttccgctat    6960
```

```
tgccggtaat ggccgggcgg caacgacgct ggcccggcgt attcgctacc gtctgcggat   7020 ttcaccttt gagccgatga caatgaaaa gatcaaaacg atttgcagta ctggcccagc     7080
gccccgtcaa tcaggacggg ctgattggcg agtggcctga agaggggctg atcgccatgg   7140 acagccctt tgacccggtc tcttcagtaa aagtggacaa cggtctgatc gtcgaactgg    7200
acggcaaacg ccgggaccag tttgacatga tcgaccgatt tatcgccgat tacgcgatca   7260
acgttgagcg cacagagcag gcaatgcgcc tggaggcggt ggaaatagcc cgtatgctgg   7320
tggatattca cgtcagccgg gaggagatca ttgccatcac taccgccatc acgccggcca   7380
aagcggtcga ggtgatggcg cagatgaacg tggtggagat gatgatggcg ctgcagaaga   7440
tgcgtgcccg ccggaccccc tccaaccagt gccacgtcac caatctcaaa gataatccgg   7500
tgcagattgc cgctgacgcc gccgaggccg ggatccgcgg cttctcagaa caggagacca   7560
cggtcggtat cgcgcgctac gcgccgttta acgccctggc gctgttggtc ggttcgcagt   7620
gcggccgccc cggcgtgttg acgcagtgct cggtggaaga ggccaccgag ctggagctgg   7680
gcatgcgtgg cttaaccagc tacgccgaga cggtgtcggt ctacggcacc gaagcggtat   7740
ttaccgacgc gatgatacg ccgtggtcaa aggcgttcct cgcctcggcc tacgcctccc    7800
gcgggttgaa aatgcgctac acctccggca ccggatccga agcgctgatg ggctattcgg   7860
agagcaagtc gatgctctac ctcgaatcgc gctgcatctt cattactaaa ggcgccgggg   7920
ttcagggact gcaaaacggc gcggtgagct gtatcggcat gaccggcgct gtgccgtcgg   7980
gcattcgggc ggtgctggcg gaaaacctga tcgcctctat gctcgacctc gaagtggcgt   8040
ccgccaacga ccagactttc tcccactcgg atattcgccg caccgcgcgc accctgatgc   8100
agatgctgcc gggcaccgac tttatttct ccggctacag cgcggtgccg aactacgaca    8160
acatgttcgc cggctcgaac ttcgatgcgg aagattttga tgattacaac atcctgcagc   8220
gtgacctgat ggttgacggc ggcctgcgtc cggtgaccga ggcggaaacc attgccattc   8280
gccagaaagc ggcgcgggcg atccaggcgg ttttccgcga gctgggctg ccgccaatcg    8340 ccgacgagga ggtggaggcc gccacctacg cgcacggcag caacgagatg ccgccgcgta   8400
acgtggtgga ggatctgagt gcggtggaag agatgatgaa gcgcaacatc accggcctcg   8460
atattgtcgg cgcgctgagc cgcagcggct ttgaggatat cgccagcaat attctcaata   8520
tgctgcgcca gcgggtcacc ggcgattacc tgcagacctc ggccattctc gatcggcagt   8580
tcgaggtggt gagtgcggtc aacgacatca atgactatca ggggccgggc accggctatc   8640
gcatctctgc cgaacgctgg gcggagatca aaaatattcc gggcgtggtt cagcccgaca   8700
ccattgaata aggcggtatt cctgtgcaac agacaaccca aattcagccc tcttttaccc   8760 tgaaacccg cgagggcggg gtagcttctg ccgatgaacg cgccgatgaa gtggtgatcg    8820
gcgtcggccc tgccttcgat aaacaccagc atcacactct gatcgatatg ccccatggcg   8880
cgatcctcaa agagctgatt gccggggtgg aagaagaggg gcttcacgcc cggtggtgc    8940 gcattctgcg cacgtccgac gtctccttta tggcctggga tgcggccaac ctgagcggct   9000
cggggatcgg catcggtatc cagtcgaagg ggaccacggt catccatcag cgcgatctgc   9060
tgccgctcag caacctggag ctgttctccc aggcgccgct gctgacgctg agacctacc    9120 ggcagattgg caaaaacgct gcgcgctatg cgcgcaaaga gtcaccttcg ccggtgccgg   9180
tggtgaacga tcagatggtg cggccgaaat ttatggccaa agccgcgcta tttcatatca   9240
aagagaccaa acatgtggtg caggacgccg agcccgtcac cctgcacatc gacttagtaa   9300
gggagtgacc atgagcgaga aaaccatgcg cgtgcaggat tatccgttag ccacccgctg   9360
```

```
cccggagcat atcctgacgc ctaccggcaa accattgacc gatattaccc tcgagaaggt    9420
gctctctggc gaggtgggcc cgcaggatgt gcggatctcc cgccagaccc ttgagtacca    9480
ggcgcagatt gccgagcaga tgcagcgcca tgcggtggcg cgcaatttcc gccgcgcggc    9540
ggagcttatc gccattcctg acgagcgcat tctggctatc tataacgcgc tgcgcccgtt    9600
ccgctcctcg caggcggagc tgctggcgat cgccgacgag ctggagcaca cctggcatgc    9660
gacagtgaat gccgcctttg tccgggagtc ggcggaagtg tatcagcagc ggcataagct    9720
gcgtaaagga agctaagcgg aggtcagcat gccgttaata ccgggattg atatcggcaa     9780
cgccaccacc gaggtggcgc tggcgtccga ctacccgcag gcgagggcgt ttgttgccag    9840
cgggatcgtc gcgacgacgg gcatgaaagg gacgcgggac aatatcgccg ggaccctcgc    9900
cgcgctggag caggccctgg cgaaaacacc gtggtcgatg agcgatgtct ctcgcatcta    9960
tcttaacgaa gccgcgccgg tgattggcga tgtggcgatg gagaccatca ccgagaccat   10020
tatcaccgaa tcgaccatga tcggtcataa cccgcagacg ccgggcgggg tgggcgttgg   10080
cgtggggacg actatcgccc tcgggcggct ggcgacgctg ccggcggcgc agtatgccga   10140
ggggtggatc gtactgattg acgacgccgt cgatttcctt gacgccgtgt ggtggctcaa   10200
tgaggcgctc gaccgggga tcaacgtggt ggcggcgatc ctcaaaaagg acgacggcgt    10260
gctggtgaac aaccgcctgc gtaaaaccct gccggtggtg gatgaagtga cgctgctgga   10320
gcaggtcccc gagggggtaa tggcggcggt ggaagtggcc gcgccgggcc aggtggtgcg   10380
gatcctgtcg aatccctacg ggatcgccac cttcttcggg ctaagcccgg aagagaccca   10440
ggccatcgtc cccatcgccc gcgccctgat tggcaaccgt tccgcggtgg tgctcaagac   10500
cccgcagggg gatgtgcagt cgcggtgat cccggcgggc aacctctaca ttagcggcga    10560
aaagcgccgc ggagaggccg atgtcgccga gggcgcggaa gccatcatgc aggcgatgag   10620
cgcctgcgct ccggtacgcg acatccgcgg cgaaccgggc acccacgccg gcggcatgct   10680
tgagcgggtg cgcaaggtaa tggcgtccct gaccggccat gagatgagcg cgatatacat   10740
ccaggatctg ctggcggtgg atacgtttat tccgcgcaag gtgcagggcg ggatggccgg   10800
cgagtgcgcc atggagaatg ccgtcgggat ggcggcgatg gtgaaagcgg atcgtctgca   10860
aatgcaggtt atcgcccgcg aactgagcgc ccgactgcag accgaggtgg tgtgggcgg    10920
cgtggaggcc aacatggcca tcgccggggc gttaaccact cccggctgtg cggcgccgct   10980
ggcgatcctc gacctcggcg ccggctcgac ggatgcggcg atcgtcaacg cggagggcga   11040
gataacggcg gtccatctcg ccggggcggg gaatatggtc agcctgttga ttaaaaccga   11100
gctgggcctc gaggatcttt cgctggcgga agcgataaaa aaataccgc tggccaaagt    11160
ggaaagcctg ttcagtattc gtcacgagaa tggcgcggtg gagttctttc gggaagccct   11220
cagcccggcg gtgttcgcca aagtggtgta catcaaggag ggcgaactgg tgccgatcga   11280
taacgccagc ccgctggaaa aaattcgtct cgtgcgccgg caggcgaaag agaaagtgtt   11340
tgtcaccaac tgcctgcgcg cgctgcgcca ggtctcaccc ggcggttcca ttcgcgatat   11400
cgcctttgtg gtgctggtgg gcggctcatc gctggacttt gagatcccgc agcttatcac   11460
ggaagccttg tcgcactatg gcgtggtcgc cgggcagggc aatattcggg aacagaagg    11520
gccgcgcaat gcggtcgcca ccgggctgct actggcggt caggcgaatt aaacgggcgc    11580
tcgcgccagc ctctctcttt aacgtgctat ttcaggatgc cgataatgaa ccagacttct   11640
accttaaccg ggcagtgcgt ggccgagttt cttggcaccg gattgctcat tttcttcggc   11700
gcgggctgcg tcgctgcgct gcgggtcgcc ggggccagct ttggtcagtg ggagatcagt   11760
```

```
attatctggg gccttggcgt cgccatggcc atctacctga cggccggtgt ctccggcgcg   11820
cacctaaatc cggcggtgac cattgccctg tggctgttcg cctgttttga acgccgcaag   11880
gtgctgccgt ttattgttgc ccagacggcc ggggccttct gcgccgccgc gctggtgtat   11940
gggctctatc gccagctgtt tctcgatctt gaacagagtc agcatatcgt gcgcggcact   12000
gccgccagtc ttaacctggc cggggtcttt tccacgtacc cgcatccaca tatcactttt   12060
atacaagcgt tgccgtgga gaccaccatc acggcaatcc tgatggcgat gatcatggcc   12120
ctgaccgacg acggcaacgg aattc                                         12145
```

<210> SEQ ID NO 49
<211> LENGTH: 37
<212> TYPE: DNA
<213> ORGANISM: artificial sequence
<220> FEATURE:
<223> OTHER INFORMATION: primer

<400> SEQUENCE: 49
ggaattcaga tctcagcaat gagcgagaaa accatgc                37

<210> SEQ ID NO 50
<211> LENGTH: 27
<212> TYPE: DNA
<213> ORGANISM: artificial sequence
<220> FEATURE:
<223> OTHER INFORMATION: primer

<400> SEQUENCE: 50
gctctagatt agcttccttt acgcagc                27

<210> SEQ ID NO 51
<211> LENGTH: 33
<212> TYPE: DNA
<213> ORGANISM: artificial sequence
<220> FEATURE:
<223> OTHER INFORMATION: primer

<400> SEQUENCE: 51
ggccaagctt aaggaggtta attaaatgaa aag                33

<210> SEQ ID NO 52
<211> LENGTH: 26
<212> TYPE: DNA
<213> ORGANISM: artificial sequence
<220> FEATURE:
<223> OTHER INFORMATION: primer

<400> SEQUENCE: 52
gctctagatt attcaatggt gtcggg                26

<210> SEQ ID NO 53
<211> LENGTH: 26
<212> TYPE: DNA
<213> ORGANISM: artificial sequence
<220> FEATURE:
<223> OTHER INFORMATION: primer

<400> SEQUENCE: 53
gctctagatt attcaatggt gtcggg                26

<210> SEQ ID NO 54
<211> LENGTH: 42
<212> TYPE: DNA
<213> ORGANISM: artificial sequence

```
<220> FEATURE:
<223> OTHER INFORMATION: primer

<400> SEQUENCE: 54
gcgccgtcta gaattatgag ctatcgtatg tttgattatc tg                          42

<210> SEQ ID NO 55
<211> LENGTH: 18
<212> TYPE: DNA
<213> ORGANISM: artificial sequence
<220> FEATURE:
<223> OTHER INFORMATION: primer

<400> SEQUENCE: 55
tcgacgaatt caggagga                                                      18

<210> SEQ ID NO 56
<211> LENGTH: 18
<212> TYPE: DNA
<213> ORGANISM: artificial sequence
<220> FEATURE:
<223> OTHER INFORMATION: primer

<400> SEQUENCE: 56
ctagtcctcc tgaattcg                                                      18

<210> SEQ ID NO 57
<211> LENGTH: 133
<212> TYPE: DNA
<213> ORGANISM: artificial sequence
<220> FEATURE:
<223> OTHER INFORMATION: fragment

<400> SEQUENCE: 57
agtcaaaagc ctccgaccgg aggcttttga ctgctagcaa acacagaaaa aagcccgcac        60
ctgacagtgc gggcttttt tttcctaggt acaaataaaa aaggcacgtc agatgacgtg       120 cctttttct tgt                                                           133

<210> SEQ ID NO 58
<211> LENGTH: 100
<212> TYPE: DNA
<213> ORGANISM: artificial sequence
<220> FEATURE:
<223> OTHER INFORMATION: primer

<400> SEQUENCE: 58
ggaattcatt taaatagtca aaagcctccg accggaggct tttgactgct agcaaacaca        60 gaaaaagcc cgcacctgac agtgcgggct ttttttttcc                              100

<210> SEQ ID NO 59
<211> LENGTH: 100
<212> TYPE: DNA
<213> ORGANISM: artificial sequence
<220> FEATURE:
<223> OTHER INFORMATION: primer

<400> SEQUENCE: 59
ggggtaccat ttaaatgtat actctagaca agaaaaaagg cacgtcatct gacgtgcctt        60
ttttatttgt acctaggaaa aaaaagccc gcactgtcag                              100

<210> SEQ ID NO 60
<211> LENGTH: 175
<212> TYPE: DNA
<213> ORGANISM: artificial sequence
```

```
<220> FEATURE:
<223> OTHER INFORMATION: fragment

<400> SEQUENCE: 60
ggaattcatt taaatagtca aaagcctccg accggaggct tttgactgct agcaaacaca      60
gaaaaaagcc cgcacctgac agtgcgggct tttttttcc taggtacaaa taaaaaaggc     120
acgtcagatg acgtgccttt tttcttgtct agagtataca tttaaatggt acccc         175

<210> SEQ ID NO 61
<211> LENGTH: 20
<212> TYPE: DNA
<213> ORGANISM: artificial sequence
<220> FEATURE:
<223> OTHER INFORMATION: primer

<400> SEQUENCE: 61
ggaattcatt taaatagtca                                                  20

<210> SEQ ID NO 62
<211> LENGTH: 20
<212> TYPE: DNA
<213> ORGANISM: artificial sequence
<220> FEATURE:
<223> OTHER INFORMATION: primer

<400> SEQUENCE: 62
ggggtaccat ttaaatgtat                                                  20

<210> SEQ ID NO 63
<211> LENGTH: 21
<212> TYPE: DNA
<213> ORGANISM: artificial sequence
<220> FEATURE:
<223> OTHER INFORMATION: primer

<400> SEQUENCE: 63
gacgcaacag tattccgtcg c                                                21

<210> SEQ ID NO 64
<211> LENGTH: 42
<212> TYPE: DNA
<213> ORGANISM: artificial sequence
<220> FEATURE:
<223> OTHER INFORMATION: primer

<400> SEQUENCE: 64
atgagctatc gtatgttccg ccaggcattc tgagtgttaa cg                         42

<210> SEQ ID NO 65
<211> LENGTH: 33
<212> TYPE: DNA
<213> ORGANISM: artificial sequence
<220> FEATURE:
<223> OTHER INFORMATION: primer

<400> SEQUENCE: 65
gcctggcgga acatacgata gctcataata tac                                   33

<210> SEQ ID NO 66
<211> LENGTH: 21
<212> TYPE: DNA
<213> ORGANISM: artificial sequence
<220> FEATURE:
<223> OTHER INFORMATION: primer

<400> SEQUENCE: 66
```

-continued

```
cggggcgctg ggccagtact g                                        21

<210> SEQ ID NO 67
<211> LENGTH: 53
<212> TYPE: DNA
<213> ORGANISM: artificial sequence
<220> FEATURE:
<223> OTHER INFORMATION: linker

<400> SEQUENCE: 67
tctagaggat ccgctagcac tagtagcccg ggcgctagcg cggccgcccc ggg     53

<210> SEQ ID NO 68
<211> LENGTH: 37
<212> TYPE: DNA
<213> ORGANISM: artificial sequence
<220> FEATURE:
<223> OTHER INFORMATION: primer

<400> SEQUENCE: 68
tattcagctg gctagcgtgc accaatgctt ctggcgt                       37

<210> SEQ ID NO 69
<211> LENGTH: 35
<212> TYPE: DNA
<213> ORGANISM: artificial sequence
<220> FEATURE:
<223> OTHER INFORMATION: primer

<400> SEQUENCE: 69
gatccagctg gagtttgtag aaacgcaaaa aggcc                         35

<210> SEQ ID NO 70
<211> LENGTH: 7283
<212> TYPE: DNA
<213> ORGANISM: artificial sequence
<220> FEATURE:
<223> OTHER INFORMATION: plasmid

<400> SEQUENCE: 70
tagtaaagcc ctcgctagat tttaatgcgg atgttgcgat tacttcgcca actattgcga    60
taacaagaaa aagccagcct ttcatgatat atctcccaat ttgtgtaggg cttattatgc   120
acgcttaaaa ataataaaag cagacttgac ctgatagttt ggctgtgagc aattatgtgc   180
ttagtgcatc taacgcttga gttaagccgc gccgcgaagc ggcgtcggct tgaacgaatt   240
gttagacatt atttgccgac taccttggtg atctcgcctt tcacgtagtg acaaattct    300 tccaactgat ctgcgcgcga ggccaagcga tcttcttctt gtccaagata agcctgtcta   360
gcttcaagta tgacgggctg atactgggcc ggcaggcgct ccattgccca gtcggcagcg   420
acatccttcg gcgcgatttt gccggttact gcgctgtacc aaatgcggga caacgtaagc   480
actacatttc gctcatcgcc agcccagtcg ggcggcgagt tccatagcgt taaggtttca   540
tttagcgcct caaatagatc ctgttcagga accggatcaa agagttcctc cgccgctgga   600
cctaccaagg caacgctatg ttctcttgct tttgtcagca agatagccag atcaatgtcg   660
atcgtggctg gctcgaagat acctgcaaga atgtcattgc gctgccattc tccaaattgc   720
agttcgcgct tagctggata acgccacgga atgatgtcgt cgtgcacaac aatggtgact   780
tctacagcgc ggagaatctc gctctctcca ggggaagccg aagtttccaa aggtcgttg    840 atcaaagctc gccgcgttgt ttcatcaagc cttacggtca ccgtaaccag caaatcaata   900
tcactgtgtg gcttcaggcc gccatccact gcggagccgt acaaatgtac ggccagcaac   960
```

```
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctgaagg cgagcatcgt ttgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctatttcttc cagaattgcc atgattttt ccccacggga ggcgtcactg     1920
gctcccgtgt tgtcggcagc tttgattcga taagcagcat cgcctgtttc aggctgtcta    1980
tgtgtgactt tgagctgta acaagttgtc tcaggtgttc aatttcatgt tctagttgct     2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160
ctatcttttt tacaccgttt tcatctgtgc atatggacag ttttcccttt gatatgtaac    2220
ggtgaacagt tgttctactt tgttttgtta gtccttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520
attttatct ggttgttctc aagttcggtt acgagatcca tttgtctatc tagttcaact     2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttctttttg tgttagttct tttaataacc actcataaat cctcatagag   2820
tatttgtttt caaagacttt aacatgttcc agattatatt ttatgaattt ttttaactgg   2880
aaaagataag gcaatatctc ttcactaaaa actaattcta attttcgct tgagaacttg     2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataaattac tagtcctttt cctttgagtt gtgggtatct gtaaattctg ctagaccttt    3360
```

```
gctggaaaac ttgtaaattc tgctagaccc tctgtaaatt ccgctagacc tttgtgtgtt    3420 tttttttgttt atattcaagt ggttataatt tatagaataa agaaagaata aaaaaagata   3480
aaaagaatag atcccagccc tgtgtataac tcactacttt agtcagttcc gcagtattac    3540
aaaaggatgt cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc     3720
agtgaatggg ggtaaatggc actacaggcg cctttatgg attcatgcaa ggaaactacc     3780
cataatacaa gaaaagcccg tcacgggctt ctcagggcgt tttatggcgg gtctgctatg    3840
tggtgctatc tgacttttg ctgttcagca gttcctgccc tctgattttc cagtctgacc     3900
acttcggatt atcccgtgac aggtcattca gactggctaa tgcacccagt aaggcagcgg    3960
tatcatcaac aggcttaccc gtcttactgt cgggaattcg cgttggccga ttcattaatg    4020
cagctggcac gacaggtttc ccgactggaa agcgggcagt gagcgcaacg caattaatgt    4080
gagttagctc actcattagg cacccccaggc tttacacttt atgcttccgg ctcgtatgtt   4140
gtgtggaatt gtgagcggat aacaatttca cacaggaaac agctatgacc atgattacgc    4200
caagcttgca tgcctgcagg tcgactctag aggatccgct agcactagta gccctattca    4260
gctggctagc gtgcaccaat gcttctggcg tcaggcagcc atcggaagct gtggtatggc    4320
tgtgcaggtc gtaaatcact gcataattcg tgtcgctcaa ggcgcactcc cgttctggat    4380
aatgtttttt gcgccgacat cataacggtt ctggcaaata ttctgaaatg agctgttgac    4440
aattaatcat ccggctcgta taatgtgtgg aattgtgagc ggataacaat ttcacacagg    4500
aaacagacca tgactagtaa ggaggacaat tccatggctg ctgctgctga tagattaaac    4560
ttaacttccg gccacttgaa tgctggtaga agagaagtt cctcttctgt ttctttgaag      4620
gctgccgaaa agccttttcaa ggttactgtg attggatctg gtaactgggg tactactatt    4680
gccaaggtgg ttgccgaaaa ttgtaaggga tacccagaag ttttcgctcc aatagtacaa    4740
atgtgggtgt tcgaagaaga gatcaatggt gaaaaattga ctgaaatcat aaatactaga    4800
catcaaaacg tgaaatactt gcctggcatc actctacccg acaatttggt tgctaatcca    4860
gacttgattg attcagtcaa ggatgtcgac atcatcgttt tcaacattcc acatcaattt    4920
ttgccccgta tctgtagcca attgaaaggt catgttgatt cacacgtcag agctatctcc    4980
tgtctaaagg gttttgaagt tggtgctaaa ggtgtccaat tgctatcctc ttacatcact    5040
gaggaactag gtattcaatg tggtgctcta tctggtgcta acattgccac cgaagtcgct    5100
caagaacact ggtctgaaac aacagttgct taccacattc caaaggattt cagaggcgag    5160
ggcaaggacg tcgaccataa ggttctaaag gccttgttcc acagaccta cttccacgtt     5220 agtgtcatcg aagatgttgc tggtatctcc atctgtggtg ctttgaagaa cgttgttgcc    5280
ttaggttgtg gtttcgtcga aggtctaggc tggggtaaca acgcttctgc tgccatccaa    5340
agagtcggtt gggtgagat catcagattc ggtcaaatgt ttttcccaga atctagagaa     5400
gaaacatact accaagagtc tgctggtgtt gctgatttga tcaccacctg cgctggtggt    5460
agaaacgtca aggttgctag gctaatggct acttctggta aggacgcctg ggaatgtgaa    5520
aaggagttgt tgaatggcca atccgctcaa ggtttaatta cctgcaaaga agttcacgaa    5580
tggttggaaa catgtggctc tgtcgaagac ttcccattat ttgaagccgt ataccaaatc    5640
gtttacaaca actacccaat gaagaacctg ccggacatga ttgaagaatt agatctcat     5700 gaagattaga tttattggat ccaggaaaca gactagaatt atgggattga ctactaaacc    5760
```

```
tctatctttg aaagttaacg ccgctttgtt cgacgtcgac ggtaccatta tcatctctca    5820
accagccatt gctgcattct ggagggattt cggtaaggac aaaccttatt tcgatgctga    5880
acacgttatc caagtctcgc atggttggag aacgtttgat gccattgcta agttcgctcc    5940
agactttgcc aatgaagagt atgttaacaa attagaagct gaaattccgg tcaagtacgg    6000
tgaaaaatcc attgaagtcc caggtgcagt taagctgtgc aacgctttga cgctctacc    6060
aaaagagaaa tgggctgtgg caacttccgg tacccgtgat atggcacaaa atggttcga    6120
gcatctggga atcaggagac caaagtactt cattaccgct aatgatgtca acagggtaa    6180
gcctcatcca gaaccatatc tgaagggcag gaatggctta ggatatccga tcaatgagca    6240
agacccttcc aaatctaagg tagtagtatt tgaagacgct ccagcaggta ttgccgccgg    6300
aaaagccgcc ggttgtaaga tcattggtat tgccactact ttcgacttgg acttcctaaa    6360
ggaaaaggc tgtgacatca ttgtcaaaaa ccacgaatcc atcagagttg gcggctacaa    6420
tgccgaaaca gacgaagttg aattcatttt tgacgactac ttatatgcta aggacgatct    6480
gttgaaatgg taacccgggc tgcaggcatg caagcttggc tgttttggcg gatgagagaa    6540
gattttcagc ctgatacaga ttaaatcaga acgcagaagc ggtctgataa aacagaattt    6600
gcctggcggc agtagcgcgg tggtcccacc tgaccccatg ccgaactcag aagtgaaacg    6660
ccgtagcgcc gatggtagtg tggggtctcc ccatgcgaga gtagggaact gccaggcatc    6720
aaataaaacg aaaggctcag tcgaaagact gggcctttcg ttttatctgt tgtttgtcgg    6780
tgaacgctct cctgagtagg acaaatccgc cgggagcgga tttgaacgtt gcgaagcaac    6840
ggcccggagg gtggcgggca ggacgcccgc cataaactgc caggcatcaa attaagcaga    6900
aggccatcct gacggatggc cttttttgcgt ttctacaaac tccagctgga tcgggcgcta    6960
gcgcggccgc cccgggtacc gagctcgaat tcactggccg tcgttttaca acgtcgtgac    7020
tgggaaaacc ctggcgttac ccaacttaat cgccttgcag cacatccccc tttcgccagc    7080
tggcgtaata gcgaagaggc ccgcaccgat cgcccttccc aacagttgcg cagcctgaat    7140
ggcgaatggc gcctgatgcg gtattttctc cttacgcatc tgtgcggtat ttcacaccgc    7200
atatggtgca ctctcagtac aatctgctct gatgccgcat agttaagcca gccccgacac    7260
ccgccaacac ccgctgacga gct                                            7283
```

<210> SEQ ID NO 71
<211> LENGTH: 13669
<212> TYPE: DNA
<213> ORGANISM: artificial sequence
<220> FEATURE:
<223> OTHER INFORMATION: plasmid

<400> SEQUENCE: 71

```
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg acaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
```

```
tttagcgcct caaatagatc ctgttcagga accggatcaa agagttcctc cgccgctgga      600
cctaccaagg caacgctatg ttctcttgct tttgtcagca agatagccag atcaatgtcg      660
atcgtggctg gctcgaagat acctgcaaga atgtcattgc gctgccattc tccaaattgc      720
agttcgcgct tagctggata acgccacgga atgatgtcgt cgtgcacaac aatggtgact      780
tctacagcgc ggagaatctc gctctctcca ggggaagccg aagtttccaa aaggtcgttg      840
atcaaagctc gccgcgttgt ttcatcaagc cttacggtca ccgtaaccag caaatcaata      900
tcactgtgtg gcttcaggcc gccatccact gcggagccgt acaaatgtac ggccagcaac      960
gtcggttcga gatggcgctc gatgacgcca actacctctg atagttgagt cgatacttcg     1020
gcgatcaccg cttccctcat gatgtttaac tttgttttag ggcgactgcc ctgctgcgta     1080
acatcgttgc tgctccataa catcaaacat cgacccacgg cgtaacgcgc ttgctgcttg     1140
gatgcccgag gcatagactg tacccccaaaa aaacagtcat aacaagccat gaaaaccgcc     1200
actgcgccgt taccaccgct gcgttcggtc aaggttctgg accagttgcg tgagcgcata     1260
cgctacttgc attacagctt acgaaccgaa caggcttatg tccactgggt tcgtgccttc     1320
atccgtttcc acggtgtgcg tcacccggca accttgggca gcagcgaagt cgaggcattt     1380
ctgtcctggc tggcgaacga gcgcaaggtt tcggtctcca cgcatcgtca ggcattggcg     1440
gccttgctgt tcttctacgg caaggtgctg tgcacggatc tgccctggct tcaggagatc     1500
ggaagacctc ggccgtcgcg gcgcttgccg gtggtgctga ccccggatga agtggttcgc     1560
atcctcggtt ttctggaagg cgagcatcgt ttgttcgccc agcttctgta tggaacgggc     1620
atgcggatca gtgagggttt gcaactgcgg gtcaaggatc tggatttcga tcacggcacg     1680
atcatcgtgc gggagggcaa gggctccaag gatcgggcct tgatgttacc cgagagcttg     1740
gcacccagcc tgcgcgagca ggggaattaa ttcccacggg ttttgctgcc cgcaaacggg     1800
ctgttctggt gttgctagtt tgttatcaga atcgcagatc cggcttcagc cggtttgccg     1860
gctgaaagcg ctatttcttc cagaattgcc atgatttttt ccccacggga ggcgtcactg     1920
gctcccgtgt tgtcggcagc tttgattcga taagcagcat cgcctgtttc aggctgtcta     1980
tgtgtgactg ttgagctgta acaagttgtc tcaggtgttc aatttcatgt tctagttgct     2040
ttgttttact ggtttcacct gttctattag gtgttacatg ctgttcatct gttacattgt     2100
cgatctgttc atggtgaaca gctttgaatg caccaaaaac tcgtaaaagc tctgatgtat     2160
ctatcttttt tacaccgttt tcatctgtgc atatggacag ttttcccttt gatatgtaac     2220
ggtgaacagt tgttctactt tgtttgtta gtcttgatgc ttcactgata gatacaagag     2280
ccataagaac ctcagatcct tccgtattta gccagtatgt tctctagtgt ggttcgttgt     2340
ttttgcgtga gccatgagaa cgaaccattg agatcatact tactttgcat gtcactcaaa     2400
aattttgcct caaaactggt gagctgaatt tttgcagtta aagcatcgtg tagtgttttt     2460
cttagtccgt tatgtaggta ggaatctgat gtaatggttg ttggtatttt gtcaccattc     2520 attttatct ggttgttctc aagttcggtt acgagatcca tttgtctatc tagttcaact     2580
tggaaaatca acgtatcagt cgggcggcct cgcttatcaa ccaccaattt catattgctg     2640
taagtgttta aatctttact tattggtttc aaaacccatt ggttaagcct tttaaactca     2700
tggtagttat tttcaagcat taacatgaac ttaaattcat caaggctaat ctctatattt     2760
gccttgtgag ttttctttg tgttagttct tttaataacc actcataaat cctcatagag     2820
tatttgtttt caaaagactt aacatgttcc agattatatt ttatgaattt ttttaactgg     2880
aaaagataag gcaatatctc ttcactaaaa actaattcta attttcgct tgagaacttg     2940
```

```
gcatagtttg tccactggaa aatctcaaag cctttaacca aaggattcct gatttccaca    3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagaccttt   3360
gctggaaaac ttgtaaattc tgctagaccc tctgtaaatt ccgctagacc tttgtgtgtt   3420
ttttttgttt atattcaagt ggttataatt tatagaataa agaaagaata aaaaagata    3480
aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc    3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga    4860
ccataaccta tgacggaggc ggtgacgccg ctgcgctggg cgccctggcg gccagaagct   4920
cgccctgcg ggtgggtatc gggctcagcc cgtccggcga gatagccctc actcatgccc    4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaggcac caccgccctg tacgcggca    5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
```

```
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcacgtggcg cgcacccagt cccgtcggct cgaacgcctg ctgacggcca    5520
tggaccgcgc gcatccgctg cgcgacgcgc tcaaacgcta cagcaatcgc ctgtcggatg    5580
ccctgttctc catggcgcga atcaagagac taggcctga tgcttgcgct tgaactggcc    5640
tagcaaacac agaaaaaagc ccgcacctga cagtgcgggc ttttttttc ctaggcgatc    5700 tgtgctgttt gccacggtat gcagcaccag cgcgagatta tgggctcgca cgctcgactg    5760
tcggacgggg gcactggaac gagaagtcag gcgagccgtc acgcccttga caatgccaca    5820
tcctgagcaa ataattcaac cactaaacaa atcaaccgcg tttcccggag gtaaccaagc    5880
ttcacctttt gagccgatga acaatgaaaa gatcaaaacg atttgcagta ctggcccagc    5940
gccccgtcaa tcaggacggg ctgattggcg agtggcctga agaggggctg atcgccatgg    6000
acagccccct tgacccggtc tcttcagtaa aagtggacaa cggtctgatc gtcgaactgg    6060
acggcaaacg ccgggaccag tttgacatga tcgaccgatt tatcgccgat tacgcgatca    6120
acgttgagcg cacagagcag gcaatgcgcc tggaggcggt ggaaatagcc cgtatgctgg    6180
tggatattca cgtcagccgg gaggagatca ttgccatcac taccgccatc acgccggcca    6240
aagcggtcga ggtgatggcg cagatgaacg tggtggagat gatgatgcgc ctgcagaaga    6300
tgcgtgcccg ccggaccccc tccaaccagt gccacgtcac caatctcaaa gataatccgg    6360
tgcagattgc cgctgacgcc gccgaggcgg ggatccgcgg cttctcagaa caggagacca    6420
cggtcggtat cgcgcgctac gcgccgttta acgccctggc gctgttggtc ggttcgcagt    6480
gcggccgccc cggcgtgttg acgcagtgct cggtggaaga ggccaccgag ctggagctgg    6540
gcatgcgtgg cttaaccagc tacgccgaga cggtgtcggt ctacggcacc gaagcggtat    6600
ttaccgacgg cgatgatacg ccgtggtcaa aggcgttcct cgcctcggcc tacgcctccc    6660
gcgggttgaa aatgcgctac acctccggca ccggatccga agcgctgatg ggctattcgg    6720
agagcaagtc gatgctctac ctcgaatcgc gctgcatctt cattactaaa ggcgccgggg    6780
ttcagggact gcaaaacggc gcggtgagct gtatcggcat gaccggcgct gtgccgtcgg    6840
gcattcgggc ggtgctggcg gaaaacctga tcgcctctat gctcgacctc gaagtggcgt    6900
ccgccaacga ccagactttc tcccactcgg atattcgccg caccgcgcgc accctgatgc    6960
agatgctgcc gggcaccgac tttatttttct ccggctacag cgcggtgccg aactacgaca    7020
acatgttcgc cggctcgaac ttcgatgcgg aagattttga tgattacaac atcctgcagc    7080
gtgacctgat ggttgacggc ggcctgcgtc cggtgaccga ggcggaaacc attgccattc    7140
gccagaaagc ggcgcgggcg atccaggcgg ttttccgcga gctggggctg ccgccaatcg    7200
ccgacgagga ggtggaggcc gccacctacg cgcacggcag caacgagatg ccgccgcgta    7260
acgtggtgga ggatctgagt gcggtggaag agatgatgaa gcgcaacatc accggcctcg    7320
atattgtcgg cgcgctgagc cgcagcggct tgaggatat cgccagcaat attctcaata    7380
tgctgcgcca gcgggtcacc ggcgattacc tgcagacctc ggccattctc gatcggcagt    7440
tcgaggtggt gagtgcggtc aacgacatca atgactatca ggggccgggc accggctatc    7500
gcatctctgc cgaacgctgg gcggagatca aaaatattcc gggcgtggtt cagcccgaca    7560
ccattgaata aggcggtatt cctgtgcaac agacaaccca aattcagccc tcttttaccc    7620
tgaaaacccg cgagggcggg gtagcttctg ccgatgaacg cgccgatgaa gtggtgatcg    7680
gcgtcggccc tgccttcgat aaacaccagc atcacactct gatcgatatg ccccatggcg    7740
```

```
cgatcctcaa agagctgatt gccggggtgg aagaagaggg gcttcacgcc cgggtggtgc   7800
gcattctgcg cacgtccgac gtctccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg gagacctacc   7980
ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgccttg tccgggagtc ggcggaagtg tatcagcagc ggcataagct   8580
gcgtaaagga agctaagcgg aggtcagcat gccgttaata gccgggattg atatcggcaa   8640
cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacggcgt   9120
gctggtgaac aaccgcctgc gtaaaaccct gccggtggtg gatgaagtga cgctgctgga   9180
gcaggtcccc gagggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tgtgggcgg   9780 cgtggaggcc aacatggcca tcgccgggc gttaaccact cccggctgtg cggcgccgct   9840
ggcgatcctc gacctcggcg ccggctcgac ggatgcggcg atcgtcaacg cggagggca   9900 gataacggcg gtccatctcg ccggggcggg gaatatggtc agcctgttga ttaaaaccga   9960
gctgggcctc gaggatcttt cgctggcgga agcgataaaa aaataccgc tggccaaagt   10020 ggaaagcctt ttcagtattc gtcacgagaa tggcgcggtg gagttctttc gggaagccct   10080
cagcccggcg gtgttcgcca aagtggtgta catcaaggag ggcgaactgg tgccgatcga   10140
```

```
taacgccagc ccgctggaaa aaattcgtct cgtgcgccgg caggcgaaag agaaagtgtt    10200
tgtcaccaac tgcctgcgcg cgctgcgcca ggtctcaccc ggcggttcca ttcgcgatat    10260
cgcctttgtg gtgctggtgg gcggctcatc gctggacttt gagatcccgc agcttatcac    10320
ggaagccttg tcgcactatg gcgtggtcgc cgggcagggc aatattcggg gaacagaagg    10380
gccgcgcaat gcggtcgcca ccgggctgct actggccggt caggcgaatt aaacgggcgc    10440
tcgcgccagc ctctaggtac aaataaaaaa ggcacgtcag atgacgtgcc ttttttcttg    10500
tctagagtac tggcgaaagg gggatgtgct gcaaggcgat taagttgggt aacgccaggg    10560
ttttcccagt cacgacgttg taaaacgacg ccagtgaat tcgagctcgg tacccggggc    10620
ggccgcgcta gcgcccgatc cagctggagt ttgtagaaac gcaaaaaggc catccgtcag    10680
gatggccttc tgcttaattt gatgcctggc agtttatggc gggcgtcctg cccgccaccc    10740
tccgggccgt tgcttcgcaa cgttcaaatc cgctcccggc ggatttgtcc tactcaggag    10800
agcgttcacc gacaaacaac agataaaacg aaaggcccag tctttcgact gagcctttcg    10860
ttttatttga tgcctggcag ttccctactc tcgcatgggg agaccccaca ctaccatcgg    10920
cgctacggcg tttcacttct gagttcggca tggggtcagg tgggaccacc gcgctactgc    10980
cgccaggcaa attctgtttt atcagaccgc ttctgcgttc tgatttaatc tgtatcaggc    11040
tgaaaatctt ctctcatccg ccaaaacagc caagcttgca tgcctgcagc ccgggttacc    11100
atttcaacag atcgtcctta gcatataagt agtcgtcaaa aatgaattca acttcgtctg    11160
tttcggcatt gtagccgcca actctgatgg attcgtggtt tttgacaatg atgtcacagc    11220 cttttttcctt taggaagtcc aagtcgaaag tagtggcaat accaatgatc ttacaaccgg    11280
cggcttttcc ggcggcaata cctgctggag cgtcttcaaa tactactacc ttagatttgg    11340
aagggtcttg ctcattgatc ggatatccta agccattcct gcccttcaga tatggttctg    11400
gatgaggctt accctgtttg acatcattag cggtaatgaa gtactttggt ctcctgattc    11460
ccagatgctc gaaccatttt tgtgccatat cacgggtacc ggaagttgcc acagcccatt    11520 tctctttttgg tagagcgttc aaagcgttgc acagcttaac tgcacctggg acttcaatgg    11580 attttttcacc gtacttgacc ggaatttcag cttctaattt gttaacatac tcttcattgg    11640
caaagtctgg agcgaactta gcaatggcat caaacgttct ccaaccatgc gagacttgga    11700
taacgtgttc agcatcgaaa taaggtttgt ccttaccgaa atccctccag aatgcagcaa    11760
tggctggttg agagatgata atggtaccgt cgacgtcgaa caaagcggcg ttaactttca    11820
aagatagagg tttagtagtc aatcccataa ttctagtctg tttcctggat ccaataaatc    11880
taatcttcat gtagatctaa ttcttcaatc atgtccggca ggttcttcat tgggtagttg    11940
ttgtaaacga tttggtatac ggcttcaaat aatgggaagt cttcgacaga gccacatgtt    12000
tccaaccatt cgtgaacttc tttgcaggta attaaacctt gagcggattg gccattcaac    12060
aactcctttt cacattccca ggcgtcctta ccagaagtag ccattagcct agcaaccttg    12120
acgtttctac caccagcgca ggtggtgatc aaatcagcaa caccagcaga ctcttggtag    12180
tatgtttctt ctctagattc tgggaaaaac atttgaccga atctgatgat ctcacccaaa    12240
ccgactcttt ggatggcagc agaagcgttg ttaccccagc ctagaccttc gacgaaacca    12300
caacctaagg caacaacgtt cttcaaagca ccacagatgg agataccagc aacatcttcg    12360
atgacactaa cgtggaagta aggtctgtgg aacaaggcct ttagaacctt atggtcgacg    12420
tccttgccct cgcctctgaa atcctttgga atgtggtaag caactgttgt tcagaccag    12480 tgttcttgag cgacttcggt ggcaatgtta gcaccagata gagcaccaca ttgaatacct    12540
```

| | | | | |
|---|---|---|---|---|
| agttcctcag | tgatgtaaga | ggatagcaat | tggacacctt | tagcaccaac ttcaaaaccc | 12600 |
| tttagacagg | agatagctct | gacgtgtgaa | tcaacatgac | ctttcaattg gctacagata | 12660 |
| cggggcaaaa | attgatgtgg | aatgttgaaa | acgatgatgt | cgacatcctt gactgaatca | 12720 |
| atcaagtctg | gattagcaac | caaattgtcg | ggtagagtga | tgccaggcaa gtatttcacg | 12780 |
| ttttgatgtc | tagtatttat | gatttcagtc | aattttttcac | cattgatctc ttcttcgaac | 12840 |
| acccacattt | gtactattgg | agcgaaaact | tctgggtatc | ccttacaatt ttcggcaacc | 12900 |
| accttggcaa | tagtagtacc | ccagttacca | gatccaatca | cagtaacctt gaaaggcttt | 12960 |
| tcggcagcct | tcaaagaaac | agaagaggaa | cttctctttc | taccagcatt caagtggccg | 13020 |
| gaagttaagt | ttaatctatc | agcagcagca | gccatggaat | tgtcctcctt actagtcatg | 13080 |
| gtctgtttcc | tgtgtgaaat | tgttatccgc | tcacaattcc | acacattata cgagccggat | 13140 |
| gattaattgt | caacagctca | tttcagaata | tttgccagaa | ccgttatgat gtcggcgcaa | 13200 |
| aaaacattat | ccagaacggg | agtgcgcctt | gagcgacacg | aattatgcag tgatttacga | 13260 |
| cctgcacagc | cataccacag | cttccgatgg | ctgcctgacg | ccagaagcat tggtgcacgc | 13320 |
| tagccagtac | atttaaatgg | taccctctag | tcaaggcctt | aagtgagtcg tattacggac | 13380 |
| tggccgtcgt | tttacaacgt | cgtgactggg | aaaaccctgg | cgttacccaa cttaatcgcc | 13440 |
| ttgcagcaca | tccccctttc | gccagctggc | gtaatagcga | agaggcccgc accgatcgcc | 13500 |
| cttcccaaca | gttgcgcagc | ctgaatggcg | aatggcgcct | gatgcggtat tttctcctta | 13560 |
| cgcatctgtg | cggtatttca | caccgcatat | ggtgcactct | cagtacaatc tgctctgatg | 13620 |
| ccgcatagtt | aagccagccc | cgacacccgc | caacacccgc | tgacgagct | 13669 |

<210> SEQ ID NO 72
<211> LENGTH: 13543
<212> TYPE: DNA
<213> ORGANISM: artificial sequence
<220> FEATURE:
<223> OTHER INFORMATION: plasmid

<400> SEQUENCE: 72

| | | | | |
|---|---|---|---|---|
| tagtaaagcc | ctcgctagat | tttaatgcgg | atgttgcgat | tacttcgcca actattgcga | 60 |
| taacaagaaa | aagccagcct | ttcatgatat | atctcccaat | ttgtgtaggg cttattatgc | 120 |
| acgcttaaaa | ataataaaag | cagacttgac | ctgatagttt | ggctgtgagc aattatgtgc | 180 |
| ttagtgcatc | taacgcttga | gttaagccgc | gccgcgaagc | ggcgtcggct tgaacgaatt | 240 |
| gttagacatt | atttgccgac | taccttggtg | atctcgcctt | tcacgtagtg acaaattct | 300 |
| tccaactgat | ctgcgcgcga | ggccaagcga | tcttcttctt | gtccaagata agcctgtcta | 360 |
| gcttcaagta | tgacgggctg | atactgggcc | ggcaggcgct | ccattgccca gtcggcagcg | 420 |
| acatccttcg | gcgcgatttt | gccggttact | gcgctgtacc | aaatgcggga caacgtaagc | 480 |
| actacatttc | gctcatcgcc | agcccagtcg | ggcggcgagt | tccatagcgt taaggtttca | 540 |
| tttagcgcct | caaatagatc | ctgttcagga | accggatcaa | agagttcctc cgccgctgga | 600 |
| cctaccaagg | caacgctatg | ttctcttgct | tttgtcagca | agatagccag atcaatgtcg | 660 |
| atcgtggctg | gctcgaagat | acctgcaaga | atgtcattgc | gctgccattc tccaaattgc | 720 |
| agttcgcgct | tagctggata | acgccacgga | atgatgtcgt | cgtgcacaac aatggtgact | 780 |
| tctacagcgc | ggagaatctc | gctctctcca | ggggaagccg | aagtttccaa aaggtcgttg | 840 |
| atcaaagctc | gccgcgttgt | ttcatcaagc | cttacggtca | ccgtaaccag caaatcaata | 900 |
| tcactgtgtg | gcttcaggcc | gccatccact | gcggagccgt | acaaatgtac ggccagcaac | 960 |

```
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg tacccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga ccccggatga agtggttcgc   1560
atcctcggtt ttctgaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
gctcccgtgt tgtcggcagc tttgattcga taagcagcat cgcctgtttc aggctgtcta   1980
tgtgtgactt tgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt tgtttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta aatctttact tattggtttc aaaacccatt ggttaagcct tttaaactca   2700
tggtagttat tttcaagcat taacatgaac ttaaattcat caaggctaat ctctatattt   2760
gccttgtgag ttttctttg tgttagttct tttaataacc actcataaat cctcatagag   2820
tatttgtttt caaaagactt aacatgttcc agattatatt ttatgaattt ttttaactgg   2880
aaaagataag gcaatatctc ttcactaaaa actaattcta attttcgct tgagaacttg   2940 gcatagtttg tccactggaa atctcaaag cctttaacca aaggattcct gatttccaca   3000
gttctcgtca tcagctctct ggttgcttta gctaatacac cataagcatt ttccctactg   3060
atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300 tgataaattac tagtcctttt cctttgagtt gtgggtatct gtaaattctg ctagaccttt   3360
```

```
gctggaaaac ttgtaaattc tgctagaccc tctgtaaatt ccgctagacc tttgtgtgtt    3420 tttttttgttt atattcaagt ggttataatt tatagaataa agaaagaata aaaaaagata   3480 aaagaatag atcccagccc tgtgtataac tcactacttt agtcagttcc gcagtattac    3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc tttttcgtga cattcagttc gctgcgctca cggctctggc   3720
agtgaatggg ggtaaatggc actacaggcg cctttatgg attcatgcaa ggaaactacc    3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga    4860 ccataaccta tgacggaggc ggtgacgccg ctgcgctggg cgccctggcg gccagaagct   4920
cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacgcggca    5160 gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640 tagcaaaacac agaaaaaagc ccgcacctga cagtgcgggc tttttttttc ctaggcgatc   5700
tgtgctgttt gccacggtat gcagcaccag cgcgagatta tgggctcgca cgctcgactg   5760
```

```
tcggacgggg gcactggaac gagaagtcag gcgagccgtc acgcccttga ctatgccaca      5820
tcctgagcaa ataattcaac cactaaacaa atcaaccgcg tttcccggag gtaaccaagc      5880 ttcaccttt gagccgatga acaatgaaaa gatcaaaacg atttgcagta ctggcccagc       5940
gccccgtcaa tcaggacggg ctgattggcg agtggcctga agaggggctg atcgccatgg      6000 acagccctt tgacccggtc tcttcagtaa aagtggacaa cggtctgatc gtcgaactgg       6060
acggcaaacg ccgggaccag tttgacatga tcgaccgatt tatcgccgat tacgcgatca     6120
acgttgagcg cacagagcag gcaatgcgcc tggaggcggt ggaaatagcc cgtatgctgg      6180
tggatattca cgtcagccgg gaggagatca ttgccatcac taccgccatc acgccggcca      6240
aagcggtcga ggtgatggcg cagatgaacg tggtggagat gatgatgcg ctgcagaaga       6300 tgcgtgcccg ccggacccc tccaaccagt gccacgtcac caatctcaaa gataatccgg       6360
tgcagattgc cgctgacgcc gccgaggccg ggatccgcgg cttctcagaa caggagacca      6420
cggtcggtat cgcgcgctac gcgccgttta acgccctggc gctgttggtc ggttcgcagt      6480
gcggccgccc cggcgtgttg acgcagtgct cggtggaaga ggccaccgag ctggagctgg      6540
gcatgcgtgg cttaaccagc tacgccgaga cggtgtcggt ctacggcacc gaagcggtat     6600
ttaccgacgg cgatgatacg ccgtggtcaa aggcgttcct cgcctcggcc tacgcctccc      6660
gcgggttgaa aatgcgctac acctccggca ccggatccga agcgctgatg ggctattcgg      6720
agagcaagtc gatgctctac ctcgaatcgc gctgcatctt cattactaaa ggcgccgggg      6780
ttcagggact gcaaaacggc gcggtgagct gtatcggcat gaccggcgct gtgccgtcgg      6840
gcattcgggc ggtgctggcg gaaaacctga tcgcctctat gctcgacctc gaagtggcgt      6900
ccgccaacga ccagactttc tcccactcgg atattcgccg caccgcgcgc accctgatgc      6960
agatgctgcc gggcaccgac tttatttct ccggctacag cgcggtgccg aactacgaca       7020
acatgttcgc cggctcgaac ttcgatgcgg aagattttga tgattacaac atcctgcagc      7080
gtgacctgat ggttgacggc ggcctgcgtc cggtgaccga ggcggaaacc attgccattc      7140
gccagaaagc ggcgcgggcg atccaggcgg ttttccgcga gctggggctg ccgccaatcg      7200
ccgacgagga ggtggaggcc gccacctacg cgcacggcag caacgagatg ccgccgcgta     7260
acgtggtgga ggatctgagt gcggtggaag agatgatgaa gcgcaacatc accgcctcg      7320 atattgtcgg cgcgctgagc cgcagcggct ttgaggatat cgccagcaat attctcaata      7380
tgctgcgcca gcgggtcacc ggcgattacc tgcagacctc ggccattctc gatcggcagt      7440
tcgaggtggt gagtgcggtc aacgacatca atgactatca ggggccgggc accggctatc      7500
gcatctctgc cgaacgctgg gcggagatca aaaatattcc gggcgtggtt cagcccgaca      7560
ccattgaata aggcggtatt cctgtgcaac agacaaccca aattcagccc tcttttaccc      7620
tgaaaacccg cgagggcggg gtagcttctg ccgatgaacg cgccgatgaa gtggtgatcg      7680
gcgtcggccc tgccttcgat aaacaccagc atcacactct gatcgatatg ccccatggcg      7740
cgatcctcaa agagctgatt gccggggtgg aagaagaggg gcttcacgcc cgggtggtgc      7800
gcattctgcg cacgtccgac gtctccttta tggcctggga tgcggccaac ctgagcggct      7860
cggggatcgg catcggtatc cagtcgaagg ggaccacggt catccatcag cgcgatctgc      7920
tgccgctcag caacctggag ctgttctccc aggcgccgct gctgacgctg agacctacc       7980 ggcagattgg caaaaacgct gcgcgctatg cgcgcaaaga gtcaccttcg ccggtgccgg      8040
tggtgaacga tcagatggtg cggccgaaat ttatggccaa agccgcgcta tttcatatca      8100
aagagaccaa acatgtggtg caggacgccg agcccgtcac cctgcacatc gacttagtaa      8160
```

```
gggagtgacc atgagcgaga aaaccatgcg cgtgcaggat tatccgttag ccacccgctg    8220
cccggagcat atcctgacgc ctaccggcaa accattgacc gatattaccc tcgagaaggt    8280
gctctctggc gaggtgggcc cgcaggatgt gcggatctcc cgccagaccc ttgagtacca    8340
ggcgcagatt gccgagcaga tgcagcgcca tgcggtggcg cgcaatttcc gccgcgcggc    8400
ggagcttatc gccattcctg acgagcgcat tctggctatc tataacgcgc tgcgcccgtt    8460
ccgctcctcg caggcggagc tgctggcgat cgccgacgag ctggagcaca cctggcatgc    8520
gacagtgaat gccgcctttg tccgggagtc ggcggaagtg tatcagcagc ggcataagct    8580
gcgtaaagga agctaagcgg aggtcagcat gccgttaata gccgggattg atatcggcaa    8640
cgccaccacc gaggtggcgc tggcgtccga ctacccgcag gcgagggcgt ttgttgccag    8700
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg gagaccatca ccgagaccat    8880
tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacggcgt    9120
gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tggtgggcgg    9780
cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaataccgc tggccaaagt    10020
ggaaagcctt ttcagtattc gtcacgagaa tggcgcggtg gagttctttc gggaagccct    10080
cagcccggcg gtgttcgcca agtggtgta catcaaggag ggcgaactgg tgccgatcga    10140
taacgccagc ccgctggaaa aaattcgtct cgtgcgccgg caggcgaaag agaaagtgtt    10200
tgtcaccaac tgcctgcgcg cgctgcgcca ggtctcaccc ggcggttcca ttcgcgtat    10260
cgcctttgtg gtgctggtgg gcggctcatc gctggacttt gagatcccgc agcttatcac    10320
ggaagccttg tcgcactatg gcgtggtcgc cgggcagggc aatattcggg aacagaaggg    10380
gccgcgcaat gcggtcgcca ccgggctgct actggccggt caggcgaatt aaacgggcgc    10440
tcgcgccagc ctctaggtac aaataaaaaa ggcacgtcag atgacgtgcc ttttttcttg    10500
tctagcgtgc accaatgctt ctggcgtcag gcagccatcg gaagctgtgg tatggctgtg    10560
```

```
caggtcgtaa atcactgcat aattcgtgtc gctcaaggcg cactcccgtt ctggataatg    10620
ttttttgcgc cgacatcata acggttctgg caaatattct gaaatgagct gttgacaatt    10680
aatcatccgg ctcgtataat gtgtggaatt gtgagcggat aacaatttca cacaggaaac    10740
agaccatgac tagtaaggag gacaattcca tggctgctgc tgctgataga ttaaacttaa    10800
cttccggcca cttgaatgct ggtagaaaga gaagttcctc ttctgttcct ttgaaggctg    10860
ccgaaaagcc tttcaaggtt actgtgattg gatctggtaa ctggggtact actattgcca    10920
aggtggttgc cgaaaattgt aagggatacc cagaagtttt cgctccaata gtacaaatgt    10980
gggtgttcga agaagagatc aatggtgaaa aattgactga aatcataaat actagacatc    11040
aaaacgtgaa atacttgcct ggcatcactc tacccgacaa tttggttgct aatccagact    11100
tgattgattc agtcaaggat gtcgacatca tcgtttttcaa cattccacat caattttttgc    11160 cccgtatctg tagccaattg aaaggtcatg ttgattcaca cgtcagagct atctcctgtc    11220
taaagggttt tgaagttggt gctaaaggtg tccaattgct atcctcttac atcactgagg    11280
aactaggtat tcaatgtggt gctctatctg gtgctaacat tgccaccgaa gtcgctcaag    11340
aacactggtc tgaaacaaca gttgcttacc acattccaaa ggatttcaga ggcgagggca    11400
aggacgtcga ccataaggtt ctaaaggcct tgttccacag accttacttc cacgttagtg    11460
tcatcgaaga tgttgctggt atctccatct gtggtgcttt gaagaacgtt gttgccttag    11520
gttgtggttt cgtcgaaggt ctaggctggg gtaacaacgc ttctgctgcc atccaaagag    11580
tcggtttggg tgagatcatc agattcggtc aaatgttttt cccagaatct agagaagaaa    11640
catactacca agagtctgct ggtgttgctg atttgatcac cacctgcgct ggtggtagaa    11700
acgtcaaggt tgctaggcta atggctactt ctggtaagga cgcctgggaa tgtgaaaagg    11760
agttgttgaa tggccaatcc gctcaaggtt taattacctg caaagaagtt cacgaatggt    11820
tggaaacatg tggctctgtc gaagacttcc cattatttga agccgtatac caaatcgttt    11880
acaacaacta cccaatgaag aacctgccgg acatgattga agaattagat ctacatgaag    11940
attagattta ttggatccag gaaacagact agaattatgg gattgactac taaacctcta    12000
tctttgaaag ttaacgccgc tttgttcgac gtcgacggta ccattatcat ctctcaacca    12060
gccattgctg cattctggag ggatttcggt aaggacaaac cttatttcga tgctgaacac    12120
gttatccaag tctcgcatgg ttggagaacg tttgatgcca ttgctaagtt cgctccagac    12180
tttgccaatg aagagtatgt taacaaatta gaagctgaaa ttccggtcaa gtacggtgaa    12240
aaatccattg aagtcccagg tgcagttaag ctgtgcaacg ctttgaacgc tctaccaaaa    12300
gagaaatggg ctgtggcaac ttccggtacc cgtgatatgg cacaaaaatg gttcgagcat    12360
ctgggaatca ggagaccaaa gtacttcatt accgctaatg atgtcaaaca gggtaagcct    12420
catccagaac catatctgaa gggcaggaat ggcttaggat atccgatcaa tgagcaagac    12480
ccttccaaat ctaaggtagt agtatttgaa gacgctccag caggtattgc cgccggaaaa    12540
gccgccggtt gtaagatcat tggtattgcc actactttcg acttggactt cctaaaggaa    12600
aaaggctgtg acatcattgt caaaaaccac gaatccatca gagttggcgg ctacaatgcc    12660
gaaacagacg aagttgaatt cattttttgac gactacttat atgctaagga cgatctgttg    12720
aaatggtaac ccgggctgca ggcatgcaag cttggctgtt ttggcggatg agaagagatt    12780
ttcagcctga tacagattaa atcagaacgc agaagcggtc tgataaaaca gaatttgcct    12840
ggcggcagta gcgcggtggt cccacctgac cccatgccga actcagaagt gaaacgccgt    12900
agcgccgatg gtagtgtggg gtctccccat gcgagagtag ggaactgcca ggcatcaaat    12960
```

```
aaaacgaaag gctcagtcga aagactgggc ctttcgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta agcagaaggc   13140
catcctgacg gatggccttt ttgcgtttct acaaactcca gctggatcgg gcgctagagt   13200
atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                     13543

<210> SEQ ID NO 73
<211> LENGTH: 13543
<212> TYPE: DNA
<213> ORGANISM: artificial sequence
<220> FEATURE:
<223> OTHER INFORMATION: plasmid

<400> SEQUENCE: 73
tagtaaagcc ctcgctagat tttaatgcgg atgttgcgat tacttcgcca actattgcga     60
taacaagaaa aagccagcct ttcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg gacaaattct    300
tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aaggtcgttg    840
atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag ggcgactgcc ctgctgcgta   1080
acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
```

```
ggaagacctc ggccgtcgcg gcgcttgccg gtggtgctga ccccggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgatttttt ccccacggga ggcgtcactg   1920
gctcccgtgt tgtcggcagc tttgattcga taagcagcat cgcctgtttc aggctgtcta   1980
tgtgtgactg ttgagctgta acaagttgtc tcaggtgttc aatttcatgt tctagttgct   2040
ttgttttact ggtttcacct gttctattag gtgttacatg ctgttcatct gttacattgt   2100
cgatctgttc atggtgaaca gctttgaatg caccaaaaac tcgtaaaagc tctgatgtat   2160
ctatcttttt tacaccgttt tcatctgtgc atatggacag ttttcccttt gatatgtaac   2220
ggtgaacagt tgttctactt ttgttttgtta gtcttgatgc ttcactgata gatacaagag   2280
ccataagaac ctcagatcct tccgtattta gccagtatgt tctctagtgt ggttcgttgt   2340
ttttgcgtga gccatgagaa cgaaccattg agatcatact tactttgcat gtcactcaaa   2400
aattttgcct caaaactggt gagctgaatt tttgcagtta aagcatcgtg tagtgttttt   2460
cttagtccgt tatgtaggta ggaatctgat gtaatggttg ttggtatttt gtcaccattc   2520 attttatct ggttgttctc aagttcggtt acgagatcca tttgtctatc tagttcaact   2580
tggaaaatca acgtatcagt cgggcggcct cgcttatcaa ccaccaattt catattgctg   2640
taagtgttta atctttact tattggttc aaaacccatt ggttaagcct tttaaactca   2700
tggtagttat tttcaagcat taacatgaac ttaaattcat caaggctaat ctctatattt   2760
gccttgtgag ttttcttttg tgttagttct tttaataacc actcataaat cctcatagag   2820
tatttgtttt caaaagactt aacatgttcc agattatatt ttatgaattt ttttaactgg   2880 aaagataag gcaatatctc ttcactaaaa actaattcta attttttcgct tgagaacttg   2940 gcatagtttg tccactggaa aatctcaaag cctttaacca aaggattcct gatttccaca   3000
gttctcgtca tcagctctct ggttgcttta gctaatacac cataagcatt tccctactg   3060 atgttcatca tctgagcgta ttggttataa gtgaacgata ccgtccgttc tttccttgta   3120
gggttttcaa tcgtggggtt gagtagtgcc acacagcata aaattagctt ggtttcatgc   3180
tccgttaagt catagcgact aatcgctagt tcatttgctt tgaaaacaac taattcagac   3240
atacatctca attggtctag gtgattttaa tcactatacc aattgagatg ggctagtcaa   3300
tgataattac tagtcctttt cctttgagtt gtgggtatct gtaaattctg ctagacctt   3360 gctggaaaac ttgtaaattc tgctagaccc tctgtaaatt ccgctagacc tttgtgtgtt   3420
ttttttgttt atattcaagt ggttataatt tatagaataa agaaagaata aaaaagata   3480 aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg cctttttatgg attcatgcaa ggaaactacc   3780
cataatacaa gaaaagcccg tcacgggctt ctcagggcgt tttatggcgg gtctgctatg   3840
tggtgctatc tgactttttg ctgttcagca gttcctgccc tctgattttc cagtctgacc   3900
```

```
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt gccacggtat gcagcaccag   4080
cgcgagatta tgggctcgca cgctcgactg tcggacgggg gcactggaac gagaagtcag   4140
gcgagccgtc acgcccttga caatgccaca tcctgagcaa ataattcaac cactaaacaa   4200
atcaaccgcg tttcccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt ggcggcggc   4560 ctgccagtta tttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg gccagaagct   4920
cgcccctgcg ggtgggtatc gggctcagcc gtccggcga gatagccctc actcatgccc   4980
agctgccggc ggacgcgccg ctggctaccg gacacgtcac cgatagcgac gatcaactgc   5040
gtacgctcgc cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccggggagg aatctcgcct   5460
ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700 tgtgctgttt gccacggtat gcagcaccag cgcgagatta tgggctcgca cgctcgactg   5760
tcggacgggg gcactggaac gagaagtcag gcgagccgtc acgcccttga caatgccaca   5820
tcctgagcaa ataattcaac cactaaacaa atcaaccgcg tttcccggag gtaaccaagc   5880 ttcaccttt gagccgatga acaatgaaaa gatcaaaacg atttgcagta ctggcccagc   5940
gccccgtcaa tcaggacggg ctgattggcg agtggcctga agaggggctg atcgccatgg   6000
acagcccctt tgacccggtc tcttcagtaa aagtggacaa cggtctgatc gtcgaactgg   6060
acggcaaacg ccgggaccag tttgacatga tcgaccgatt tatcgccgat tacgcgatca   6120
acgttgagcg cacagagcag gcaatgcgcc tggaggcggt ggaaatagcc cgtatgctgg   6180
tggatattca cgtcagccgg gaggagatca ttgccatcac taccgccatc acgccggcca   6240
aagcggtcga ggtgatggcg cagatgaacg tggtggagat gatgatggcg ctgcagaaga   6300
```

```
tgcgtgcccg ccggacccc tccaaccagt gccacgtcac caatctcaaa gataatccgg   6360
tgcagattgc cgctgacgcc gccgaggccg ggatccgcgg cttctcagaa caggagacca   6420
cggtcggtat cgcgcgctac gcgccgttta acgccctggc gctgttggtc ggttcgcagt   6480
gcggccgccc cggcgtgttg acgcagtgct cggtggaaga ggccaccgag ctggagctgg   6540
gcatgcgtgg cttaaccagc tacgccgaga cggtgtcggt ctacggcacc gaagcggtat   6600
ttaccgacgg cgatgatacg ccgtggtcaa aggcgttcct cgcctcggcc tacgcctccc   6660
gcgggttgaa aatgcgctac acctccggca ccggatccga agcgctgatg gctattcgg    6720 agagcaagtc gatgctctac ctcgaatcgc gctgcatctt cattactaaa ggcgccgggg   6780
ttcagggact gcaaaacggc gcggtgagct gtatcggcat gaccggcgct gtgccgtcgg   6840
gcattcgggc ggtgctggcg gaaaacctga tcgcctctat gctcgacctc gaagtggcgt   6900
ccgccaacga ccagactttc tcccactcgg atattcgccg caccgcgcgc accctgatgc   6960
agatgctgcc gggcaccgac tttatttct ccggctacag cgcggtgccg aactacgaca    7020
acatgttcgc cggctcgaac ttcgatgcgg aagattttga tgattacaac atcctgcagc   7080
gtgacctgat ggttgacggc ggcctgcgtc cggtgaccga ggcggaaacc attgccattc   7140
gccagaaagc ggcgcgggcg atccaggcgg ttttccgcga gctggggctg ccgccaatcg   7200
ccgacgagga ggtggaggcc gccacctacg cgcacggcag caacgagatg ccgccgcgta   7260
acgtggtgga ggatctgagt gcggtggaag agatgatgaa gcgcaacatc accggcctcg   7320
atattgtcgg cgcgctgagc cgcagcggct ttgaggatat cgccagcaat attctcaata   7380
tgctgcgcca gcgggtcacc ggcgattacc tgcagacctc ggccattctc gatcggcagt   7440
tcgaggtggt gagtgcggtc aacgacatca atgactatca ggggccgggc accggctatc   7500
gcatctctgc cgaacgctgg gcggagatca aaatattcc gggcgtggtt cagcccgaca    7560
ccattgaata aggcggtatt cctgtgcaac agacaaccca aattcagccc tcttttaccc   7620
tgaaaacccg cgagggcggg gtagcttctg ccgatgaacg cgccgatgaa gtggtgatcg   7680
gcgtcggccc tgccttcgat aaacaccagc atcacactct gatcgatatg ccccatggcg   7740
cgatcctcaa agagctgatt gccggggtgg aagaagaggg gcttcacgcc cggtggtgc    7800 gcattctgcg cacgtccgac gtctcccttta tggcctggga tgcggccaac ctgagcggct   7860
cggggatcgg catcggtatc cagtcgaagg ggaccacggt catccatcag cgcgatctgc   7920
tgccgctcag caacctggag ctgttctccc aggcgccgct gctgacgctg agacctacc    7980 ggcagattgg caaaaacgct gcgcgctatg cgcgcaaaga gtcaccttcg ccggtgccgg   8040
tggtgaacga tcagatggtg cggccgaaat ttatggccaa agccgcgcta tttcatatca   8100
aagagaccaa acatgtggtg caggacgccg agcccgtcac cctgcacatc gacttagtaa   8160
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcctttg tccgggagtc ggcggaagtg tatcagcagc ggcataagct   8580
gcgtaaagga agctaagcgg aggtcagcat gccgttaata gccggattg atatcggcaa    8640 cgccaccacc gaggtggcgc tggcgtccga ctacccgcag gcgagggcgt tgttgccag    8700
```

```
cgggatcgtc gcgacgacgg gcatgaaagg gacgcgggac aatatcgccg ggaccctcgc    8760
cgcgctggag caggccctgg cgaaaacacc gtggtcgatg agcgatgtct ctcgcatcta    8820
tcttaacgaa gccgcgccgg tgattggcga tgtggcgatg agaccatca ccgagaccat    8880 tatcaccgaa tcgaccatga tcggtcataa cccgcagacg ccgggcgggg tgggcgttgg    8940
cgtggggacg actatcgccc tcgggcggct ggcgacgctg ccggcggcgc agtatgccga    9000
ggggtggatc gtactgattg acgacgccgt cgatttcctt gacgccgtgt ggtggctcaa    9060
tgaggcgctc gaccggggga tcaacgtggt ggcggcgatc ctcaaaaagg acgacgcgt    9120 gctggtgaac aaccgcctgc gtaaaaccct gccggtggtg gatgaagtga cgctgctgga    9180
gcaggtcccc gagggggtaa tggcggcggt ggaagtggcc gcgccgggcc aggtggtgcg    9240
gatcctgtcg aatccctacg ggatcgccac cttcttcggg ctaagcccgg aagagaccca    9300
ggccatcgtc cccatcgccc gcgccctgat tggcaaccgt tccgcggtgg tgctcaagac    9360
cccgcagggg gatgtgcagt cgcgggtgat cccggcgggc aacctctaca ttagcggcga    9420
aaagcgccgc ggagaggccg atgtcgccga gggcgcggaa gccatcatgc aggcgatgag    9480
cgcctgcgct ccggtacgcg acatccgcgg cgaaccgggc acccacgccg gcggcatgct    9540
tgagcgggtg cgcaaggtaa tggcgtccct gaccggccat gagatgagcg cgatatacat    9600
ccaggatctg ctggcggtgg atacgtttat tccgcgcaag gtgcagggcg ggatggccgg    9660
cgagtgcgcc atggagaatg ccgtcgggat ggcggcgatg gtgaaagcgg atcgtctgca    9720
aatgcaggtt atcgcccgcg aactgagcgc ccgactgcag accgaggtgg tgtgggcgg    9780 cgtggaggcc aacatggcca tcgccggggc gttaaccact cccggctgtg cggcgccgct    9840
ggcgatcctc gacctcggcg ccggctcgac ggatgcggcg atcgtcaacg cggaggggca    9900
gataacggcg gtccatctcg ccggggcggg gaatatggtc agcctgttga ttaaaaccga    9960
gctgggcctc gaggatcttt cgctggcgga agcgataaaa aaatacccgc tggccaaagt   10020
ggaaagcctg ttcagtattc gtcacgagaa tggcgcggtg gagttctttc gggaagccct   10080
cagcccggcg gtgttcgcca aagtggtgta catcaaggag ggcgaactgg tgccgatcga   10140
taacgccagc ccgctggaaa aaattcgtct cgtgcgccgg caggcgaaag agaaagtgtt   10200
tgtcaccaac tgcctgcgcg cgctgcgcca ggtctcaccc ggcggttcca ttcgcgatat   10260
cgcctttgtg gtgctggtgg gcggctcatc gctggacttt gagatcccgc agcttatcac   10320
ggaagccttg tcgcactatg gcgtggtcgc cgggcagggc aatattcggg gaacagaagg   10380
gccgcgcaat gcggtcgcca ccgggctgct actggccggt caggcgaatt aaacgggcgc   10440
tcgcgccagc tctaggtac aaataaaaaa ggcacgtcag atgacgtgcc tttttttcttg   10500 tctagcgtgc accaatgctt ctggcgtcag gcagccatcg gaagctgtgg tatggctgtg   10560
caggtcgtaa atcactgcat aattcgtgtc gctcaaggcg cactcccgtt ctggataatg   10620 tttttttgcgc cgacatcata acggttctgg caaatattct gaaatgagct gttgacaatt   10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
```

```
tgattgattc agtcaaggat gtcgacatca tcgttttcaa cattccacat caattttttgc   11160
cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caaagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat   12360
ctgggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt catttttgac gactacttat atgctaagga cgatctgttg   12720
aaatggtaac ccgggctgca ggcatgcaag cttggctgtt ttggcggatg agaagagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
aaaacgaaag gctcagtcga agactgggcc tttcgttttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta agcagaaggc   13140
catcctgacg gatggccttt ttgcgtttct acaaactcca gctggatcgg cgctagagt   13200
atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgcccttccc   13380
aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
```
agttaagcca gccccgacac ccgccaacac ccgctgacga gct 13543

<210> SEQ ID NO 74
<211> LENGTH: 13402
<212> TYPE: DNA
<213> ORGANISM: artificial sequence
<220> FEATURE:
<223> OTHER INFORMATION: plasmid

<400> SEQUENCE: 74

| | | | | | |
|---|---|---|---|---|---|
| tagtaaagcc | ctcgctagat | tttaatgcgg | atgttgcgat | tacttcgcca | actattgcga | 60 |
| taacaagaaa | aagccagcct | tcatgatat | atctcccaat | ttgtgtaggg | cttattatgc | 120 |
| acgcttaaaa | ataataaaag | cagacttgac | ctgatagttt | ggctgtgagc | aattatgtgc | 180 |
| ttagtgcatc | taacgcttga | gttaagccgc | gccgcgaagc | ggcgtcggct | tgaacgaatt | 240 |
| gttagacatt | atttgccgac | taccttggtg | atctcgcctt | tcacgtagtg | gacaaattct | 300 |
| tccaactgat | ctgcgcgcga | ggccaagcga | tcttcttctt | gtccaagata | agcctgtcta | 360 |
| gcttcaagta | tgacgggctg | atactgggcc | ggcaggcgct | ccattgccca | gtcggcagcg | 420 |
| acatccttcg | gcgcgatttt | gccggttact | gcgctgtacc | aaatgcggga | caacgtaagc | 480 |
| actacatttc | gctcatcgcc | agcccagtcg | ggcggcgagt | tccatagcgt | taaggtttca | 540 |
| tttagcgcct | caaatagatc | ctgttcagga | accggatcaa | agagttcctc | cgccgctgga | 600 |
| cctaccaagg | caacgctatg | ttctcttgct | tttgtcagca | agatagccag | atcaatgtcg | 660 |
| atcgtggctg | gctcgaagat | acctgcaaga | atgtcattgc | gctgccattc | tccaaattgc | 720 |
| agttcgcgct | tagctggata | acgccacgga | atgatgtcgt | cgtgcacaac | aatggtgact | 780 |
| tctacagcgc | ggagaatctc | gctctctcca | ggggaagccg | aagttccaa | aaggtcgttg | 840 |
| atcaaagctc | gccgcgttgt | ttcatcaagc | cttacggtca | ccgtaaccag | caaatcaata | 900 |
| tcactgtgtg | gcttcaggcc | gccatccact | gcggagccgt | acaaatgtac | ggccagcaac | 960 |
| gtcggttcga | gatggcgctc | gatgacgcca | actacctctg | atagttgagt | cgatacttcg | 1020 |
| gcgatcaccg | cttccctcat | gatgtttaac | tttgttttag | gcgactgcc | ctgctgcgta | 1080 |
| acatcgttgc | tgctccataa | catcaaacat | cgacccacgg | cgtaacgcgc | ttgctgcttg | 1140 |
| gatgcccgag | gcatagactg | taccccaaaa | aaacagtcat | aacaagccat | gaaaaccgcc | 1200 |
| actgcgccgt | taccaccgct | gcgttcggtc | aaggttctgg | accagttgcg | tgagcgcata | 1260 |
| cgctacttgc | attacagctt | acgaaccgaa | caggcttatg | tccactgggt | tcgtgccttc | 1320 |
| atccgtttcc | acggtgtgcg | tcacccggca | accttgggca | gcagcgaagt | cgaggcattt | 1380 |
| ctgtcctggc | tggcgaacga | gcgcaaggtt | tcggtctcca | cgcatcgtca | ggcattggcg | 1440 |
| gccttgctgt | tcttctacgg | caaggtgctg | tgcacggatc | tgccctggct | tcaggagatc | 1500 |
| ggaagacctc | ggccgtcgcg | gcgcttgccg | gtggtgctga | cccggatga | agtggttcgc | 1560 |
| atcctcggtt | ttctggaagg | cgagcatcgt | tgttcgccc | agcttctgta | tggaacgggc | 1620 |
| atgcggatca | gtgagggttt | gcaactgcgg | gtcaaggatc | tggatttcga | tcacggcacg | 1680 |
| atcatcgtgc | gggagggcaa | gggctccaag | gatcgggcct | tgatgttacc | cgagagcttg | 1740 |
| gcacccagcc | tgcgcgagca | ggggaattaa | ttcccacggg | ttttgctgcc | cgcaaacggg | 1800 |
| ctgttctggt | gttgctagtt | tgttatcaga | atcgcagatc | cggcttcagc | cggtttgccg | 1860 |
| gctgaaagcg | ctatttcttc | cagaattgcc | atgattttt | ccccacggga | ggcgtcactg | 1920 |
| gctcccgtgt | tgtcggcagc | tttgattcga | taagcagcat | cgcctgtttc | aggctgtcta | 1980 |
| tgtgtgactg | ttgagctgta | acaagttgtc | tcaggtgttc | aatttcatgt | tctagttgct | 2040 |

```
ttgtttact  ggtttcacct  gttctattag  gtgttacatg  ctgttcatct  gttacattgt  2100
cgatctgttc  atggtgaaca  gctttgaatg  caccaaaaac  tcgtaaaagc  tctgatgtat  2160
ctatctttt   tacaccgttt  tcatctgtgc  atatggacag  ttttcccttt  gatatgtaac  2220
ggtgaacagt  tgttctactt  ttgtttgtta  gtcttgatgc  ttcactgata  gatacaagag  2280
ccataagaac  ctcagatcct  tccgtattta  gccagtatgt  tctctagtgt  ggttcgttgt  2340
ttttgcgtga  gccatgagaa  cgaaccattg  agatcatact  tactttgcat  gtcactcaaa  2400
aattttgcct  caaaactggt  gagctgaatt  tttgcagtta  aagcatcgtg  tagtgttttt  2460
cttagtccgt  tatgtaggta  ggaatctgat  gtaatggttg  ttggtatttt  gtcaccattc  2520
atttttatct  ggttgttctc  aagttcggtt  acgagatcca  tttgtctatc  tagttcaact  2580
tggaaaatca  acgtatcagt  cgggcggcct  cgcttatcaa  ccaccaattt  catattgctg  2640
taagtgttta  aatctttact  tattggtttc  aaaacccatt  ggttaagcct  tttaaactca  2700
tggtagttat  tttcaagcat  taacatgaac  ttaaattcat  caaggctaat  ctctatattt  2760
gccttgtgag  ttttctttg   tgttagttct  tttaataacc  actcataaat  cctcatagag  2820
tatttgtttt  caaaagactt  aacatgttcc  agattatatt  ttatgaattt  ttttaactgg  2880
aaaagataag  gcaatatctc  ttcactaaaa  actaattcta  attttcgct   tgagaacttg  2940
gcatagtttg  tccactggaa  aatctcaaag  cctttaacca  aaggattcct  gatttccaca  3000
gttctcgtca  tcagctctct  ggttgcttta  gctaatacac  cataagcatt  ttccctactg  3060
atgttcatca  tctgagcgta  ttggttataa  gtgaacgata  ccgtccgttc  tttccttgta  3120
gggttttcaa  tcgtggggtt  gagtagtgcc  acacagcata  aaattagctt  ggtttcatgc  3180
tccgttaagt  catagcgact  aatcgctagt  tcatttgctt  tgaaaacaac  taattcagac  3240
atacatctca  attggtctag  gtgattttaa  tcactatacc  aattgagatg  ggctagtcaa  3300
tgataattac  tagtccttt   cctttgagtt  gtgggtatct  gtaaattctg  ctagacctt   3360
gctggaaaac  ttgtaaattc  tgctagaccc  tctgtaaatt  ccgctagacc  tttgtgtgtt  3420
ttttttgttt  atattcaagt  ggttataatt  tatagaataa  agaaagaata  aaaaagata   3480
aaagaatag   atcccagccc  tgtgtataac  tcactacttt  agtcagttcc  gcagtattac  3540
aaaaggatgt  cgcaaacgct  gttttgctcct  ctacaaaaca  gaccttaaaa  ccctaaaggc  3600
ttaagtagca  ccctcgcaag  ctcgggcaaa  tcgctgaata  ttccttttgt  ctccgaccat  3660
caggcacctg  agtcgctgtc  tttttcgtga  cattcagttc  gctgcgctca  cggctctggc  3720
agtgaatggg  ggtaaatggc  actacaggcg  ccttttatgg  attcatgcaa  ggaaactacc  3780
cataatacaa  gaaaagcccg  tcacgggctt  tcagggcgt   tttatggcgg  gtctgctatg  3840
tggtgctatc  tgactttttg  ctgttcagca  gttcctgccc  tctgattttc  cagtctgacc  3900
acttcggatt  atcccgtgac  aggtcattca  gactggctaa  tgcacccagt  aaggcagcgg  3960
tatcatcaac  aggcttaccc  gtcttactgt  cgggaattca  tttaaatagt  caaaagcctc  4020
cgaccggagg  cttttgactg  ctaggcgatc  tgtgctgttt  gccacggtat  gcagcaccag  4080
cgcgagatta  tgggctcgca  cgctcgactg  tcggacgggg  gcactggaac  gagaagtcag  4140
gcgagccgtc  acgcccttga  caatgccaca  tcctgagcaa  ataattcaac  cactaaacaa  4200
atcaaccgcg  tttcccggag  gtaaccaagc  ttgcgggaga  gaatgatgaa  caagagccaa  4260
caagttcaga  caatcaccct  ggccgccgcc  cagcaaatgg  cggcggcggt  ggaaaaaaaa  4320
gccactgaga  tcaacgtggc  ggtggtgttt  tccgtagttg  accgcggagg  caacacgctg  4380
cttatccagc  ggatggacga  ggccttcgtc  tccagctgcg  atatttccct  gaataaagcc  4440
```

```
tggagcgcct gcagcctgaa gcaaggtacc catgaaatta cgtcagcggt ccagccagga    4500
caatctctgt acggtctgca gctaaccaac caacagcgaa ttattatttt tggcggcggc    4560
ctgccagtta tttttaatga gcaggtaatt ggcgccgtcg gcgttagcgg cggtacggtc    4620
gagcaggatc aattattagc ccagtgcgcc ctggattgtt tttccgcatt ataacctgaa    4680
gcgagaaggt atattatgag ctatcgtatg ttccgccagg cattctgagt gttaacgagg    4740
ggaccgtcat gtcgctttca ccgccaggcg tacgcctgtt ttacgatccg cgcgggcacc    4800
atgccggcgc catcaatgag ctgtgctggg ggctggagga cagggggtc ccctgccaga    4860 ccataaccta tgacggaggc ggtgacgccg ctgcgctggg cgcccggcg gccagaagct    4920 cgccctgcg ggtgggtatc gggctcagcc cgtccggcga gatagccctc actcatgccc    4980
agctgccggc ggacgcgccg ctggctaccg gacacgtcac cgatagcgac gatcaactgc    5040
gtacgctcgg cgccaacgcc gggcagctgg ttaaagtcct gccgttaagt gagagaaact    5100
gaatgtatcg tatctatacc cgcaccgggg ataaaggcac caccgccctg tacggcggca    5160
gccgcatcga gaaagaccat attcgcgtcg aggcctacgg caccgtcgat gaactgatat    5220
cccagctggg cgtctgctac gccacgaccc gcgacgccgg gctgcgggaa agcctgcacc    5280
atattcagca gacgctgttc gtgctggggg ctgaactggc cagcgatgcg cggggcctga    5340
cccgcctgag ccagacgatc ggcgaagagg agatcaccgc cctggagcgg cttatcgacc    5400
gcaatatggc cgagagcggc ccgttaaaac agttcgtgat cccggggagg aatctcgcct    5460
ctgcccagct gcaccctgat gcttgcgctt gaactggcct agcaaacaca gaaaaaagcc    5520
cgcacctgac agtgcgggct ttttttttcc taggcgatct gtgctgtttg ccacggtatg    5580
cagcaccagc gcgagattat gggctcgcac gctcgactgt cggacggggg cactggaacg    5640
agaagtcagg cgagccgtca cgcccttgac aatgccacat cctgagcaaa taattcaacc    5700
actaaacaaa tcaaccgcgt ttcccggagg taaccaagct tcaccttttg agccgatgaa    5760
caatgaaaag atcaaaacga tttgcagtac tggcccagcg ccccgtcaat caggacgggc    5820
tgattggcga gtggcctgaa gaggggctga tcgccatgga cagccccttt gacccggtct    5880
cttcagtaaa agtggacaac ggtctgatcg tcgaactgga cggcaaacgc cgggaccagt    5940
ttgacatgat cgaccgattt atcgccgatt acgcgatcaa cgttgagcgc acagagcagg    6000
caatgcgcct ggaggcggtg gaaatagccc gtatgctggt ggatattcac gtcagccggg    6060
aggagatcat tgccatcact accgccatca cgccggccaa agcggtcgag gtgatggcgc    6120
agatgaacgt ggtggagatg atgatggcgc tgcagaagat gcgtgcccgc cggaccccct    6180
ccaaccagtg ccacgtcacc aatctcaaag ataatccggt gcagattgcc gctgacgccg    6240
ccgaggccgg gatccgcggc ttctcagaac aggagaccac ggtcggtatc gcgcgctacg    6300
cgccgtttaa cgccctggcg ctgttggtcg gttcgcagtg cggccgcccc ggcgtgttga    6360
cgcagtgctc ggtggaagag gccaccgagc tggagctggg catgcgtggc ttaaccagct    6420
acgccgagac ggtgtcggtc tacggcaccg aagcggtatt taccgacggc gatgatacgc    6480
cgtggtcaaa ggcgttcctc gcctcggcct acgcctcccg cgggttgaaa atgcgctaca    6540
cctccggcac cggatccgaa gcgctgatgg gctattcgga gagcaagtcg atgctctacc    6600
tcgaatcgcg ctgcatcttc attactaaag gcgccggggt tcagggactg caaaacggcg    6660
cggtgagctg tatcggcatg accgcgcgctg tgccgtcggg cattcgggcg gtgctggcgg    6720
aaaacctgat cgcctctatg ctcgacctcg aagtggcgtc cgccaacgac cagactttct    6780
cccactcgga tattcgccgc accgcgcgca ccctgatgca gatgctgccg ggcaccgact    6840
```

```
ttatttctc cggctacagc gcggtgccga actacgacaa catgttcgcc ggctcgaact    6900
tcgatgcgga agattttgat gattacaaca tcctgcagcg tgacctgatg gttgacggcg    6960
gcctgcgtcc ggtgaccgag gcggaaacca ttgccattcg ccagaaagcg gcgcgggcga    7020
tccaggcggt tttccgcgag ctggggctgc cgccaatcgc cgacgaggag gtggaggccg    7080
ccacctacgc gcacggcagc aacgagatgc cgccgcgtaa cgtggtggag gatctgagtg    7140
cggtggaaga gatgatgaag cgcaacatca ccggcctcga tattgtcggc gcgctgagcc    7200
gcagcggctt tgaggatatc gccagcaata ttctcaatat gctgcgccag cgggtcaccg    7260
gcgattacct gcagacctcg gccattctcg atcggcagtt cgaggtggtg agtgcggtca    7320
acgacatcaa tgactatcag gggccgggca ccggctatcg catctctgcc gaacgctggg    7380
cggagatcaa aaatattccg ggcgtggttc agcccgacac cattgaataa ggcggtattc    7440
ctgtgcaaca gacaacccaa attcagccct cttttaccct gaaacccgc gagggcgggg     7500
tagcttctgc cgatgaacgc gccgatgaag tggtgatcgg cgtcggccct gccttcgata    7560
aacaccagca tcacactctg atcgatatgc cccatggcgc gatcctcaaa gagctgattg    7620
ccggggtgga agaagagggg cttcacgccc gggtggtgcg cattctgcgc acgtccgacg    7680
tctcctttat ggcctgggat gcggccaacc tgagcggctc ggggatcggc atcggtatcc    7740
agtcgaaggg gaccacggtc atccatcagc gcgatctgct gccgctcagc aacctggagc    7800
tgttctccca ggcgccgctg ctgacgctgg agacctaccg gcagattggc aaaaacgctg    7860
cgcgctatgc gcgcaaagag tcaccttcgc cggtgccggt ggtgaacgat cagatggtgc    7920
ggccgaaatt tatggccaaa gccgcgctat ttcatatcaa agagaccaaa catgtggtgc    7980
aggacgccga gcccgtcacc ctgcacatcg acttagtaag ggagtgacca tgagcgagaa    8040
aaccatgcgc gtgcaggatt atccgttagc cacccgctgc ccggagcata tcctgacgcc    8100
taccggcaaa ccattgaccg atattaccct cgagaaggtg ctctctggcg aggtgggccc    8160
gcaggatgtg cggatctccc gccagaccct tgagtaccag gcgcagattg ccgagcagat    8220
gcagcgccat gcggtggcgc gcaatttccg ccgcgcggcg gagcttatcg ccattcctga    8280
cgagcgcatt ctggctatct ataacgcgct gcgcccgttc cgctcctcgc aggcggagct    8340
gctggcgatc gccgacgagc tggagcacac ctggcatgcg acagtgaatg ccgcctttgt    8400
ccggggagtcg gcggaagtgt atcagcagcg gcataagctg cgtaaaggaa gctaagcgga    8460
ggtcagcatg ccgttaatag ccgggattga tatcggcaac gccaccaccg aggtggcgct    8520
ggcgtccgac tacccgcagg cgagggcgtt tgttgccagc gggatcgtcg cgacgacggg    8580
catgaaaggg acgcgggaca atatcgccgg gaccctcgcc gcgctggagc aggccctggc    8640
gaaaacaccg tggtcgatga gcgatgtctc tcgcatctat cttaacgaag ccgcgccggt    8700
gattggcgat gtggcgatgg agaccatcac cgagaccatt atcaccgaat cgaccatgat    8760
cggtcataac ccgcagacgc cgggcgggt gggcgttggc gtggggacga ctatcgccct    8820
cgggcggctg cgcgacgctgc cggcggcgca gtatgccgag gggtggatcg tactgattga    8880
cgacgccgtc gatttccttg acgccgtgtg gtggctcaat gaggcgctcg accggggat     8940
caacgtggtg gcggcgatcc tcaaaaagga cgacggcgtg ctggtgaaca accgcctgcg    9000
taaaaccctg ccggtggtgg atgaagtgac gctgctggag caggtccccg agggggtaat    9060
ggcgcggtg gaagtggccg cgcggggcca ggtggtgcgg atcctgtcga atccctacgg    9120
gatcgccacc ttcttcgggc taagcccgga agagacccag gccatcgtcc ccatcgcccg    9180
cgccctgatt ggcaaccgtt ccgcggtggt gctcaagacc ccgcaggggg atgtgcagtc    9240
```

```
gcgggtgatc ccggcgggca acctctacat tagcggcgaa aagcgccgcg gagaggccga   9300
tgtcgccgag ggcgcggaag ccatcatgca ggcgatgagc gcctgcgctc cggtacgcga   9360
catccgcggc gaaccgggca cccacgccgg cggcatgctt gagcgggtgc gcaaggtaat   9420
ggcgtccctg accggccatg agatgagcgc gatatacatc caggatctgc tggcggtgga   9480
tacgtttatt ccgcgcaagg tgcagggcgg gatggccggc gagtgcgcca tggagaatgc   9540
cgtcgggatg gcggcgatgg tgaaagcgga tcgtctgcaa atgcaggtta tcgcccgcga   9600
actgagcgcc cgactgcaga ccgaggtggt ggtgggcggc gtggaggcca acatggccat   9660
cgccggggcg ttaaccactc ccggctgtgc ggcgccgctg gcgatcctcg acctcggcgc   9720
cggctcgacg gatgcggcga tcgtcaacgc ggaggggcag ataacggcgg tccatctcgc   9780
cggggcgggg aatatggtca gcctgttgat taaaaccgag ctgggcctcg aggatctttc   9840
gctggcggaa gcgataaaaa aatacccgct ggccaaagtg gaaagcctgt tcagtattcg   9900
tcacgagaat ggcgcggtgg agttctttcg ggaagccctc agcccggcgg tgttcgccaa   9960
agtggtgtac atcaaggagg gcgaactggt gccgatcgat aacgccagcc cgctggaaaa  10020
aattcgtctc gtgcgccggc aggcgaaaga gaaagtgttt gtcaccaact gcctgcgcgc  10080
gctgcgccag gtctcacccg gcggttccat tcgcgatatc gcctttgtgg tgctggtggg  10140
cggctcatcg ctggactttg agatcccgca gcttatcacg gaagccttgt cgcactatgg  10200
cgtggtcgcc gggcagggca atattcgggg aacagaaggg ccgcgcaatg cggtcgccac  10260
cgggctgcta ctgccggtc aggcgaatta acgggcgct cgcgccagcc tctaggtaca  10320
aataaaaaag gcacgtcaga tgacgtgcct ttttcttgt ctagcgtgca ccaatgcttc  10380
tggcgtcagg cagccatcgg aagctgtggt atggctgtgc aggtcgtaaa tcactgcata  10440
attcgtgtcg ctcaaggcgc actcccgttc tggataatgt tttttgcgcc gacatcataa  10500
cggttctggc aaatattctg aaatgagctg ttgacaatta atcatccggc tcgtataatg  10560
tgtggaattg tgagcggata caatttcac acaggaaaca gaccatgact agtaaggagg  10620
acaattccat ggctgctgct gctgatagat taaacttaac ttccggccac ttgaatgctg  10680
gtagaaagag aagttcctct tctgtttctt tgaaggctgc cgaaaagcct ttcaaggtta  10740
ctgtgattgg atctggtaac tggggtacta ctattgccaa ggtggttgcc gaaaattgta  10800
agggataccc agaagttttc gctccaatag tacaaatgtg ggtgttcgaa gaagagatca  10860
atggtgaaaa attgactgaa atcataaata ctagacatca aaacgtgaaa tacttgcctg  10920
gcatcactct acccgacaat ttggttgcta atccagactt gattgattca gtcaaggatg  10980
tcgacatcat cgtttttcaac attccacatc aattttttgcc ccgtatctgt agccaattga  11040
aaggtcatgt tgattcacac gtcagagcta tctcctgtct aaagggtttt gaagttggtg  11100
ctaaaggtgt ccaattgcta tcctcttaca tcactgagga actaggtatt caatgtggtg  11160
ctctatctgg tgctaacatt gccaccgaag tcgctcaaga acactggtct gaaacaacag  11220
ttgcttacca cattccaaag gatttcagag gcgagggcaa ggacgtcgac cataaggttc  11280
taaaggcctt gttccacaga ccttacttcc acgttagtgt catcgaagat gttgctggta  11340
tctccatctg tggtgctttg aagaacgttg ttgccttagg ttgtggtttc gtcgaaggtc  11400
taggctgggg taacaacgct tctgctgcca tccaaagagt cggtttgggt gagatcatca  11460
gattcggtca atgttttttc ccagaatcta gagaagaaac atactaccaa gagtctgctg  11520
gtgttgctga tttgatcacc acctgcgctg gtggtagaaa cgtcaaggtt gctaggctaa  11580
tggctacttc tggtaaggac gcctgggaat gtgaaaagga gttgttgaat ggccaatccg  11640
```

```
ctcaaggttt aattacctgc aaagaagttc acgaatggtt ggaaacatgt ggctctgtcg   11700
aagacttccc attatttgaa gccgtatacc aaatcgttta caacaactac ccaatgaaga   11760
acctgccgga catgattgaa gaattagatc tacatgaaga ttagatttat tggatccagg   11820
aaacagacta gaattatggg attgactact aaacctctat ctttgaaagt taacgccgct   11880
ttgttcgacg tcgacggtac cattatcatc tctcaaccag ccattgctgc attctggagg   11940
gatttcggta aggacaaacc ttatttcgat gctgaacacg ttatccaagt ctcgcatggt   12000
tggagaacgt ttgatgccat tgctaagttc gctccagact ttgccaatga agagtatgtt   12060
aacaaattag aagctgaaat tccggtcaag tacggtgaaa atccattga agtcccaggt    12120 gcagttaagc tgtgcaacgc tttgaacgct ctaccaaaag agaaatgggc tgtggcaact   12180
tccggtaccc gtgatatggc acaaaaatgg ttcgagcatc tgggaatcag gagaccaaag   12240
tacttcatta ccgctaatga tgtcaaacag ggtaagcctc atccagaacc atatctgaag   12300
ggcaggaatg gcttaggata tccgatcaat gagcaagacc cttccaaatc taaggtagta   12360
gtatttgaag acgctccagc aggtattgcc gccggaaaag ccgccggttg taagatcatt   12420
ggtattgcca ctactttcga cttggacttc ctaaaggaaa aaggctgtga catcattgtc   12480
aaaaaccacg aatccatcag agttggcggc tacaatgccg aaacagacga agttgaattc   12540 attttgacg actacttata tgctaaggac gatctgttga aatggtaacc cgggctgcag   12600
gcatgcaagc ttggctgttt tggcggatga gaagagattt cagcctgat acagattaaa    12660 tcagaacgca gaagcggtct gataaaacag aatttgcctg gcggcagtag cgcggtggtc   12720
ccacctgacc ccatgccgaa ctcagaagtg aaacgccgta gcgccgatgg tagtgtgggg   12780
tctccccatg cgagagtagg gaactgccag gcatcaaata aaacgaaagg ctcagtcgaa   12840
agactgggcc tttcgtttta tctgttgttt gtcggtgaac gctctcctga gtaggacaaa   12900
tccgccggga gcggatttga acgttgcgaa gcaacggccc ggagggtggc gggcaggacg   12960
cccgccataa actgccaggc atcaaattaa gcagaaggcc atcctgacgg atggcctttt   13020
tgcgttctta caaactccag ctggatcggg cgctagagta tacatttaaa tggtaccctc   13080
tagtcaaggc cttaagtgag tcgtattacg gactggccgt cgttttacaa cgtcgtgact   13140
gggaaaaccc tggcgttacc caacttaatc gccttgcagc acatccccct ttcgccagct   13200
ggcgtaatag cgaagaggcc cgcaccgatc gcccttccca acagttgcgc agcctgaatg   13260
gcgaatggcg cctgatgcgg tatttctcc ttacgcatct gtgcggtatt tcacaccgca    13320
tatggtgcac tctcagtaca atctgctctg atgccgcata gttaagccag ccccgacacc   13380
cgccaacacc cgctgacgag ct                                            13402
```

<210> SEQ ID NO 75
<211> LENGTH: 110
<212> TYPE: DNA
<213> ORGANISM: artificial sequence
<220> FEATURE:
<223> OTHER INFORMATION: primer

<400> SEQUENCE: 75

```
gcagtacaaa tgttacgggg taccggcgcg ccgctagctt aattaacgga ccgatgcatg    60
agctcacgcg taccggtgct cttcgatcta cgtaagaagg ccttcctatc               110
```

<210> SEQ ID NO 76
<211> LENGTH: 110
<212> TYPE: DNA
<213> ORGANISM: artificial sequence

```
<220> FEATURE:
<223> OTHER INFORMATION: primer

<400> SEQUENCE: 76
gataggaagg ccttcttacg tagatcgaag agcaccggta cgcgtgagct catgcatcgg      60
tccgttaatt aagctagcgg cgcgccggta ccccgtaaca tttgtactgc                110

<210> SEQ ID NO 77
<211> LENGTH: 77
<212> TYPE: DNA
<213> ORGANISM: artificial sequence
<220> FEATURE:
<223> OTHER INFORMATION: fragment

<400> SEQUENCE: 77
cggcgcgccg ctagcttaat taacggaccg atgcatgagc tcacgcgtac cggtgctctt      60
cgatctacgt aagaagg                                                    77

<210> SEQ ID NO 78
<211> LENGTH: 13611
<212> TYPE: DNA
<213> ORGANISM: artificial sequence
<220> FEATURE:
<223> OTHER INFORMATION: plasmid

<400> SEQUENCE: 78
aagtgagtcg tattacggac tggccgtcgt tttacaacgt cgtgactggg aaaaccctgg      60
cgttacccaa cttaatcgcc ttgcagcaca tcccccttc gccagctggc gtaatagcga     120
agaggcccgc accgatcgcc cttcccaaca gttgcgcagc ctgaatggcg aatggcgcct    180
gatgcggtat tttctcctta cgcatctgtg cggtatttca caccgcatat ggtgcactct    240
cagtacaatc tgctctgatg ccgcatagtt aagccagccc cgacacccgc caacacccgc    300
tgacgagctt agtaaagccc tcgctagatt ttaatgcgga gtttgcgatt acttcgccaa    360
ctattgcgat aacaagaaaa agccagcctt tcatgatata tctcccaatt tgtgtagggc    420
ttattatgca cgcttaaaaa taataaaagc agacttgacc tgatagtttg gctgtgagca    480
attatgtgct tagtgcatct aacgcttgag ttaagccgcg ccgcgaagcg cgtcggctt    540 gaacgaattg ttagacatta tttgccgact accttggtga tctcgccttt cacgtagtgg    600
acaaattctt ccaactgatc tgcgcgcgag gccaagcgat cttcttcttg tccaagataa    660
gcctgtctag cttcaagtat gacgggctga tactgggccg gcaggcgctc cattgcccag    720
tcggcagcga catccttcgg cgcgatttg ccggttactg cgctgtacca aatgcgggac    780
aacgtaagca ctacatttcg ctcatcgcca gcccagtcgg gcggcgagtt ccatagcgtt    840
aaggtttcat ttagcgcctc aaatagatcc tgttcaggaa ccggatcaaa gagttcctcc    900
gccgctggac ctaccaaggc aacgctatgt tctcttgctt ttgtcagcaa gatagccaga    960
tcaatgtcga tcgtggctgg ctcgaagata cctgcaagaa tgtcattgcg ctgccattct   1020
ccaaattgca gttcgcgctt agctggataa cgccacggaa tgatgtcgtc gtgcacaaca   1080
atggtgactt ctacagcgcg gagaatctcg ctctctccag gggaagccga agtttccaaa   1140
aggtcgttga tcaaagctcg ccgcgttgtt tcatcaagcc ttacggtcac cgtaaccagc   1200
aaatcaatat cactgtgtgg cttcaggccg ccatccactg cggagccgta caaatgtacg   1260
gccagcaacg tcggttcgag atggcgctcg atgacgccaa ctacctctga tagttgagtc   1320
gatacttcgg cgatcaccgc ttccctcatg atgtttaact ttgttttagg gcgactgccc   1380
tgctgcgtaa catcgttgct gctccataac atcaaacatc gacccacggc gtaacgcgct   1440
```

```
tgctgcttgg atgcccgagg catagactgt accccaaaaa aacagtcata acaagccatg    1500
aaaaccgcca ctgcgccgtt accaccgctg cgttcggtca aggttctgga ccagttgcgt    1560
gagcgcatac gctacttgca ttacagctta cgaaccgaac aggcttatgt ccactgggtt    1620
cgtgccttca tccgtttcca cggtgtgcgt cacccggcaa ccttgggcag cagcgaagtc    1680
gaggcatttc tgtcctggct ggcgaacgag cgcaaggttt cggtctccac gcatcgtcag    1740
gcattggcgg ccttgctgtt cttctacggc aaggtgctgt gcacggatct gccctggctt    1800
caggagatcg gaagacctcg gccgtcgcgg cgcttgccgg tggtgctgac cccggatgaa    1860
gtggttcgca tcctcggttt tctggaaggc gagcatcgtt tgttcgccca gcttctgtat    1920
ggaacgggca tgcggatcag tgagggtttg caactgcggg tcaaggatct ggatttcgat    1980
cacggcacga tcatcgtgcg ggagggcaag ggctccaagg atcgggcctt gatgttaccc    2040
gagagcttgg cacccagcct gcgcgagcag gggaattaat tcccacgggt tttgctgccc    2100
gcaaacgggc tgttctggtg ttgctagttt gttatcagaa tcgcagatcc ggcttcagcc    2160
ggtttgccgg ctgaaagcgc tatttcttcc agaattgcca tgatttttc cccacgggag     2220 gcgtcactgg ctcccgtgtt gtcggcagct ttgattcgat aagcagcatc gcctgtttca    2280
ggctgtctat gtgtgactgt tgagctgtaa caagttgtct caggtgttca atttcatgtt    2340
ctagttgctt tgttttactg gtttcacctg ttcattagg tgttacatgc tgttcatctg     2400
ttacattgtc gatctgttca tggtgaacag ctttgaatgc accaaaaact cgtaaaagct    2460
ctgatgtatc tatcttttt acaccgtttt catctgtgca tatggacagt tttccctttg     2520
atatgtaacg gtgaacagtt gttctacttt tgtttgttag tcttgatgct tcactgatag    2580
atacaagagc cataagaacc tcagatcctt ccgtatttag ccagtatgtt ctctagtgtg    2640
gttcgttgtt tttgcgtgag ccatgagaac gaaccattga gatcatactt actttgcatg    2700
tcactcaaaa attttgcctc aaaactggtg agctgaattt ttgcagttaa agcatcgtgt    2760 agtgttttc ttagtccgtt atgtaggtag gaatctgatg taatggttgt tggtattttg     2820
tcaccattca ttttatctg gttgttctca agttcggtta cgagatccat ttgtctatct     2880
agttcaactt ggaaaatcaa cgtatcagtc gggcggcctc gcttatcaac caccaatttc    2940
atattgctgt aagtgtttaa atctttactt attggtttca aaaccccattg gttaagcctt   3000 ttaaactcat ggtagttatt ttcaagcatt aacatgaact taaattcatc aaggctaatc    3060
tctatatttg ccttgtgagt tttcttttgt gttagttctt ttaataacca ctcataaatc    3120
ctcatagagt atttgttttc aaaagactta acatgttcca gattatattt tatgaatttt    3180
tttaactgga aaagataagg caatatctct tcactaaaaa ctaattctaa tttttcgctt    3240
gagaacttgg catagtttgt ccactggaaa atctcaaagc ctttaaccaa aggattcctg    3300
atttccacag ttctcgtcat cagctctctg gttgctttag ctaatacacc ataagcattt    3360
tccctactga tgttcatcat ctgagcgtat tggttataag tgaacgatac cgtccgttct    3420
ttccttgtag ggttttcaat cgtggggttg agtagtgcca cacagcataa aattagcttg    3480
gtttcatgct ccgttaagtc atagcgacta atcgctagtt catttgcttt gaaaacaact    3540
aattcagaca tacatctcaa ttggtctagg tgattttaat cactatacca attgagatgg    3600
gctagtcaat gataattact agctagtcct tttcctttga gttgtgggta tctgtaaatt    3660
ctgctagacc tttgctggaa aacttgtaaa ttctgctaga ccctctgtaa attccgctag    3720
acctttgtgt gttttttttg tttatattca agtggttata atttatagaa taagaaagaa    3780
ataaaaaaag ataaaaagaa tagatcccag ccctgtgtat aactcactac tttagtcagt    3840
```

```
tccgcagtat tacaaaagga tgtcgcaaac gctgtttgct cctctacaaa acagacctta    3900
aaaccctaaa ggcttaagta gcaccctcgc aagctcgggc aaatcgctga atattccttt    3960
tgtctccgac catcaggcac ctgagtcgct gtcttttcg tgacattcag ttcgctgcgc     4020
tcacggctct ggcagtgaat gggggtaaat ggcactacag gcgccttta tggattcatg     4080 caaggaaact acccataata caagaaaagc ccgtcacggg cttctcaggg cgttttatgg    4140
cgggtctgct atgtggtgct atctgacttt ttgctgttca gcagttcctg ccctctgatt    4200
ttccagtctg accacttcgg attatcccgt gacaggtcat tcagactggc taatgcaccc    4260
agtaaggcag cggtatcatc aacaggctta cccgtcttac tgtcgggaat tcatttaaat    4320
agtcaaaagc ctccgaccgg aggcttttga ctgctaggcg atctgtgctg tttgccacgg    4380
tatgcagcac cagcgcgaga ttatgggctc gcacgctcga ctgtcggacg ggggcactgg    4440
aacgagaagt caggcgagcc gtcacgccct tgacaatgcc acatcctgag caaataattc    4500
aaccactaaa caaatcaacc gcgtttcccg gaggtaacca agcttgcggg agagaatgat    4560
gaacaagagc caacaagttc agacaatcac cctggccgcc gcccagcaaa tggcggcggc    4620
ggtggaaaaa aaagccactg agatcaacgt ggcggtggtg ttttccgtag ttgaccgcgg    4680
aggcaacacg ctgcttatcc agcggatgga cgaggccttc gtctccagct gcgatatttc    4740
cctgaataaa gcctggagcg cctgcagcct gaagcaaggt acccatgaaa ttacgtcagc    4800
ggtccagcca ggacaatctc tgtacggtct gcagctaacc aaccaacagc gaattattat    4860
ttttggcggc ggcctgccag ttattttaa tgagcaggta attggcgccg tcggcgttag     4920
cggcggtacg gtcgagcagg atcaattatt agcccagtgc gccctggatt gttttttccgc   4980 attataacct gaagcgagaa ggtatattat gagctatcgt atgttccgcc aggcattctg    5040
agtgttaacg aggggaccgt catgtcgctt tcaccgccag gcgtacgcct gttttacgat    5100
ccgcgcgggc accatgccgg cgccatcaat gagctgtgct gggggctgga ggagcagggg    5160
gtcccctgcc agaccataac ctatgacgga ggcggtgacg ccgctgcgct gggcgccctg    5220
gcggccagaa gctcgcccct gcgggtgggt atcgggctca gcgcgtccgg cgagatagcc    5280
ctcactcatg cccagctgcc ggcggacgcg ccgctggcta ccggacacgt caccgatagc    5340
gacgatcaac tgcgtacgct cggcgccaac gccgggcagc tggttaaagt cctgccgtta    5400
agtgagagaa actgaatgta tcgtatctat acccgcaccg gggataaagg caccaccgcc    5460
ctgtacggcg gcagccgcat cgagaaagac catattcgcg tcgaggccta cggcaccgtc    5520
gatgaactga tatcccagct gggcgtctgc tacgccacga cccgcgacgc cgggctgcgg    5580
gaaagcctgc accatattca gcagacgctg ttcgtgctgg gggctgaact ggccagcgat    5640
gcgcggggcc tgacccgcct gagccagacg atcgcgaag aggagatcac cgccctggag     5700
cggcttatcg accgcaatat ggccgagagc ggcccgttaa acagttcgt gatcccgggg     5760 aggaatctcg cctctgccca gctgcacgtg gcgcgcaccc agtcccgtcg gctcgaacgc    5820
ctgctgacgg ccatggaccg cgcgcatccg ctgcgcgacg cgctcaaacg ctacagcaat    5880
cgcctgtcgg atgccctgtt ctccatggcg cgaatcgaag agactaggcc tgatgcttgc    5940
gcttgaactg gcctagcaaa cacagaaaaa agcccgcacc tgacagtgcg gcttttttt     6000 ttcctaggcg atctgtgctg tttgccacgg tatgcagcac cagcgcgaga ttatgggctc    6060
gcacgctcga ctgtcggacg ggggcactgg aacgagaagt caggcgagcc gtcacgccct    6120
tgacaatgcc acatcctgag caaataattc aaccactaaa caaatcaacc gcgtttcccg    6180
gaggtaacca agcttcacct tttgagccga tgaacaatga aaagatcaaa acgatttgca    6240
```

```
gtactggccc agcgccccgt caatcaggac gggctgattg gcgagtggcc tgaagagggg      6300
ctgatcgcca tggacagccc ctttgacccg gtctcttcag taaaagtgga caacggtctg      6360
atcgtcgaac tggacggcaa acgccggac cagtttgaca tgatcgaccg atttatcgcc       6420
gattacgcga tcaacgttga gcgcacagag caggcaatgc gcctggaggc ggtggaaata      6480
gcccgtatgc tggtggatat tcacgtcagc cgggaggaga tcattgccat cactaccgcc      6540
atcacgccgg ccaaagcggt cgaggtgatg gcgcagatga acgtggtgga gatgatgatg      6600
gcgctgcaga gatgcgtgc ccgccggacc ccctccaacc agtgccacgt caccaatctc       6660
aaagataatc cggtgcagat tgccgctgac gccgccgagg ccgggatccg cggcttctca      6720
gaacaggaga ccacggtcgg tatcgcgcgc tacgcgccgt ttaacgccct ggcgctgttg      6780
gtcggttcgc agtgcggccg ccccggcgtg ttgacgcagt gctcggtgga agaggccacc      6840
gagctggagc tgggcatgcg tggcttaacc agctacgccg agacggtgtc ggtctacggc      6900
accgaagcgg tatttaccga cggcgatgat acgccgtggt caaaggcgtt cctcgcctcg      6960
gcctacgcct cccgcgggtt gaaaatgcgc tacacctccg gcaccggatc cgaagcgctg      7020
atgggctatt cggagagcaa gtcgatgctc tacctcgaat cgcgctgcat cttcattact      7080
aaaggcgccg gggttcaggg actgcaaaac ggcgcggtga gctgtatcgg catgaccggc      7140
gctgtgccgt cgggcattcg gcggtgctg gcggaaaacc tgatcgcctc tatgctcgac       7200
ctcgaagtgg cgtccgccaa cgaccagact ttctcccact cggatattcg ccgcaccgcg      7260
cgcaccctga tgcagatgct gccgggcacc gactttattt tctccggcta cagcgcggtg      7320
ccgaactacg acaacatgtt cgccggctcg aacttcgatg cggaagattt tgatgattac      7380
aacatcctgc agcgtgacct gatggttgac ggcggcctgc gtccggtgac cgaggcggaa      7440
accattgcca ttcgccagaa agcggcgcgg gcgatccagg cggttttccg cgagctgggg      7500
ctgccgccaa tcgccgacga ggaggtggag ccgccacct acgcgcacgg cagcaacgag       7560
atgccgccgc gtaacgtggt ggaggatctg agtgcggtgg aagagatgat gaagcgcaac      7620
atcaccggcc tcgatattgt cggcgcgctg agccgcagcg gctttgagga tatcgccagc      7680
aatattctca atatgctgcg ccagcgggtc accggcgatt acctgcagac ctcggccatt      7740
ctcgatcggc agttcgaggt ggtgagtgcg gtcaacgaca tcaatgacta tcaggggccg      7800
ggcaccggct atcgcatctc tgccgaacgc tgggcggaga tcaaaaatat tccgggcgtg      7860
gttcagcccg acaccattga ataaggcggt attcctgtgc aacagacaac ccaaattcag      7920
ccctctttta ccctgaaaac ccgcgagggc ggggtagctt ctgccgatga acgcgccgat      7980
gaagtggtga tcggcgtcgg ccctgccttc gataaacacc agcatcacac tctgatcgat      8040
atgccccatg gcgcgatcct caaagagctg attgccgggg tggaagaaga ggggcttcac      8100
gcccgggtgg tgcgcattct gcgcacgtcc gacgtctcct ttatggcctg ggatgcggcc      8160
aacctgagcg gctcggggat cggcatcggt atccagtcga aggggaccac ggtcatccat      8220
cagcgcgatc tgctgccgct cagcaacctg gagctgttct cccaggcgcc gctgctgacg      8280
ctggagacct accggcagat tggcaaaaac gctgcgcgct atgcgcgcaa agagtcacct      8340
tcgccggtgc cggtggtgaa cgatcagatg gtgcggccga aatttatggc caaagccgcg      8400
ctatttcata tcaaagagac caaacatgtg gtgcaggacg ccgagcccgt cacccctgcac     8460 atcgacttag taagggagtg accatgagcg agaaaaccat gcgcgtgcag gattatccgt      8520
tagccacccg ctgcccggag catatcctga cgcctaccgg caaaccattg accgatatta      8580
ccctcgagaa ggtgctctct ggcgaggtgg gcccgcagga tgtgcggatc tcccgccaga      8640
```

```
cccttgagta ccaggcgcag attgccgagc agatgcagcg ccatgcggtg gcgcgcaatt     8700
tccgccgcgc ggcggagctt atcgccattc ctgacgagcg cattctggct atctataacg     8760
cgctgcgccc gttccgctcc tcgcaggcgg agctgctggc gatcgccgac gagctggagc     8820
acacctggca tgcgacagtg aatgccgcct tgtccgggga gtcggcggaa gtgtatcagc     8880
agcggcataa gctgcgtaaa ggaagctaag cggaggtcag catgccgtta atagccggga     8940
ttgatatcgg caacgccacc accgaggtgg cgctggcgtc cgactacccg caggcgaggg     9000
cgtttgttgc cagcgggatc gtcgcgacga cgggcatgaa agggacgcgg gacaatatcg     9060
ccgggaccct cgccgcgctg gagcaggccc tggcgaaaac accgtggtcg atgagcgatg     9120
tctctcgcat ctatcttaac gaagccgcgc cggtgattgg cgatgtggcg atggagacca     9180
tcaccgagac cattatcacc gaatcgacca tgatcggtca taacccgcag acgccgggcg     9240
gggtgggcgt tggcgtgggg acgactatcg ccctcgggcg gctggcgacg ctgccggcgg     9300
cgcagtatgc cgagggggtgg atcgtactga ttgacgacgc cgtcgatttc cttgacgccg     9360
tgtggtggct caatgaggcg ctcgaccggg ggatcaacgt ggtggcggcg atcctcaaaa     9420
aggacgacgc cgtgctggtg aacaaccgcc tgcgtaaaac cctgccggtg gtggatgaag     9480
tgacgctgct ggagcaggtc cccgaggggg taatggcggc ggtggaagtg gccgcgccgg     9540
gccaggtggt gcggatcctg tcgaatccct acgggatcgc caccttcttc gggctaagcc     9600
cggaagagac ccaggccatc gtccccatcg cccgcgccct gattggcaac cgttccgcgg     9660
tggtgctcaa gaccccgcag ggggatgtgc agtcgcgggt gatcccggcg gcaacctct     9720
acattagcgg cgaaaagcgc cgcggagagg ccgatgtcgc cgagggcgcg gaagccatca     9780
tgcaggcgat gagcgcctgc gctccggtac gcgacatccg cggcgaaccg ggcacccacg     9840
ccggcggcat gcttgagcgg gtgcgcaagg taatggcgtc cctgaccggc catgagatga     9900
gcgcgatata catccaggat ctgctggcgg tggatacgtt tattccgcgc aaggtgcagg     9960
gcgggatggc cggcgagtgc gccatggaga atgccgtcgg gatggcggcg atggtgaaag    10020
cggatcgtct gcaaatgcag gttatcgccc gcgaactgag cgcccgactg cagaccgagg    10080
tggtggtggg cggcgtggag gccaacatgg ccatcgccgg ggcgttaacc actcccggct    10140
gtgcggcgcc gctggcgatc ctcgacctcg gcgccggctc gacggatgcg gcgatcgtca    10200
acgcggaggg gcagataacg gcggtccatc tcgccggggc ggggaatatg gtcagcctgt    10260
tgattaaaac cgagctgggc ctcgaggatc tttcgctggc ggaagcgata aaaaaatacc    10320
cgctggccaa agtggaaagc ctgttcagta ttcgtcacga gaatggcgcg gtggagttct    10380
ttcgggaagc cctcagcccg gcggtgttcg ccaaagtggt gtacatcaag gagggcgaac    10440
tggtgccgat cgataacgcc agcccgctgg aaaaaattcg tctcgtgcgc cggcaggcga    10500
aagagaaagt gtttgtcacc aactgcctgc gcgcgctgcg ccaggtctca cccgcggtt    10560
ccattcgcga tatcgccttt gtggtgctgg tgggcggctc atcgctggac tttgagatcc    10620
cgcagcttat cacggaagcc ttgtcgcact atggcgtggt cgccgggcag ggcaatattc    10680
ggggaacaga agggccgcgc aatgcggtcg ccaccgggct gctactggcc ggtcaggcga    10740
attaaacggg cgctcgcgcc agcctctagg tacaaataaa aaaggcacgt cagatgacgt    10800
gcctttttc ttgtctagcg tgcaccaatg cttctggcgt caggcagcca tcggaagctg    10860
tggtatggct gtgcaggtcg taaatcactg cataattcgt gtcgctcaag gcgcactccc    10920
gttctgata atgttttttg cgccgacatc ataacggttc tggcaaatat tctgaaatga    10980
gctgttgaca attaatcatc cggctcgtat aatgtgtgga attgtgagcg gataacaatt    11040
```

```
tcacacagga acagaccat gactagtaag gaggacaatt ccatggctgc tgctgctgat    11100
agattaaact taacttccgg ccacttgaat gctggtagaa agagaagttc ctcttctgtt    11160
tctttgaagg ctgccgaaaa gcctttcaag gttactgtga ttggatctgg taactggggt    11220
actactattg ccaaggtggt tgccgaaaat tgtaagggat acccagaagt tttcgctcca    11280
atagtacaaa tgtgggtgtt cgaagaagag atcaatggtg aaaaattgac tgaaatcata    11340
aatactagac atcaaaacgt gaaatacttg cctggcatca ctctacccga caatttggtt    11400
gctaatccag acttgattga ttcagtcaag gatgtcgaca tcatcgtttt caacattcca    11460
catcaatttt tgccccgtat ctgtagccaa ttgaaaggtc atgttgattc acacgtcaga    11520
gctatctcct gtctaaaggg ttttgaagtt ggtgctaaag gtgtccaatt gctatcctct    11580
tacatcactg aggaactagg tattcaatgt ggtgctctat ctggtgctaa cattgccacc    11640
gaagtcgctc aagaacactg gtctgaaaca acagttgctt accacattcc aaaggatttc    11700
agaggcgagg gcaaggacgt cgaccataag gttctaaagg ccttgttcca cagaccttac    11760
ttccacgtta gtgtcatcga agatgttgct ggtatctcca tctgtggtgc tttgaagaac    11820
gttgttgcct taggttgtgg tttcgtcgaa ggtctaggct ggggtaacaa cgcttctgct    11880
gccatccaaa gagtcggttt gggtgagatc atcagattcg gtcaaatgtt tttcccagaa    11940
tctagagaag aaacatacta ccaagagtct gctggtgttg ctgatttgat cacccacctgc   12000 gctggtggta gaaacgtcaa ggttgctagg ctaatggcta cttctggtaa ggacgcctgg    12060
gaatgtgaaa aggagttgtt gaatggccaa tccgctcaag gtttaattac ctgcaaagaa    12120
gttcacgaat ggttggaaac atgtggctct gtcgaagact tcccattatt tgaagccgta    12180
taccaaatcg tttacaacaa ctacccaatg aagaacctgc cggacatgat tgaagaatta    12240
gatctacatg aagattagat ttattggatc caggaaacag actagaatta tgggattgac    12300
tactaaacct ctatctttga agttaacgc cgctttgttc gacgtcgacg gtaccattat    12360
catctctcaa ccagccattg ctgcattctg gagggatttc ggtaaggaca aaccttattt    12420
cgatgctgaa cacgttatcc aagtctcgca tggttggaga acgtttgatg ccattgctaa    12480
gttcgctcca gactttgcca atgaagagta tgttaacaaa ttagaagctg aaattccggt    12540
caagtacggt gaaaaatcca ttgaagtccc aggtgcagtt aagctgtgca acgctttgaa    12600
cgctctacca aaagagaaat gggctgtggc aacttccggt acccgtgata tggcacaaaa    12660
atggttcgag catctgggaa tcaggagacc aaagtacttc attaccgcta atgatgtcaa    12720
acagggtaag cctcatccag aaccatatct gaagggcagg aatggcttag gatatccgat    12780
caatgagcaa gacccttcca aatctaaggt agtagtattt gaagacgctc cagcaggtat    12840
tgccgccgga aaagccgccg gttgtaagat cattggtatt gccactactt tcgacttgga    12900
cttcctaaag gaaaaaggct gtgacatcat tgtcaaaaac cacgaatcca tcagagttgg    12960
cggctacaat gccgaaacag acgaagttga attcatttt gacgactact tatatgctaa    13020
ggacgatctg ttgaaatggt aacccgggct gcaggcatgc aagcttggct gttttggcgg    13080
atgagagaag atttttcagcc tgatacagat taaatcagaa cgcagaagcg gtctgataaa    13140
acagaatttg cctggcggca gtagcgcggt ggtcccacct gacccatgc cgaactcaga    13200 agtgaaacgc cgtagcgccg atggtagtgt ggggtctccc catgcgagag tagggaactg    13260
ccaggcatca aataaaacga aaggctcagt cgaaagactg gcctttcgt tttatctgtt    13320 gtttgtcggt gaacgctctc ctgagtagga caaatccgcc gggagcggat ttgaacgttg    13380
cgaagcaacg gcccggaggg tggcgggcag gacgcccgcc ataaactgcc aggcatcaaa    13440
```

```
ttaagcagaa ggccatcctg acggatggcc tttttgcgtt tctacaaact ccagctggat   13500
cgggcgctag agtatacatt taaatggtac cggcgcgccg ctagcttaat taacggaccg   13560
atgcatgagc tcacgcgtac cggtgctctt cgatctacgt aagaaggcct t            13611

<210> SEQ ID NO 79
<211> LENGTH: 4490
<212> TYPE: DNA
<213> ORGANISM: artificial sequence
<220> FEATURE:
<223> OTHER INFORMATION: plasmid

<400> SEQUENCE: 79
tagtaaagcc ctcgctagat tttaatgcgg atgttgcgat tacttcgcca actattgcga     60
taacaagaaa aagccagcct tcatgatat atctcccaat ttgtgtaggg cttattatgc    120
acgcttaaaa ataataaaag cagacttgac ctgatagttt ggctgtgagc aattatgtgc    180
ttagtgcatc taacgcttga gttaagccgc gccgcgaagc ggcgtcggct tgaacgaatt    240
gttagacatt atttgccgac taccttggtg atctcgcctt tcacgtagtg acaaattct    300 tccaactgat ctgcgcgcga ggccaagcga tcttcttctt gtccaagata agcctgtcta    360
gcttcaagta tgacgggctg atactgggcc ggcaggcgct ccattgccca gtcggcagcg    420
acatccttcg gcgcgatttt gccggttact gcgctgtacc aaatgcggga caacgtaagc    480
actacatttc gctcatcgcc agcccagtcg ggcggcgagt tccatagcgt taaggtttca    540
tttagcgcct caaatagatc ctgttcagga accggatcaa agagttcctc cgccgctgga    600
cctaccaagg caacgctatg ttctcttgct tttgtcagca agatagccag atcaatgtcg    660
atcgtggctg gctcgaagat acctgcaaga atgtcattgc gctgccattc tccaaattgc    720
agttcgcgct tagctggata acgccacgga atgatgtcgt cgtgcacaac aatggtgact    780
tctacagcgc ggagaatctc gctctctcca ggggaagccg aagtttccaa aggtcgttg     840 atcaaagctc gccgcgttgt ttcatcaagc cttacggtca ccgtaaccag caaatcaata    900
tcactgtgtg gcttcaggcc gccatccact gcggagccgt acaaatgtac ggccagcaac    960
gtcggttcga gatggcgctc gatgacgcca actacctctg atagttgagt cgatacttcg   1020
gcgatcaccg cttccctcat gatgtttaac tttgttttag gcgactgcc ctgctgcgta   1080 acatcgttgc tgctccataa catcaaacat cgacccacgg cgtaacgcgc ttgctgcttg   1140
gatgcccgag gcatagactg taccccaaaa aaacagtcat aacaagccat gaaaaccgcc   1200
actgcgccgt taccaccgct gcgttcggtc aaggttctgg accagttgcg tgagcgcata   1260
cgctacttgc attacagctt acgaaccgaa caggcttatg tccactgggt tcgtgccttc   1320
atccgtttcc acggtgtgcg tcacccggca accttgggca gcagcgaagt cgaggcattt   1380
ctgtcctggc tggcgaacga gcgcaaggtt tcggtctcca cgcatcgtca ggcattggcg   1440
gccttgctgt tcttctacgg caaggtgctg tgcacggatc tgccctggct tcaggagatc   1500
ggaagacctc ggccgtcgcg gcgcttgccg gtggtgctga cccgggatga agtggttcgc   1560
atcctcggtt ttctggaagg cgagcatcgt ttgttcgccc agcttctgta tggaacgggc   1620
atgcggatca gtgagggttt gcaactgcgg gtcaaggatc tggatttcga tcacggcacg   1680
atcatcgtgc gggagggcaa gggctccaag gatcgggcct tgatgttacc cgagagcttg   1740
gcacccagcc tgcgcgagca ggggaattaa ttcccacggg ttttgctgcc cgcaaacggg   1800
ctgttctggt gttgctagtt tgttatcaga atcgcagatc cggcttcagc cggtttgccg   1860
gctgaaagcg ctatttcttc cagaattgcc atgattttt ccccacggga ggcgtcactg   1920
```

```
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040 ttgtttact ggtttcacct gttctattag gtgttacatg ctgttcatct gttacattgt     2100
cgatctgttc atggtgaaca gctttgaatg caccaaaaac tcgtaaaagc tctgatgtat    2160
ctatcttttt tacaccgttt tcatctgtgc atatggacag ttttccctt gatatgtaac     2220 ggtgaacagt tgttctactt ttgtttgtta gtcttgatgc ttcactgata gatacaagag    2280
ccataagaac ctcagatcct tccgtattta gccagtatgt tctctagtgt ggttcgttgt    2340 tttgcgtga gccatgagaa cgaaccattg agatcatact tactttgcat gtcactcaaa     2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact     2580
tggaaaatca acgtatcagt cgggcggcct cgcttatcaa ccaccaattt catattgctg    2640
taagtgttta atctttact tattggtttc aaaacccatt ggttaagcct tttaaactca     2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaaagactt aacatgttcc agattatatt ttatgaattt ttttaactgg   2880 aaagataag gcaatatctc ttcactaaaa actaattcta attttcgct tgagaacttg     2940 gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctt     3360 gctggaaaac ttgtaaattc tgctagaccc tctgtaaatt ccgctagacc tttgtgtgtt    3420
ttttttgttt atattcaagt ggttataatt tatagaataa agaaagaata aaaaagata     3480 aaagaatag atcccagccc tgtgtataac tcactacttt agtcagttcc gcagtattac     3540
aaaaggatgc cgcaaacgct gtttgctcct ctacaaaaca gaccttaaaa ccctaaaggc    3600
ttaagtagca ccctcgcaag ctcgggcaaa tcgctgaata ttccttttgt ctccgaccat    3660
caggcacctg agtcgctgtc ttttcgtga cattcagttc gctgcgctca cggctctggc    3720
agtgaatggg ggtaaatggc actacaggcg ccttttatgg attcatgcaa ggaaactacc    3780
cataatacaa gaaagcccg tcacgggctt ctcagggcgt tttatggcgg gtctgctatg    3840
tggtgctatc tgactttttg ctgttcagca gttcctgccc tctgattttc cagtctgacc    3900
acttcggatt atcccgtgac aggtcattca gactggctaa tgcacccagt aaggcagcgg    3960
tatcatcaac aggcttaccc gtcttactgt cgggaattca tttaaatagt caaaagcctc    4020
cgaccggagg cttttgactg ctagcaaaca cagaaaaaag cccgcacctg acagtgcggg    4080 ctttttttt cctaggtaca aataaaaaag gcacgtcaga tgacgtgcct ttttcttgt     4140 ctagagtata catttaaatg gtaccctcta gtcaaggcct taagtgagtc gtattacgga    4200
ctggccgtcg ttttacaacg tcgtgactgg gaaaaccctg gcgttaccca acttaatcgc    4260
cttgcagcac atccccctt cgccagctgg cgtaatagcg aagaggcccg caccgatcgc     4320
```

-continued

```
ccttcccaac agttgcgcag cctgaatggc gaatggcgcc tgatgcggta ttttctcctt    4380
acgcatctgt gcggtatttc acaccgcata tggtgcactc tcagtacaat ctgctctgat    4440
gccgcatagt taagccagcc ccgacacccg ccaacacccg ctgacgagct                4490
```

```
<210> SEQ ID NO 80
<211> LENGTH: 33
<212> TYPE: DNA
<213> ORGANISM: artificial sequence
<220> FEATURE:
<223> OTHER INFORMATION: primer

<400> SEQUENCE: 80
cataagcttg cgggagagaa tgatgaacaa gag                                   33

<210> SEQ ID NO 81
<211> LENGTH: 31
<212> TYPE: DNA
<213> ORGANISM: artificial sequence
<220> FEATURE:
<223> OTHER INFORMATION: primer

<400> SEQUENCE: 81
acgcctaggc cagttcaagc gcaagcatca g                                     31

<210> SEQ ID NO 82
<211> LENGTH: 25
<212> TYPE: DNA
<213> ORGANISM: artificial sequence
<220> FEATURE:
<223> OTHER INFORMATION: primer

<400> SEQUENCE: 82
ctttaatctg cacaccccaa cccgc                                            25

<210> SEQ ID NO 83
<211> LENGTH: 25
<212> TYPE: DNA
<213> ORGANISM: artificial sequence
<220> FEATURE:
<223> OTHER INFORMATION: primer

<400> SEQUENCE: 83
ggcggtatca atcgagcgat aaccc                                            25
```